US011246868B2

(12) United States Patent
Aaronson et al.

(10) Patent No.: US 11,246,868 B2
(45) Date of Patent: Feb. 15, 2022

(54) TREATMENT OF HIPPO PATHWAY MUTANT TUMORS AND METHODS OF IDENTIFYING SUBJECTS AS CANDIDATES FOR TREATMENT

(71) Applicant: ICAHN SCHOOL OF MEDICINE AT MOUNT SINAI, New York, NY (US)

(72) Inventors: Stuart A. Aaronson, New York, NY (US); Albino Troilo, New York, NY (US); Erica K. Benson, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 52 days.

(21) Appl. No.: 16/095,784

(22) PCT Filed: Apr. 26, 2017

(86) PCT No.: PCT/US2017/029646

§ 371 (c)(1),
(2) Date: Oct. 23, 2018

(87) PCT Pub. No.: WO2017/189730

PCT Pub. Date: Nov. 2, 2017

(65) Prior Publication Data

US 2019/0125748 A1 May 2, 2019

Related U.S. Application Data

(60) Provisional application No. 62/327,903, filed on Apr. 26, 2016.

(51) Int. Cl.

| | |
|---|---|
| ***A61P 35/00*** | (2006.01) |
| ***C12Q 1/6886*** | (2018.01) |
| ***A61K 31/513*** | (2006.01) |
| ***A61K 31/506*** | (2006.01) |
| ***A61K 31/352*** | (2006.01) |
| ***A61K 31/519*** | (2006.01) |
| ***A61B 10/02*** | (2006.01) |
| ***A61K 31/495*** | (2006.01) |
| ***A61K 31/505*** | (2006.01) |
| ***A61K 31/33*** | (2006.01) |
| ***C07K 16/24*** | (2006.01) |
| ***C07K 16/30*** | (2006.01) |
| ***A61K 31/095*** | (2006.01) |
| ***A61K 31/7064*** | (2006.01) |

(52) U.S. Cl.

CPC ............ *A61K 31/513* (2013.01); *A61B 10/02* (2013.01); *A61K 31/095* (2013.01); *A61K 31/33* (2013.01); *A61K 31/352* (2013.01); *A61K 31/495* (2013.01); *A61K 31/505* (2013.01); *A61K 31/506* (2013.01); *A61K 31/519* (2013.01); *A61K 31/7064* (2013.01); *A61P 35/00* (2018.01); *C07K 16/24* (2013.01); *C07K 16/30* (2013.01); *C12Q 1/6886* (2013.01); *C12Q 2600/106* (2013.01)

(58) Field of Classification Search

None

See application file for complete search history.

(56) References Cited

U.S. PATENT DOCUMENTS

2016/0251348 A1 9/2016 Chedid et al.

FOREIGN PATENT DOCUMENTS

| | | |
|---|---|---|
| WO | 2015/063747 A2 | 5/2015 |
| WO | 2015/073813 A1 | 5/2015 |

OTHER PUBLICATIONS

Rienzo et al., "Fine-Needle Aspiration Biopsies for Gene Expression Ratio-Based Diagnostic and Prognostic Tests in Malignant Pleural Mesothelioma" Clinical Cancer Research vol. 17 no. 2 pp. 310-316 (Year: 2011).*

Li et al., "Merlin/NF2 Loss-Driven Tumorigenesis Linked to CRL4DCAF1-Mediated Inhibition of the Hippo Pathway Kinases Lats1 and 2 in the Nucleus" Cancer Cell vol. 26 pp. 48-60 (Year: 2014).*

Wu et al., "Tankyrase 1 inhibitiorXAV939 increases chemosensitivity in colon cancer cell lines via inhibition of the Wnt signaling pathway" International Journal of Oncology vol. 48 pp. 1333-1340 DOI: 10.3892/ijo.2016.3360 (Year: 2016).*

Harvey et al., "The Hippo pathway and human cancer" Nature Reviews Cancer vol. 13 pp. 246-257 (Year: 213).*

Lau et al., "A Novel Tankyrase Small-Molecule Inhibitor Suppresses APC Mutation-Driven Colorectal Tumor Growth," Cancer Research 73(10):3132-3144 (2013).

PCT International Search Report and Written Opinion for corresponding PCT/US2017/029646, dated Aug. 11, 2017.

Busch et al., "Evidence for Tankyrases as Antineoplastic Targets in Lung Cancer," BMC Cancer 13:211 (2013).

Ma et al., "Tankyrase Inhibitors Attenuate WNT/β-Catenin Signaling and Inhibit Growth of Hepatocellular Carcinoma Cells," Oncotarget 6(28):25390-25401 (2015).

Liu-Chittenden et al., "Genetic and Pharmacological Disruption of the TEAD-YAP Complex Suppresses the Oncogenic Activity of YAP," Genes and Development 26(12):1300-1305 (2012).

(Continued)

*Primary Examiner* — Eric Olson

(74) *Attorney, Agent, or Firm* — Troutman Pepper Hamilton Sanders LLP (Rochester)

(57) ABSTRACT

The present invention relates to a method of treating a tumor in a subject. This method involves administering to a subject having a Hippo pathway mutant tumor a tankyrase inhibitor, where the tumor is susceptible to treatment with the tankyrase inhibitor, and said administering is carried out to treat the tumor. The present invention also relates to a method of treating cancer in a subject, and a method of identifying a subject as a candidate for treatment.

14 Claims, 15 Drawing Sheets

Specification includes a Sequence Listing.

(56) References Cited

OTHER PUBLICATIONS

McGonigle et al., "E7449: A Dual Inhibitor of PARP1/2 and Tankyrase1/2 Inhibits Growth of DNA Repair Deficient Tumors and Antagonizes Wnt Signaling," Oncotarget 6(38):41307-41323 (2015).

Reddy et al., "Regulation of Hippo Signaling by EGFR-MAPK Signaling through Ajuba Family Proteins," Developmental Cell 24(5):459-471 (2013).

Wang et al., "Tankyrase Inhibitors Target YAP by Stabilizing Angiomotin Family Proteins," Cell Reports 13(3):524-532 (2015).

Extended European Search Report for European Patent Application No. 17790347.3 (dated Nov. 29, 2019).

Communication in corresponding European Patent Application No. 17790347.3 (dated Sep. 25, 2020).

* cited by examiner

FIGs. 1A-D
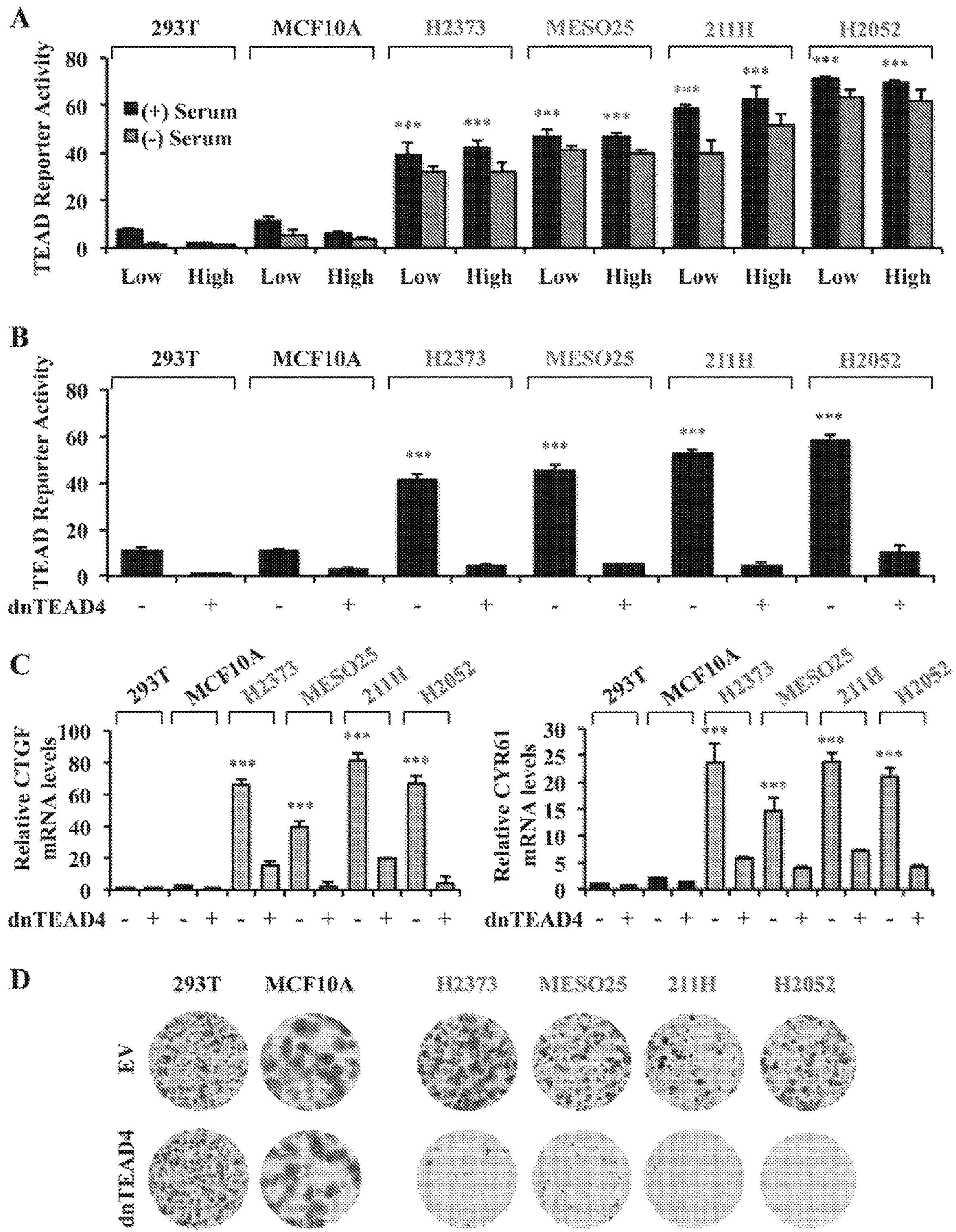

FIGs. 2A-J
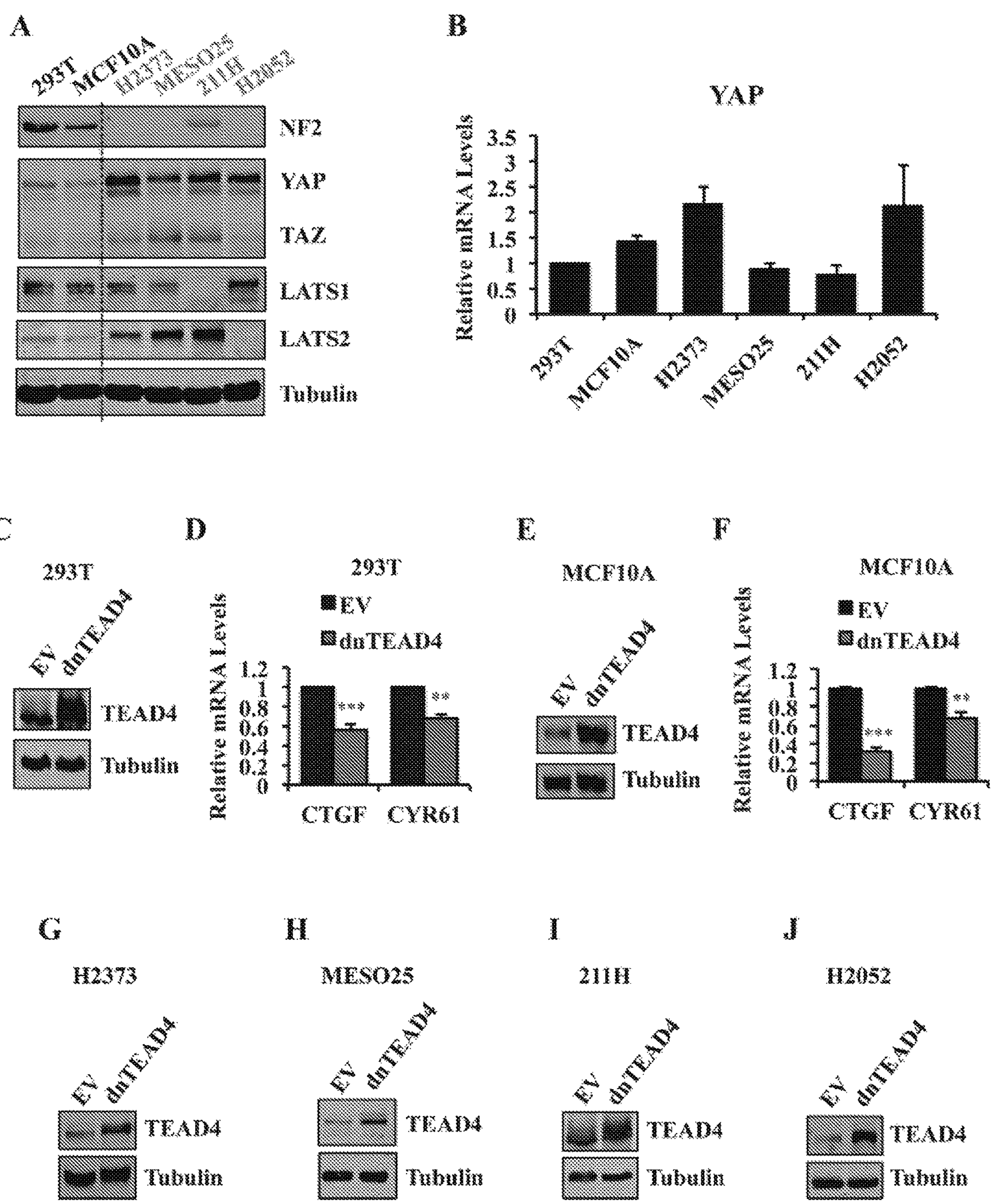

FIGs. 3A-C
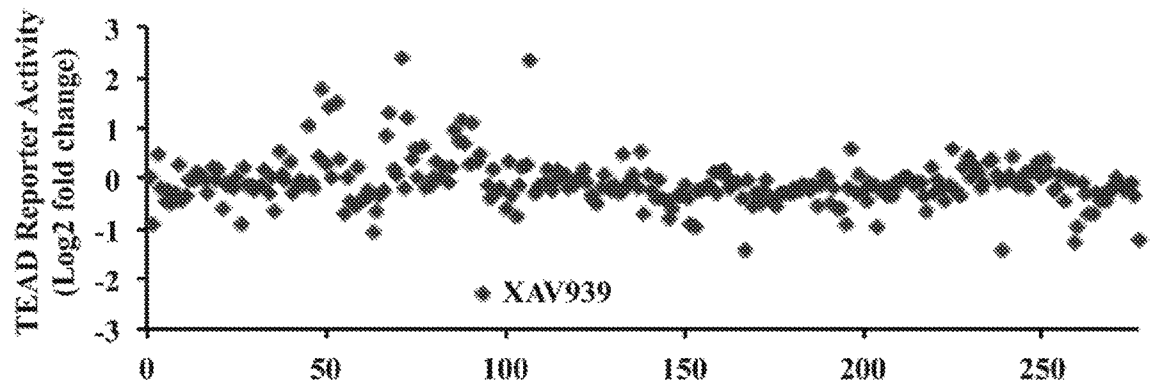
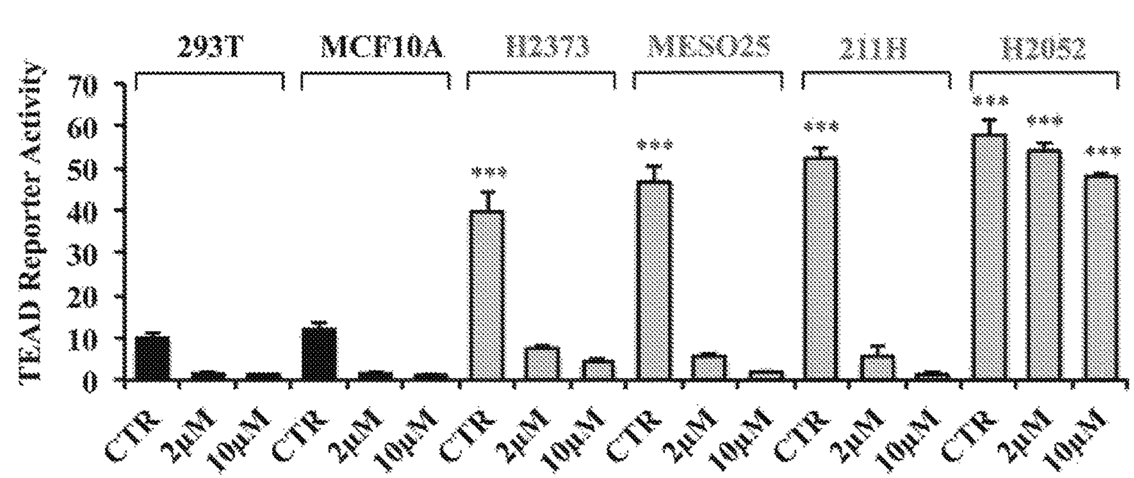
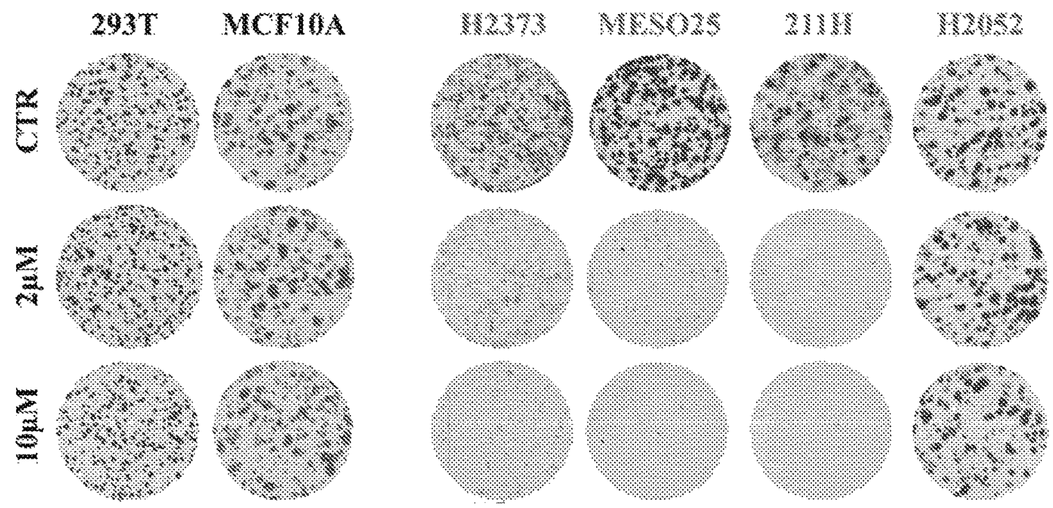

FIGs. 4A-F
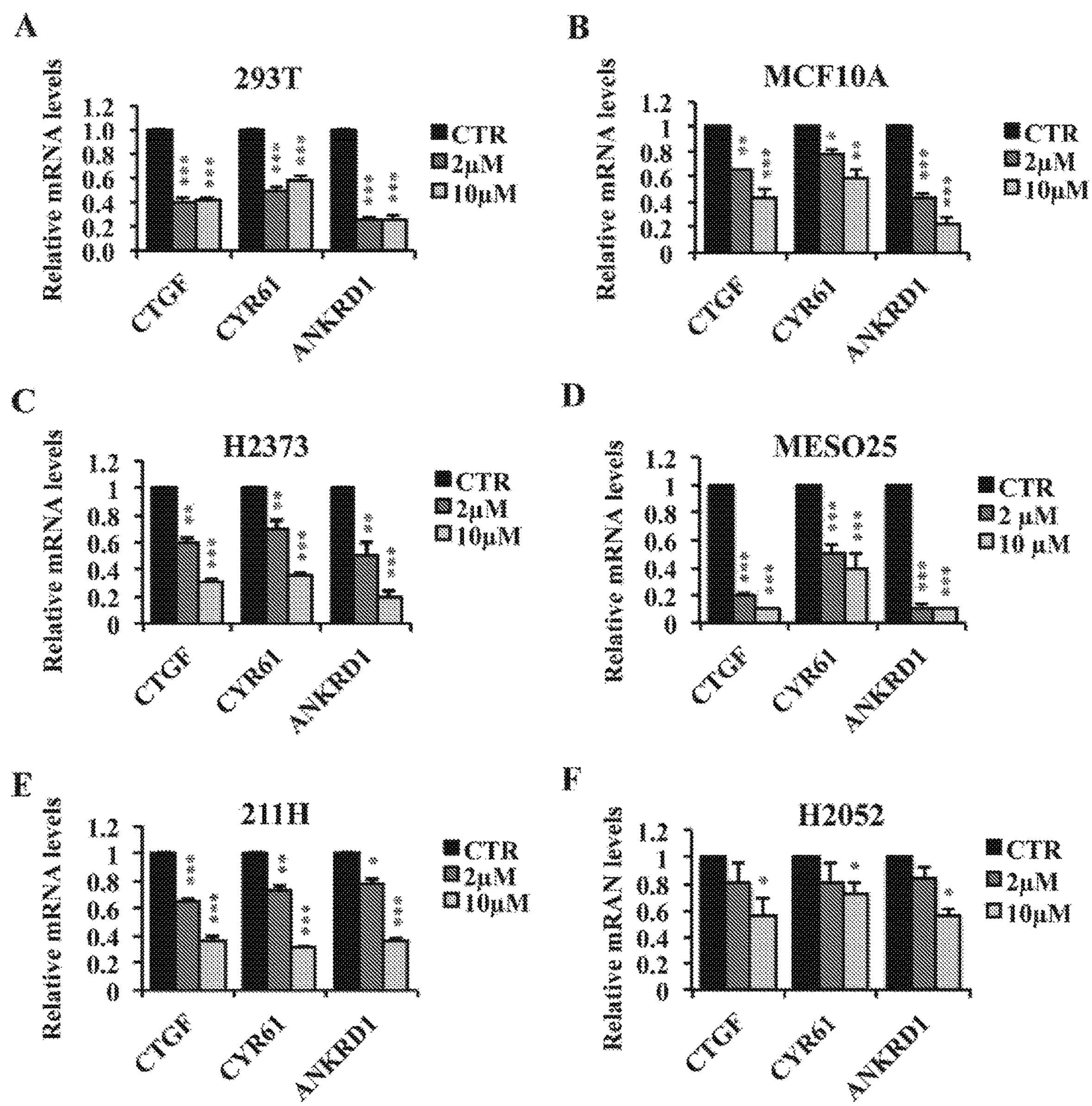

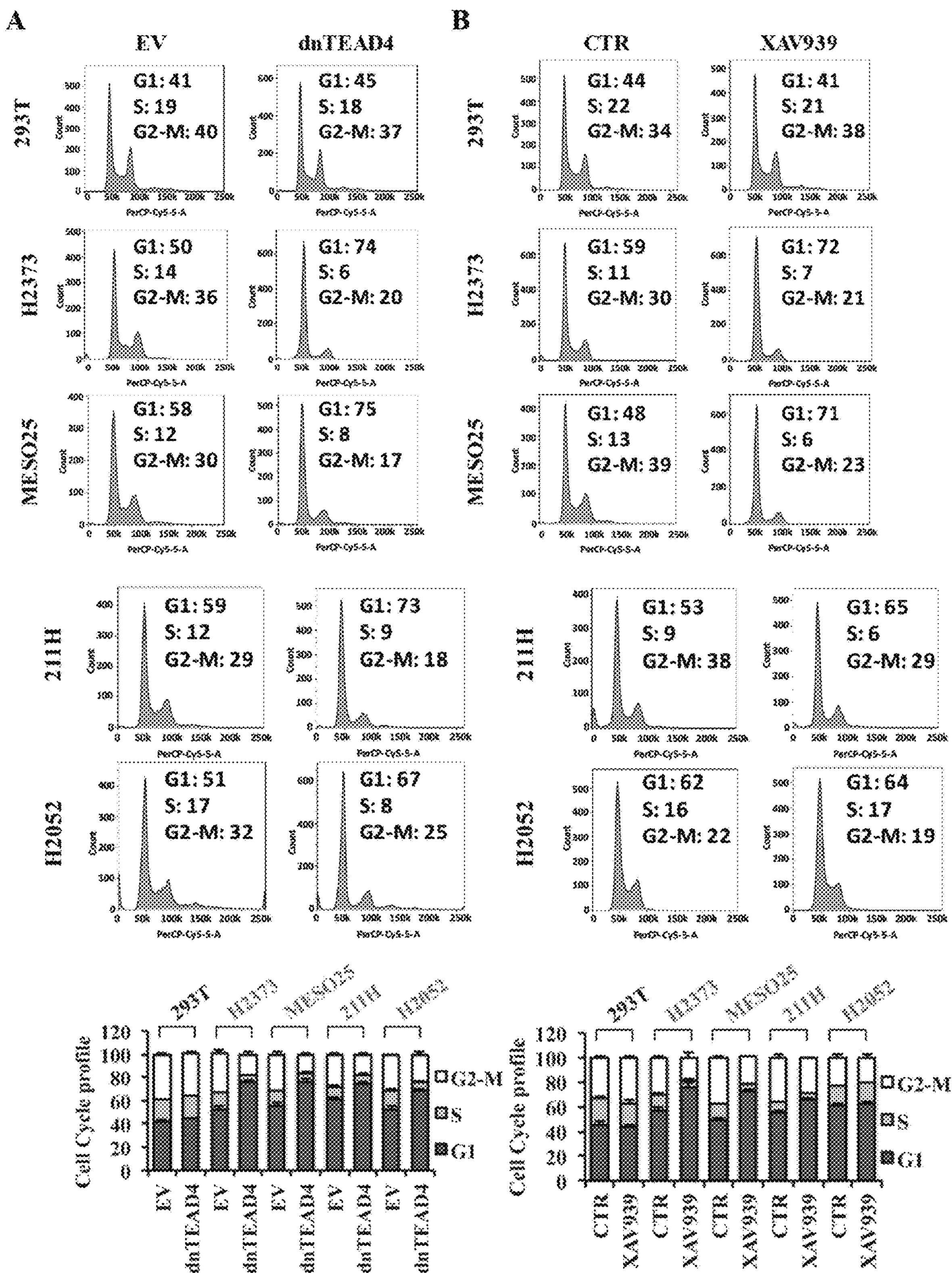
FIGs. 5A-B

FIGs. 6A-H
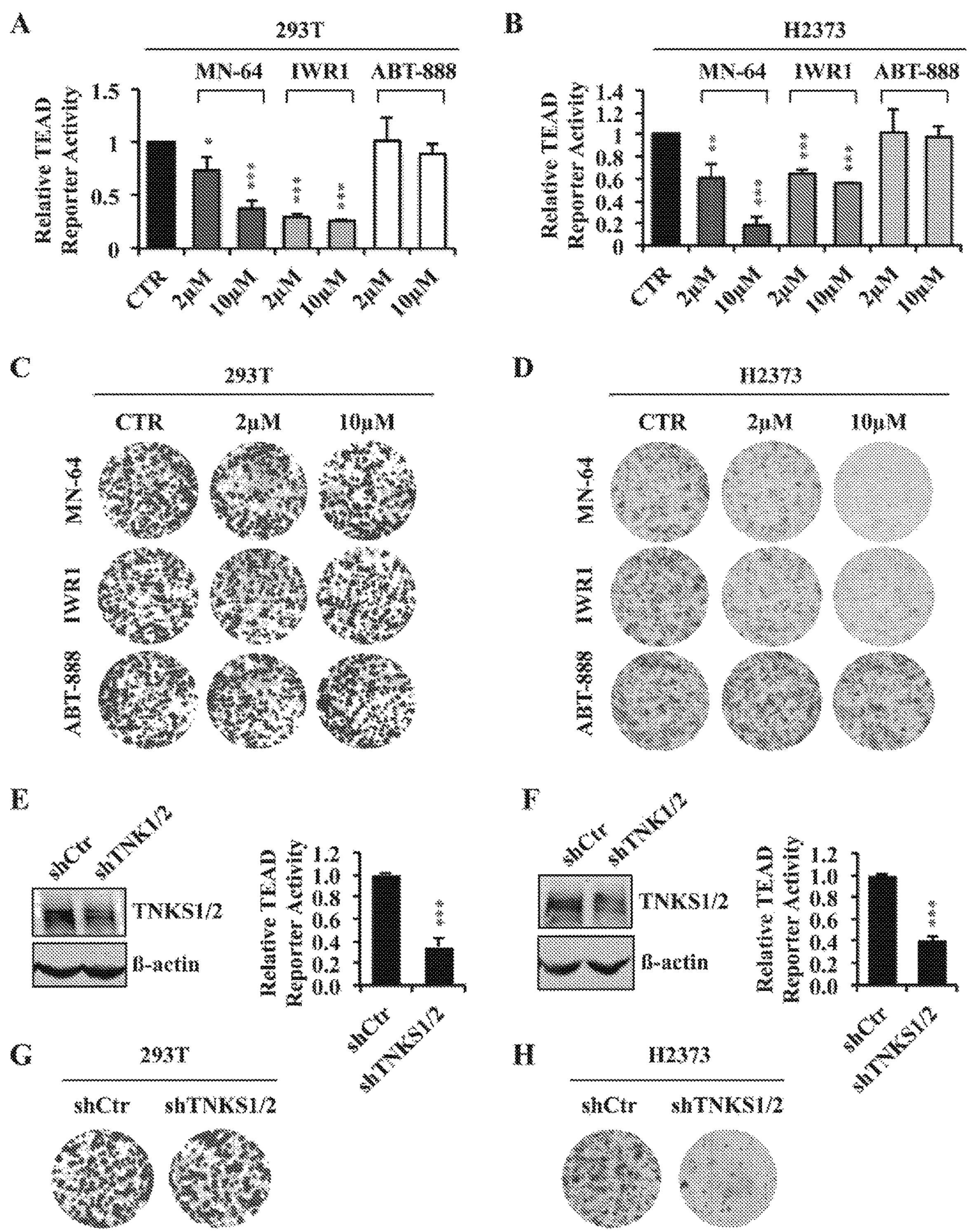

FIGs. 7A-H
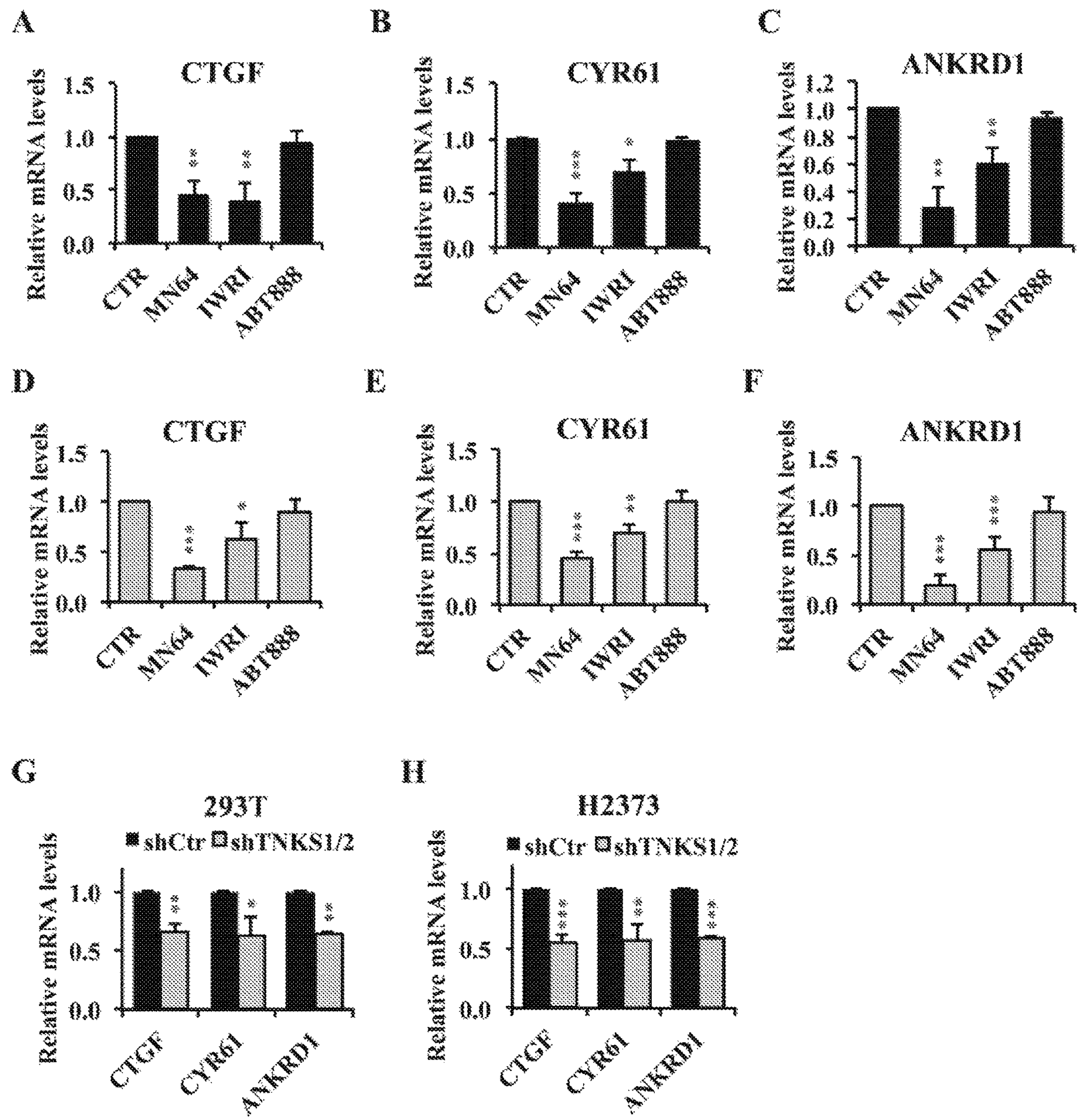

FIGs. 8A-F
A
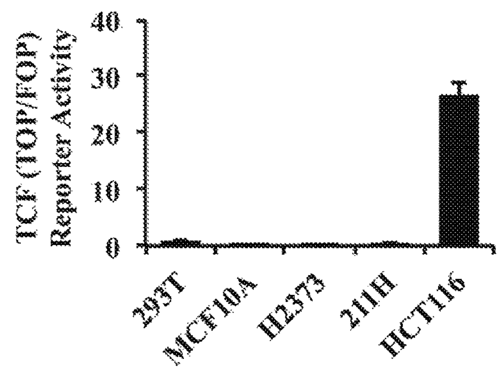
B
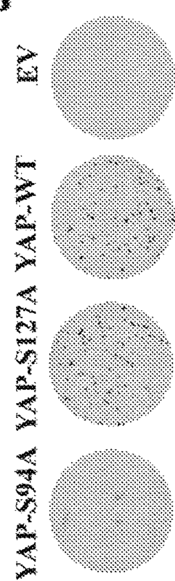
C
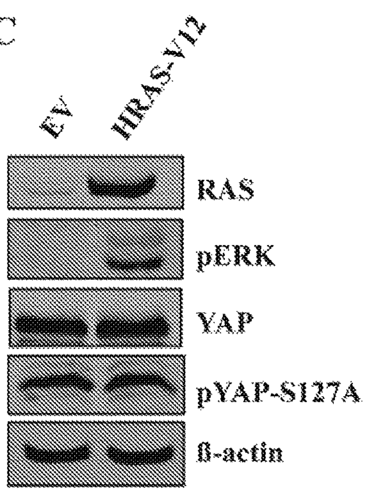
D
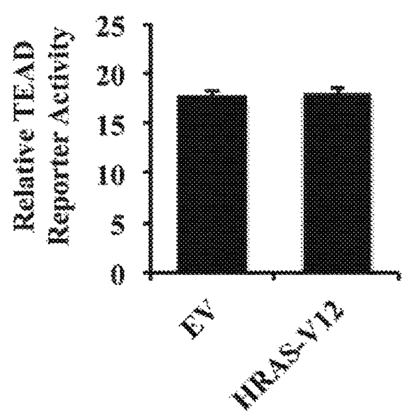
E
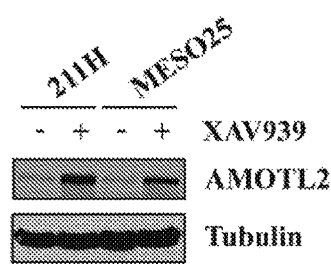
F
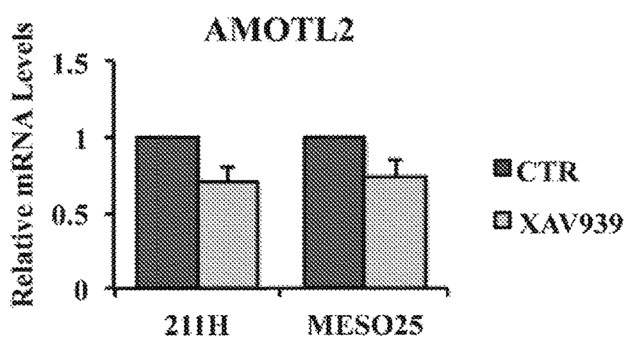

FIGs. 9A-E
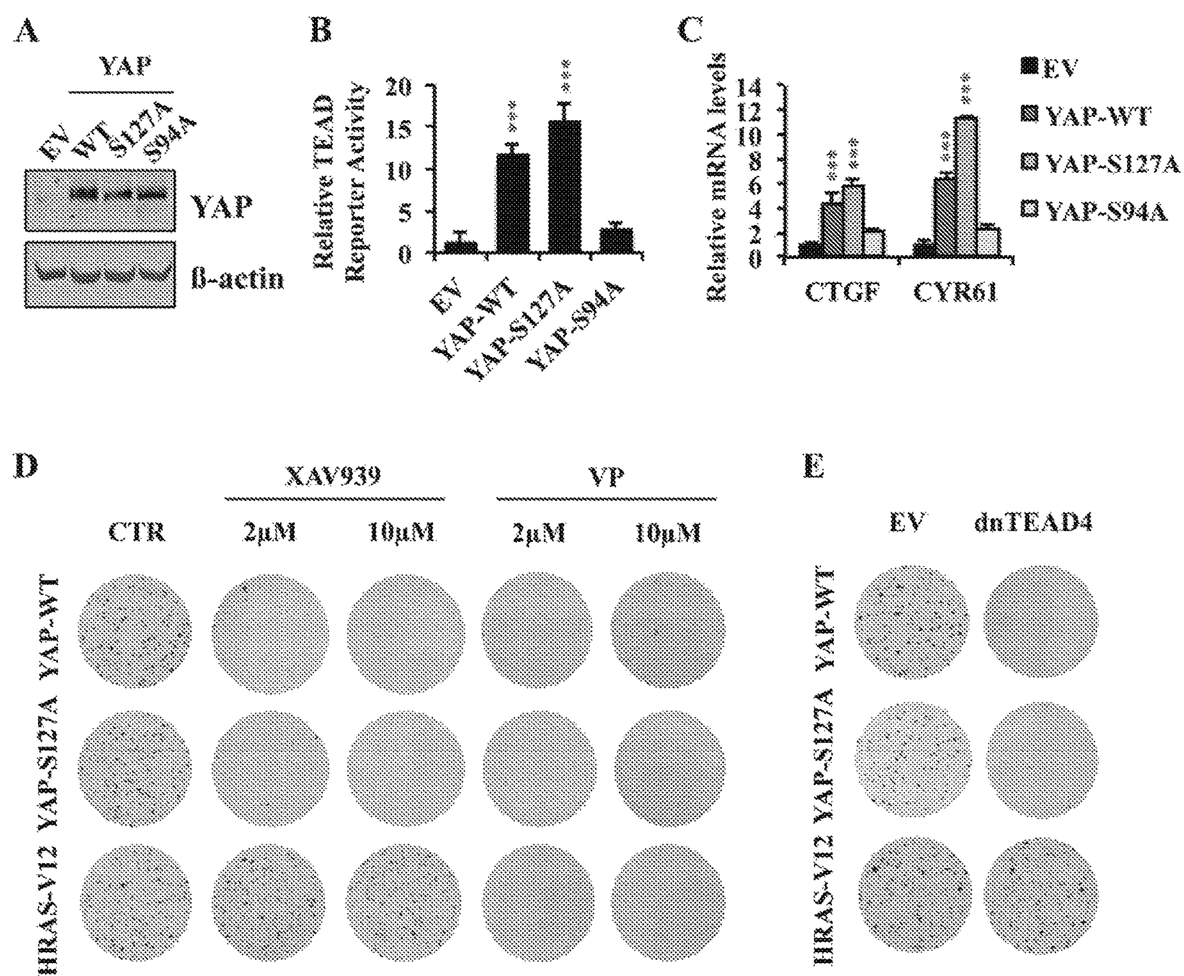

FIGs. 10A-F
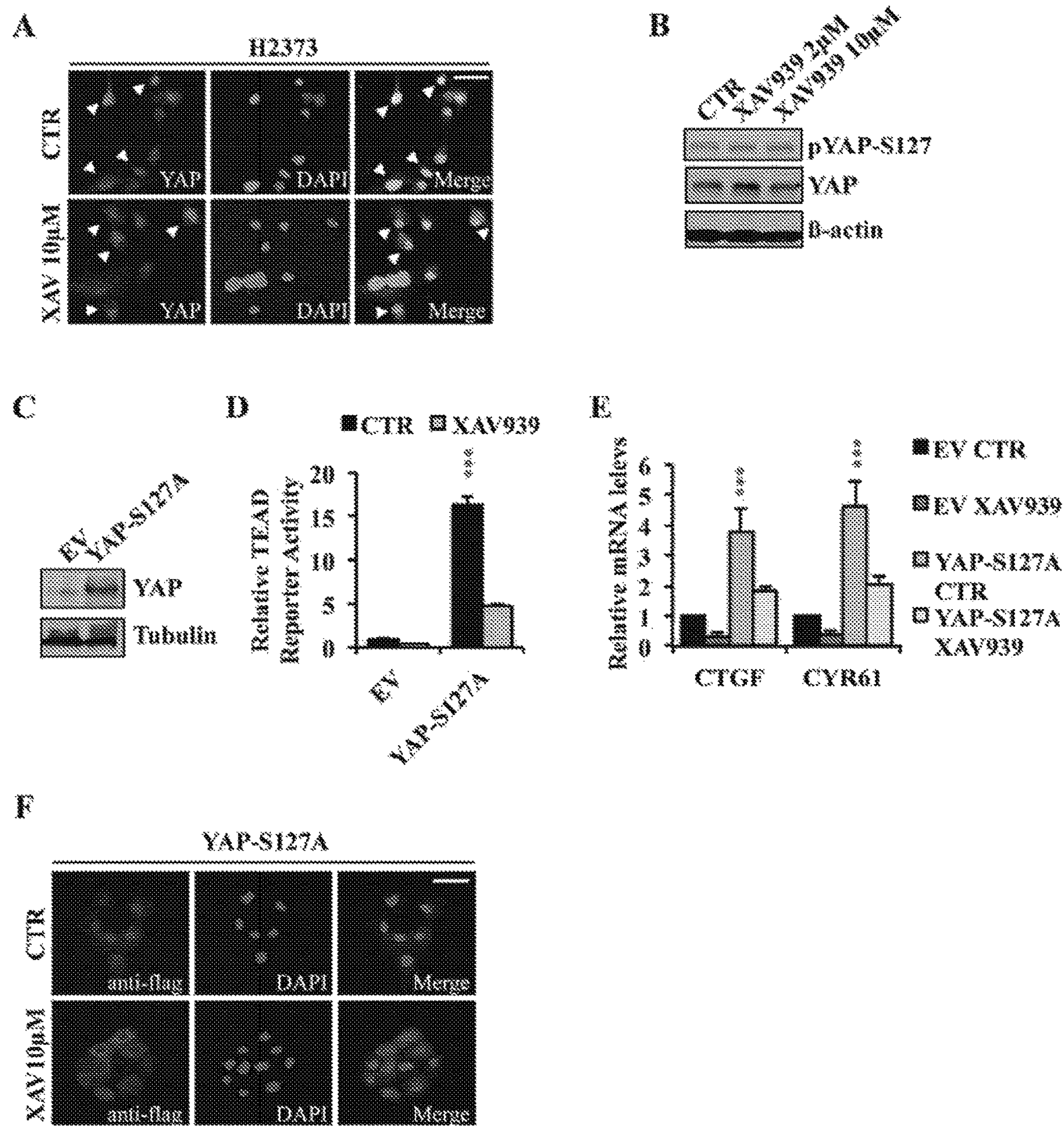

FIGs. 11A-I
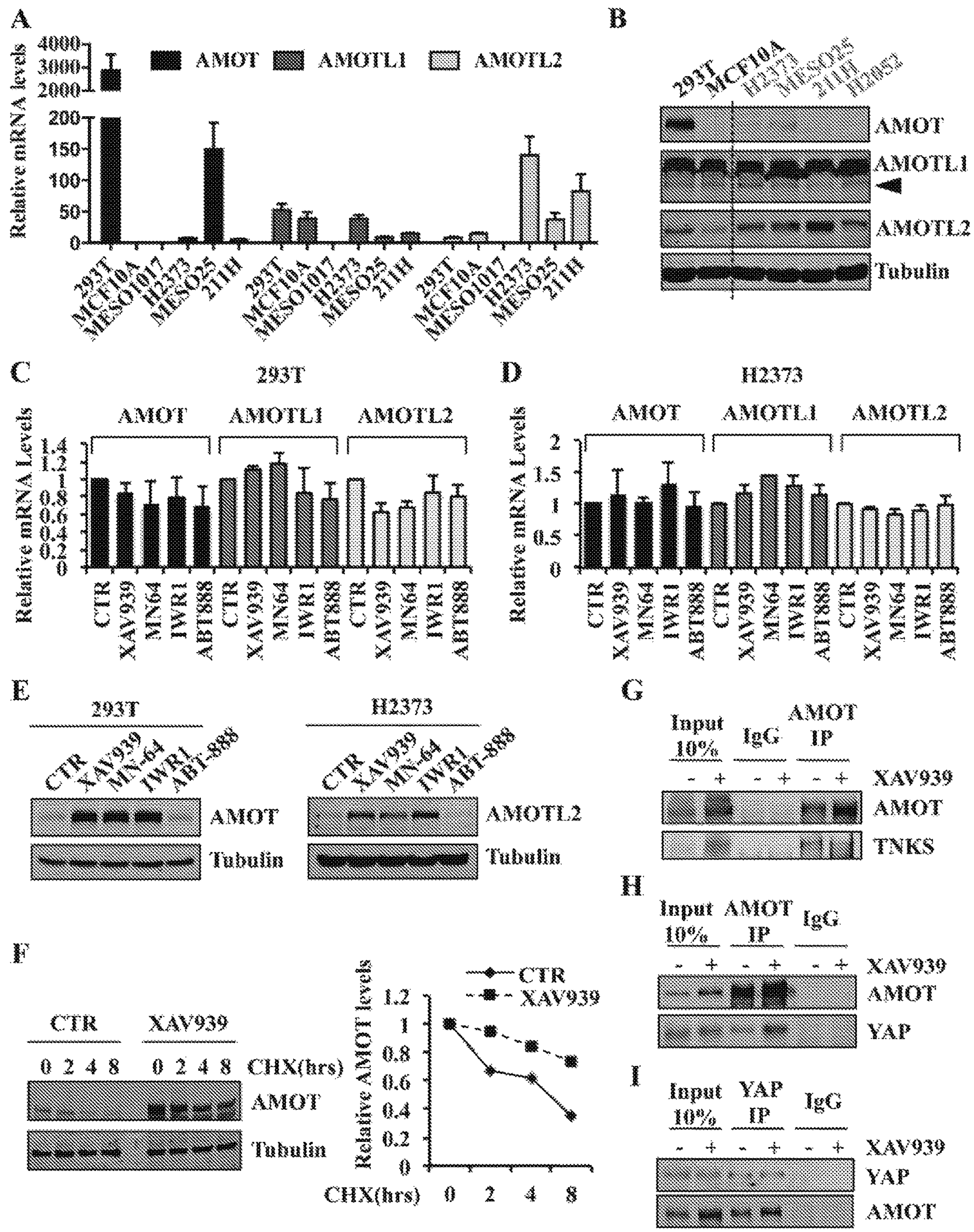

FIGs. 12A-J
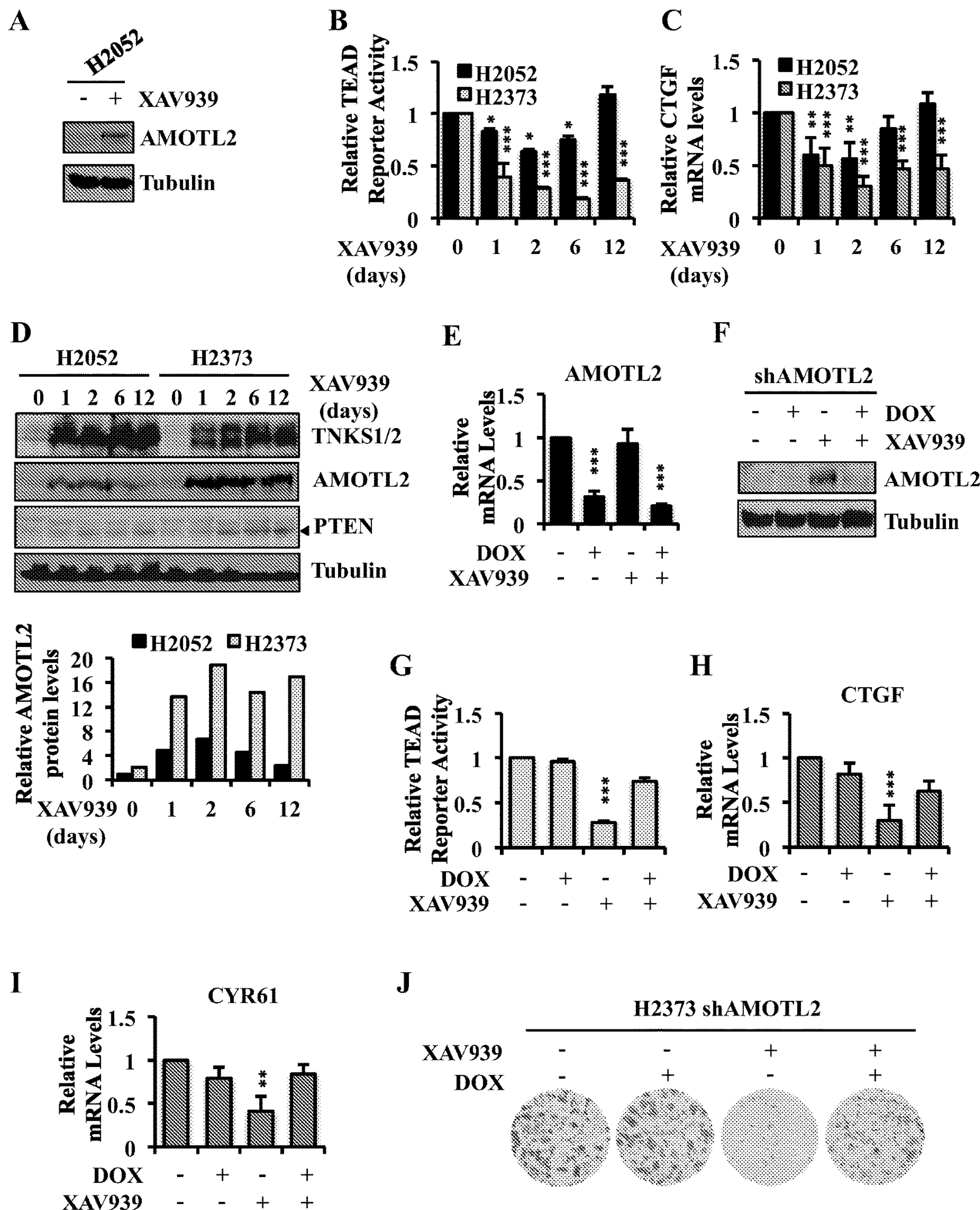

FIGs. 13A-B
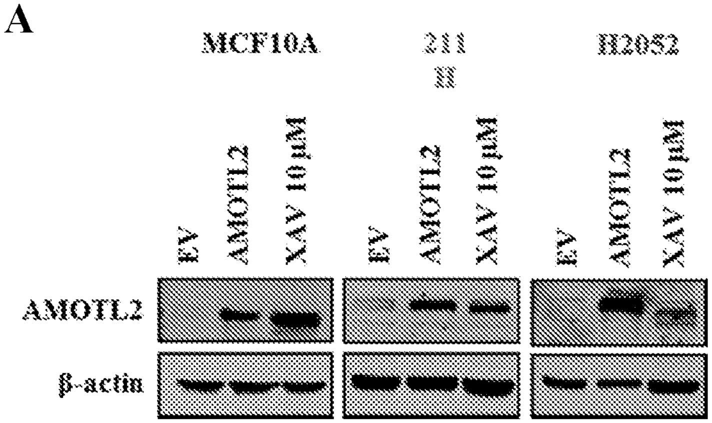
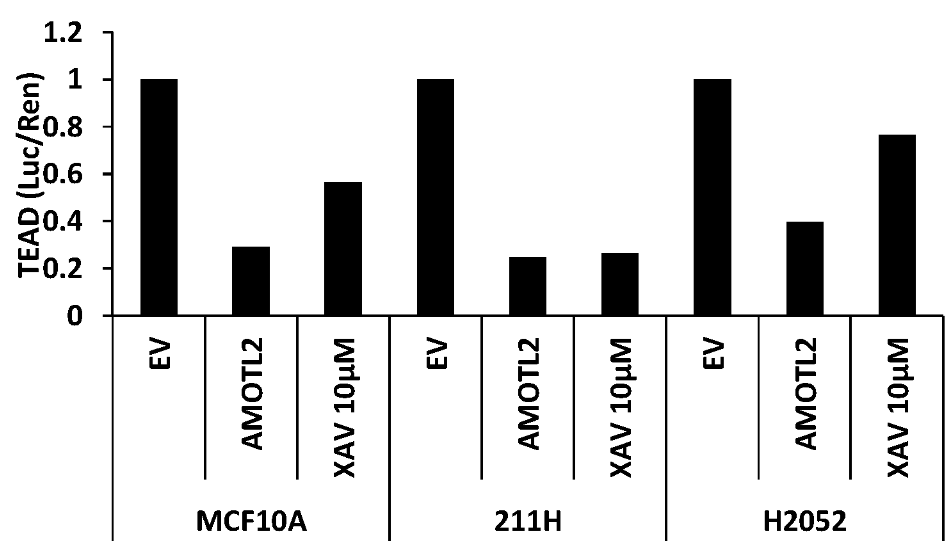

FIGs. 13C-D
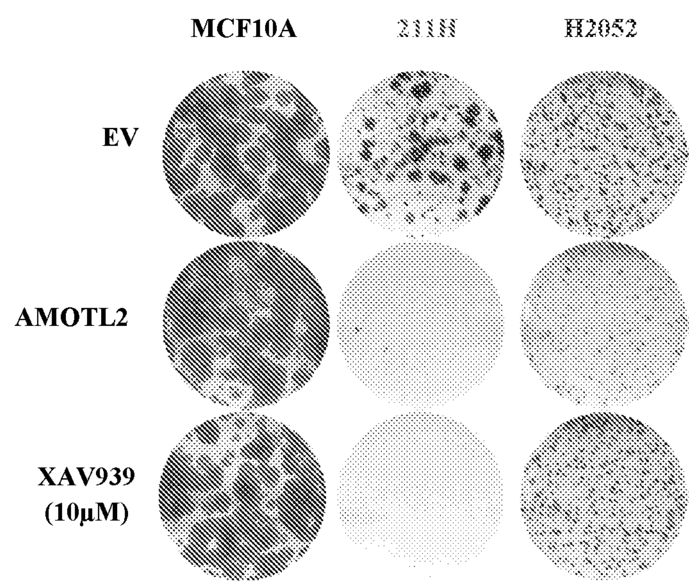
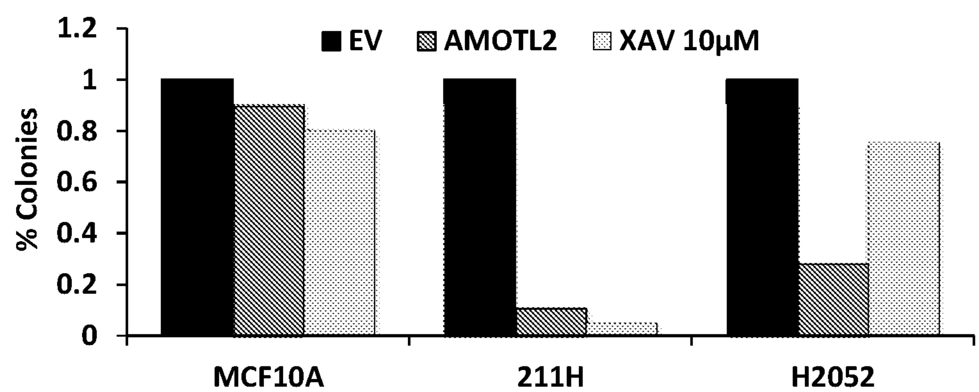

FIGs. 14A-D
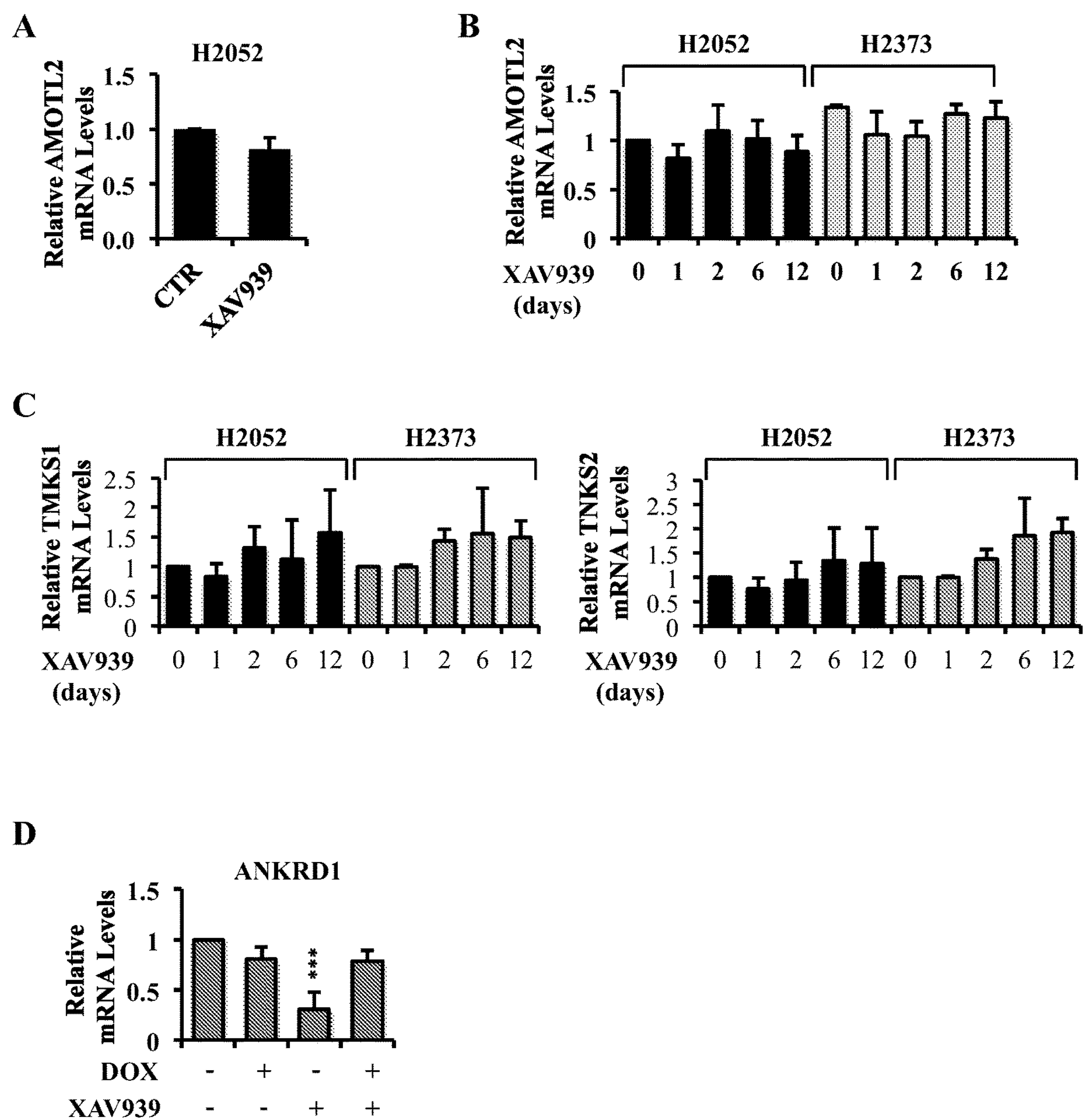

SEQUENCE LISTING

<160> NUMBER OF SEQ ID NOS: 49

<210> SEQ ID NO 1
<211> LENGTH: 7533
<212> TYPE: DNA
<213> ORGANISM: Homo sapiens

<400> SEQUENCE: 1

```
gcgacgctca cgaacgatca gagctgcggg cgacgcaacg aagcccggag gccgcaggct     60

gcgcgctccc tcgcagcagc cgggcgggca aaagccccca gtcctcggcc cccgcgcaag    120

cgacgccggg aaatgcccac atccgggaaa cctgcagcgg agtgcggcgg cggcgacact    180

gagtggaagg caaaatggcg gcggcggcgg cggtggcctg gtgttaaggg gagagccagg    240

tcctcacgac ccctgggacg ggccgcgctg gcccgcggca gcccccccgt tcgtctcccc    300

gctctgcccc accagggata cttggggttg ctgggacgga ctctggccgc ctcagcgtcc    360

gccctcaggc ccgtggccgc tgtccaggag ctctgctctc ccctccagag ttaattattt    420

atattgtaaa gaattttaac agtcctgggg acttccttga aggatcattt tcacttttgc    480

tcagaagaaa gctctggatc tatcaaataa agaagtcctt cgtgtgggct acatatatag    540

atgttttcat gaagaggagt gaaaagccag aaggatatag acaaatgagg cctaagacct    600

ttcctgccag taactatact gtcagtagcc ggcaaatgtt acaagaaatt cgggaatccc    660

ttaggaattt atctaaacca tctgatgctg ctaaggctga gcataacatg agtaaaatgt    720

caaccgaaga tcctcgacaa gtcagaaatc cacccaaatt tgggacgcat cataaagcct    780

tgcaggaaat tcgaaactct ctgcttccat ttgcaaatga aacaaattct tctcggagta    840

cttcagaagt taatccacaa atgcttcaag acttgcaagc tgctggattt gatgaggata    900

tggttataca agctcttcag aaaactaaca acagaagtat agaagcagca attgaattca    960

ttagtaaaat gagttaccaa gatcctcgac gagagcagat ggctgcagca gctgccagac   1020

ctattaatgc cagcatgaaa ccagggaatg tgcagcaatc agttaaccgc aaacagagct   1080

ggaaaggttc taaagaatcc ttagttcctc agaggcatgg cccgccacta ggagaaagtg   1140

tggcctatca ttctgagagt cccaactcac agacagatgt aggaagacct ttgtctggat   1200

ctggtatatc agcatttgtt caagctcacc ctagcaacgg acagagagtg aacccccccac  1260

caccacctca agtaaggagt gttactcctc caccacctcc aagaggccag actccccctc   1320

caagaggtac aactccacct ccccccttcat gggaaccaaa ctctcaaaca aagcgctatt  1380

ctggaaacat ggaatacgta atctcccgaa tctctcctgt cccacctggg gcatggcaag   1440

agggctatcc tccaccacct ctcaacactt cccccatgaa tcctcctaat caaggacaga   1500

gaggcattag ttctgttcct gttggcagac aaccaatcat catgcagagt tctagcaaat   1560

ttaactttcc atcagggaga cctggaatgc agaatggtac tggacaaact gatttcatga   1620

tacaccaaaa tgttgtccct gctggcactg tgaatcggca gccaccacct ccatatcctc   1680

tgacagcagc taatggacaa agcccttctg ctttacaaac agggggatct gctgctcctt   1740

cgtcatatac aaatggaagt attcctcagt ctatgatggt gccaaacaga aatagtcata   1800

acatggaact atataacatt agtgtacctg gactgcaaac aaattggcct cagtcatctt   1860

ctgctccagc ccagtcatcc ccgagcagtg ggcatgaaat ccctacatgg caacctaaca   1920

taccagtgag gtcaaattct tttaataacc cattaggaaa tagagcaagt cactctgcta   1980

attctcagcc ttctgctaca acagtcactg caattacacc agctcctatt caacagcctg   2040

tgaaaagtat gcgtgtatta aaaccagagc tacagactgc tttagcacct acacaccctt   2100
```

```
cttggatacc acagccaatt caaactgttc aacccagtcc ttttcctgag ggaaccgctt   2160

caaatgtgac tgtgatgcca cctgttgctg aagctccaaa ctatcaagga ccaccaccac   2220

cctacccaaa acatctgctg caccaaaacc catctgttcc tccatacgag tcaatcagta   2280

agcctagcaa agaggatcag ccaagcttgc ccaaggaaga tgagagtgaa aagagttatg   2340

aaaatgttga tagtggggat aaagaaaaga aacagattac aacttcacct attactgtta   2400

ggaaaaacaa gaaagatgaa gagcgaaggg aatctcgtat tcaaagttat tctcctcaag   2460

catttaaatt ctttatggag caacatgtag aaaatgtact caaatctcat cagcagcgtc   2520

tacatcgtaa aaaacaatta gagaatgaaa tgatgcgggt tggattatct caagatgccc   2580

aggatcaaat gagaaagatg ctttgccaaa aagaatctaa ttacatccgt cttaaaaggg   2640

ctaaaatgga caagtctatg tttgtgaaga taaagacact aggaatagga gcatttggtg   2700

aagtctgtct agcaagaaaa gtagatacta aggctttgta tgcaacaaaa actcttcgaa   2760

agaaagatgt tcttcttcga aatcaagtcg ctcatgttaa ggctgagaga gatatcctgg   2820

ctgaagctga caatgaatgg gtagttcgtc tatattattc attccaagat aaggacaatt   2880

tatactttgt aatggactac attcctgggg gtgatatgat gagcctatta attagaatgg   2940

gcatctttcc agaaagtctg gcacgattct acatagcaga acttacctgt gcagttgaaa   3000

gtgttcataa aatgggtttt attcatagag atattaaacc tgataatatt ttgattgatc   3060

gtgatggtca tattaaattg actgactttg gcctctgcac tggcttcaga tggacacacg   3120

attctaagta ctatcagagt ggtgaccatc cacggcaaga tagcatggat ttcagtaatg   3180

aatgggggga tccctcaagc tgtcgatgtg gagacagact gaagccatta gagcggagag   3240

ctgcacgcca gcaccagcga tgtctagcac attctttggt tgggactccc aattatattg   3300

cacctgaagt gttgctacga acaggataca cacagttgtg tgattggtgg agtgttggtg   3360

ttattctttt tgaaatgttg gtgggacaac ctcctttctt ggcacaaaca ccattagaaa   3420

cacaaatgaa ggttatcaac tggcaaacat ctcttcacat tccaccacaa gctaaactca   3480

gtcctgaagc ttctgatctt attattaaac tttgccgagg acccgaagat cgcttaggca   3540

agaatggtgc tgatgaaata aaagctcatc catttttaa aacaattgac ttctccagtg   3600

acctgagaca gcagtctgct tcatacattc ctaaaatcac acacccaaca gatacatcaa   3660

attttgatcc tgttgatcct gataaattat ggagtgatga taacgaggaa gaaaatgtaa   3720

atgacactct caatggatgg tataaaaatg gaaagcatcc tgaacatgca ttctatgaat   3780

ttaccttccg aaggtttttt gatgacaatg gctacccata taattatccg aagcctattg   3840

aatatgaata cattaattca caaggctcag agcagcagtc ggatgaagat gatcaaaaca   3900

caggctcaga gattaaaaat cgcgatctag tatatgttta acacactagt aaataaatgt   3960

aatgaggatt tgtaaaaggg cctgaaatgc gaggtgtttt gaggttctga gagtaaaatt   4020

atgcaaatat gacagagcta tatatgtgtg ctctgtgtac aatattttat tttcctaaat   4080

tatgggaaat ccttttaaaa tgttaattta ttccagccgt ttaaatcagt atttagaaaa   4140

aaattgttat aaggaaagta aattatgaac tgaatattat agtcagttct tggtacttaa   4200

agtacttaaa ataagtagtg ctttgtttaa aaggagaaac ctggtatcta tttgtatata   4260

tgctaaataa ttttaaaata caagagtttt tgaaattttt ttgaaagaca gttttagttt   4320

tatcttgctt taaccaaata tgaaacatac cccctatttt acagagctct tttttcccct   4380

cataaccttg tttttggtag aaaataagct agagaaatta agccatcgtg ttggtgagtg   4440
```

```
ttcctaggct aatgataatc tgtataattc acatcctgaa actaaggaat acagggttga   4500
aaaaatatta atatgtttgt cagaaggaaa aataatgcat ttatcttccc ccccaccccc   4560
cgccccatgg aatatttaat ctatttaatc ttcttgcatt tatttctcaa gaattactgg   4620
ctttaaaaga agccaaagca ctactagctt tttttccata ttggtatttt tgatgctgct   4680
tccaatttta aaagggaaca aagctgccat aaatcgaaat gttcaatact aaaagctaaa   4740
atatttctca ccatcctaag cagataatta ttttaatttt catatacttt tcctgtatag   4800
taactatttt gattatatca tcaatgttac ctgtttcctc tttcagaaca gtgctgcata   4860
tacagattgt tattggcaaa ggaaaatctg gctatctggc aatattttac ctaagcgcag   4920
attaattggt gaaaaaatta actcttaaga tggccattaa taattaggaa agtttacaga   4980
gtggtcttag tagaaaattc aagtcctcct aatttattta aggttcaata atgcgttcaa   5040
catgcctgtt atgtataacg cttaggttct aaggaagatt aaggtttcat accaaaatac   5100
atgtagctta tcttttagga aggggaaaaa ggctccattt tgaccatagt aaaatttgtg   5160
ttgtgtttta tttccttttc ttaagctcca ctgataaggg attgttttta tcaaaagtta   5220
ctatttgtag attggaggca taattttagt gattttcata cttttagctt tcttcgcata   5280
aaagctaatt gaaaccgtat atgtagtaaa attaaaggca gagctgttgc agttgaattg   5340
gagagttagg gcaaagaaca cttattagcc cacacttccc acctttctac aggtggtcct   5400
ttcagagctc agcctgaaaa cccactactg tgttatcgtg cgtcttttgg ggttagtggt   5460
tcttttgaga atctgaagga agctgtggac tcttcctaga aaaaaaaacc acacatacac   5520
atacaatgtt gcatgcagtt tcaagggatt ttggacatat tgaaacctat cacaggctgt   5580
aggttatgga cctctgtgcc atgagaaaat tgatacatta aactaagaac tttgttttta   5640
acttaccaat cactactcag cacatcttat ataagctgat aatttgtgat ggaaaaggtc   5700
tgtagcatgt gatataaggt gaccttatga atgcctctct tgctggtaca ttaagttgtt   5760
ttaatatatc atttggaggg gactgaaatg ttaggctcat tacaagcttg atacagaaat   5820
atttctgaag gatttctaat cagaattgta aaacaatgtg ctatcatgaa atcgcagtct   5880
tcacctcatg gttcatggaa catttggtta gtcccataaa atcctatgca aaacaaagta   5940
gttcaagaat ttttaggtgg gtagtcacat ttataaggta ttcctcttac tctttgggct   6000
ttttcagtct gatttattta aattttcatt tagttgtttt acttttggac taaggtgcaa   6060
tacagtagaa gataactttg ttacatttat gttgtaggaa aactaaggtg ctgtctcctc   6120
ccccttccct tcccacaaaa tctgtattcc ccctattgct gaaatgtaac agacactaca   6180
aattttgtat tctttttttg tttttgtttt tgagacaggg tctcactctg tcacccaggc   6240
tggagggcag tggcgcttca cagctcactg catcctcaac cttgggggct cacgcagtcc   6300
tcccgcctca gcctcccaag tagctgggca tgcgccacca agcccagcta atttttgtat   6360
ctttagtaga gatggggttt cgccatgttg cccaggttgg tgtggaattc ctgggctcca   6420
gttatatgcc cacctcagcc tcccaaagtg ctgggattac agacgtgacc caccgcgcct   6480
ggcgcaaata tgtattcttt taaaatttcc tctgatacta taagcttttt gcatttatct   6540
gaagcagtat acatgccttt ggtatcagca attttaacag tttggatata cttatcagct   6600
atcttattcc aaaactacat ctacttcttc cagtatagaa tctggtgctt cctgaccaaa   6660
aagatgagaa aaacaatgtt aaaaatatag atgctttcca ttgaaatgga gtgaaaacat   6720
tggttctata tgttttcttt taaaataatt ttcttattaa aaacttgctg tctttattat   6780
acttaccctt tttatgcata tcaatagtat ttataagatg tgttctataa ttatgtaatt   6840
```

```
gtagatactg ttatgcattg tccagtgaca tcataaggca ggccctactg ctgtatcttt   6900

tctaccttct tatttgtaat agaaactata gaatgtatga ctaaaaagtc actttgagat   6960

tgactttttt aaaaagttat taccttctgc tgttgcaaag tgcaaaactg tgagtggaat   7020

tgttttattc tgacttaatg tgttagaaat tagagaatac agtgggagga tttttagaca   7080

ttgctgctgc tgttacccaa ggtattttag ataaaaaatt tttaataaac atccctttgg   7140

tatttaaagt ggaacattta gcctgttcat tttaatctaa agcaaaaagt aatttgggtc   7200

aaaatattgg tatatttgta aagcgcctta atatatccct ttgtggaagg cactacacag   7260

tttactttta tattgtattg tgtatataag tattttgtat taaaattgaa tcagtggcaa   7320

cattaaagtt ttataaaatc atgctttgtt agaaaaagaa ttacagcttt gcaatataac   7380

taattgtttc gcataattct gaatgtaata gatatgaata atcagcctgt gtttttaatg   7440

aacttatttg tattttccca atcattttct ctagtgtaat gtttgctggg ataataaaaa   7500

aaattcaaat ctttcaaaaa aaaaaaaaaa aaa                                  7533
```

```
<210> SEQ ID NO 2
<211> LENGTH: 1130
<212> TYPE: PRT
<213> ORGANISM: Homo sapiens

<400> SEQUENCE: 2

Met Lys Arg Ser Glu Lys Pro Glu Gly Tyr Arg Gln Met Arg Pro Lys
1               5                   10                  15

Thr Phe Pro Ala Ser Asn Tyr Thr Val Ser Ser Arg Gln Met Leu Gln
            20                  25                  30

Glu Ile Arg Glu Ser Leu Arg Asn Leu Ser Lys Pro Ser Asp Ala Ala
        35                  40                  45

Lys Ala Glu His Asn Met Ser Lys Met Ser Thr Glu Asp Pro Arg Gln
    50                  55                  60

Val Arg Asn Pro Pro Lys Phe Gly Thr His His Lys Ala Leu Gln Glu
65                  70                  75                  80

Ile Arg Asn Ser Leu Leu Pro Phe Ala Asn Glu Thr Asn Ser Ser Arg
                85                  90                  95

Ser Thr Ser Glu Val Asn Pro Gln Met Leu Gln Asp Leu Gln Ala Ala
            100                 105                 110

Gly Phe Asp Glu Asp Met Val Ile Gln Ala Leu Gln Lys Thr Asn Asn
        115                 120                 125

Arg Ser Ile Glu Ala Ala Ile Glu Phe Ile Ser Lys Met Ser Tyr Gln
    130                 135                 140

Asp Pro Arg Arg Glu Gln Met Ala Ala Ala Ala Ala Arg Pro Ile Asn
145                 150                 155                 160

Ala Ser Met Lys Pro Gly Asn Val Gln Gln Ser Val Asn Arg Lys Gln
                165                 170                 175

Ser Trp Lys Gly Ser Lys Glu Ser Leu Val Pro Gln Arg His Gly Pro
            180                 185                 190

Pro Leu Gly Glu Ser Val Ala Tyr His Ser Glu Ser Pro Asn Ser Gln
        195                 200                 205

Thr Asp Val Gly Arg Pro Leu Ser Gly Ser Gly Ile Ser Ala Phe Val
    210                 215                 220

Gln Ala His Pro Ser Asn Gly Gln Arg Val Asn Pro Pro Pro Pro Pro
225                 230                 235                 240

Gln Val Arg Ser Val Thr Pro Pro Pro Pro Pro Arg Gly Gln Thr Pro
```

-continued

```
                245                 250                 255

Pro Pro Arg Gly Thr Thr Pro Pro Pro Pro Ser Trp Glu Pro Asn Ser
            260                 265                 270

Gln Thr Lys Arg Tyr Ser Gly Asn Met Glu Tyr Val Ile Ser Arg Ile
        275                 280                 285

Ser Pro Val Pro Pro Gly Ala Trp Gln Glu Gly Tyr Pro Pro Pro Pro
    290                 295                 300

Leu Asn Thr Ser Pro Met Asn Pro Pro Asn Gln Gly Gln Arg Gly Ile
305                 310                 315                 320

Ser Ser Val Pro Val Gly Arg Gln Pro Ile Ile Met Gln Ser Ser Ser
                325                 330                 335

Lys Phe Asn Phe Pro Ser Gly Arg Pro Gly Met Gln Asn Gly Thr Gly
            340                 345                 350

Gln Thr Asp Phe Met Ile His Gln Asn Val Val Pro Ala Gly Thr Val
        355                 360                 365

Asn Arg Gln Pro Pro Pro Pro Tyr Pro Leu Thr Ala Ala Asn Gly Gln
    370                 375                 380

Ser Pro Ser Ala Leu Gln Thr Gly Gly Ser Ala Ala Pro Ser Ser Tyr
385                 390                 395                 400

Thr Asn Gly Ser Ile Pro Gln Ser Met Met Val Pro Asn Arg Asn Ser
                405                 410                 415

His Asn Met Glu Leu Tyr Asn Ile Ser Val Pro Gly Leu Gln Thr Asn
            420                 425                 430

Trp Pro Gln Ser Ser Ser Ala Pro Ala Gln Ser Ser Pro Ser Ser Gly
        435                 440                 445

His Glu Ile Pro Thr Trp Gln Pro Asn Ile Pro Val Arg Ser Asn Ser
    450                 455                 460

Phe Asn Asn Pro Leu Gly Asn Arg Ala Ser His Ser Ala Asn Ser Gln
465                 470                 475                 480

Pro Ser Ala Thr Thr Val Thr Ala Ile Thr Pro Ala Pro Ile Gln Gln
                485                 490                 495

Pro Val Lys Ser Met Arg Val Leu Lys Pro Glu Leu Gln Thr Ala Leu
            500                 505                 510

Ala Pro Thr His Pro Ser Trp Ile Pro Gln Pro Ile Gln Thr Val Gln
        515                 520                 525

Pro Ser Pro Phe Pro Glu Gly Thr Ala Ser Asn Val Thr Val Met Pro
    530                 535                 540

Pro Val Ala Glu Ala Pro Asn Tyr Gln Gly Pro Pro Pro Pro Tyr Pro
545                 550                 555                 560

Lys His Leu Leu His Gln Asn Pro Ser Val Pro Pro Tyr Glu Ser Ile
                565                 570                 575

Ser Lys Pro Ser Lys Glu Asp Gln Pro Ser Leu Pro Lys Glu Asp Glu
            580                 585                 590

Ser Glu Lys Ser Tyr Glu Asn Val Asp Ser Gly Asp Lys Glu Lys Lys
        595                 600                 605

Gln Ile Thr Thr Ser Pro Ile Thr Val Arg Lys Asn Lys Lys Asp Glu
    610                 615                 620

Glu Arg Arg Glu Ser Arg Ile Gln Ser Tyr Ser Pro Gln Ala Phe Lys
625                 630                 635                 640

Phe Phe Met Glu Gln His Val Glu Asn Val Leu Lys Ser His Gln Gln
                645                 650                 655

Arg Leu His Arg Lys Lys Gln Leu Glu Asn Glu Met Met Arg Val Gly
            660                 665                 670
```

```
Leu Ser Gln Asp Ala Gln Asp Gln Met Arg Lys Met Leu Cys Gln Lys
        675                 680                 685

Glu Ser Asn Tyr Ile Arg Leu Lys Arg Ala Lys Met Asp Lys Ser Met
    690                 695                 700

Phe Val Lys Ile Lys Thr Leu Gly Ile Gly Ala Phe Gly Glu Val Cys
705                 710                 715                 720

Leu Ala Arg Lys Val Asp Thr Lys Ala Leu Tyr Ala Thr Lys Thr Leu
                725                 730                 735

Arg Lys Lys Asp Val Leu Leu Arg Asn Gln Val Ala His Val Lys Ala
            740                 745                 750

Glu Arg Asp Ile Leu Ala Glu Ala Asp Asn Glu Trp Val Val Arg Leu
        755                 760                 765

Tyr Tyr Ser Phe Gln Asp Lys Asp Asn Leu Tyr Phe Val Met Asp Tyr
    770                 775                 780

Ile Pro Gly Gly Asp Met Met Ser Leu Leu Ile Arg Met Gly Ile Phe
785                 790                 795                 800

Pro Glu Ser Leu Ala Arg Phe Tyr Ile Ala Glu Leu Thr Cys Ala Val
                805                 810                 815

Glu Ser Val His Lys Met Gly Phe Ile His Arg Asp Ile Lys Pro Asp
            820                 825                 830

Asn Ile Leu Ile Asp Arg Asp Gly His Ile Lys Leu Thr Asp Phe Gly
        835                 840                 845

Leu Cys Thr Gly Phe Arg Trp Thr His Asp Ser Lys Tyr Tyr Gln Ser
    850                 855                 860

Gly Asp His Pro Arg Gln Asp Ser Met Asp Phe Ser Asn Glu Trp Gly
865                 870                 875                 880

Asp Pro Ser Ser Cys Arg Cys Gly Asp Arg Leu Lys Pro Leu Glu Arg
                885                 890                 895

Arg Ala Ala Arg Gln His Gln Arg Cys Leu Ala His Ser Leu Val Gly
            900                 905                 910

Thr Pro Asn Tyr Ile Ala Pro Glu Val Leu Leu Arg Thr Gly Tyr Thr
        915                 920                 925

Gln Leu Cys Asp Trp Trp Ser Val Gly Val Ile Leu Phe Glu Met Leu
    930                 935                 940

Val Gly Gln Pro Pro Phe Leu Ala Gln Thr Pro Leu Glu Thr Gln Met
945                 950                 955                 960

Lys Val Ile Asn Trp Gln Thr Ser Leu His Ile Pro Pro Gln Ala Lys
                965                 970                 975

Leu Ser Pro Glu Ala Ser Asp Leu Ile Ile Lys Leu Cys Arg Gly Pro
            980                 985                 990

Glu Asp Arg Leu Gly Lys Asn Gly  Ala Asp Glu Ile Lys  Ala His Pro
        995                 1000                 1005

Phe Phe  Lys Thr Ile Asp Phe  Ser Ser Asp Leu Arg  Gln Gln Ser
    1010                 1015                 1020

Ala Ser  Tyr Ile Pro Lys Ile  Thr His Pro Thr Asp  Thr Ser Asn
    1025                 1030                 1035

Phe Asp  Pro Val Asp Pro Asp  Lys Leu Trp Ser Asp  Asp Asn Glu
    1040                 1045                 1050

Glu Glu  Asn Val Asn Asp Thr  Leu Asn Gly Trp Tyr  Lys Asn Gly
    1055                 1060                 1065

Lys His  Pro Glu His Ala Phe  Tyr Glu Phe Thr Phe  Arg Arg Phe
    1070                 1075                 1080
```

```
Phe Asp  Asp Asn Gly Tyr Pro  Tyr Asn Tyr Pro Lys  Pro Ile Glu
    1085                 1090                 1095

Tyr Glu  Tyr Ile Asn Ser Gln  Gly Ser Glu Gln Gln  Ser Asp Glu
    1100                 1105                 1110

Asp Asp  Gln Asn Thr Gly Ser  Glu Ile Lys Asn Arg  Asp Leu Val
    1115                 1120                 1125

Tyr Val
    1130


<210> SEQ ID NO 3
<211> LENGTH: 5558
<212> TYPE: DNA
<213> ORGANISM: Homo sapiens

<400> SEQUENCE: 3

gcccgtggaa tgccaacaat gtagcgaatg tcccacttgg gtctgcgctt tggaaccgcg     60

gcgtgagcgc cccgggaaga tggagcagtc gccgtccacg ccaccgccgc cgcccggggc    120

tccccgtcc ctgcggggcc agcagcagct ccagccacca gtgcccggtc tcccggcgcg    180

agaggcccgg gagccgccgg ccaggacgcc cccgagggtg tagaccgcgc ccctggagag    240

agtgataatc ttcaaaatga agactttgga aaattttagg ttctctatag gaactacaaa    300

aatggaagga aagaacattt tcaaaaggaa attattttga aagtatgttt acaacaaact    360

gatactattg acagtttttt tttttaaata ataaaacact ttaagaagat tgtatttatg    420

gtaaaaggaa actggactaa caatgaggcc aaagactttt cctgccacga cttattctgg    480

aaatagccgg cagcgactgc aagagattcg tgaggggtta aaacagccat ccaagtcttc    540

ggttcagggg ctacccgcag gaccaaacag tgacacttcc ctggatgcca aagtcctggg    600

gagcaaagat gccaccaggc agcagcagca gatgagagcc accccaaagt tcggacctta    660

tcagaaagcc ttgagggaaa tcagatattc cttgttgcct tttgctaatg aatcgggcac    720

ctctgcagct gcagaagtga accggcaaat gctgcaggaa ctggtgaacg caggatgcga    780

ccaggagatg gctggccgag ctctcaagca gactggcagc aggagcatcg aggccgccct    840

ggagtacatc agcaagatgg gctacctgga cccgaggaat gagcagattg tgcgggtcat    900

taagcagacc tccccaggaa aggggctcat gccaacccca gtgacgcgga ggcccagctt    960

cgaaggaacc ggcgattcgt ttgcgtccta ccaccagctg agcggtaccc cctacgaggg   1020

cccaagcttc ggcgctgacg gccccacggc gctggaggag atgccgcggc cgtacgtgga   1080

ctaccttttc cccggagtcg gcccccacgg gcccggccac cagcaccagc acccacccaa   1140

gggctacggt gccagcgtag aggcagcagg ggcacacttc ccgctgcagg gcgcgcacta   1200

cgggcggccg cacctgctgg tgcctgggga acccctgggc tacggagtgc agcgcagccc   1260

ctccttccag agcaagacgc cgccggagac cgggggttac gccagcctgc ccacgaaggg   1320

ccagggagga ccgccaggcg ccggcctcgc tttcccaccc cctgccgccg ggctctacgt   1380

gccgcaccca caccacaagc aggccggtcc cgcggcccac cagctgcatg tgctgggctc   1440

ccgcagccag gtgttcgcca gcgacagccc cccgcagagc ctgctcactc cctcgcggaa   1500

cagcctcaac gtggacctgt atgaattggg cagcacctcc gtccagcagt ggccggctgc   1560

caccctggcc cgccgggact ccctgcagaa gccgggcctg gaggcgccgc cgcgcgcgca   1620

cgtggccttc cggcctgact gcccagtgcc cagcaggacc aactccttca acagccacca   1680

gccgcggccc ggtccgcctg gcaaggccga gccctccctg cccgccccca acaccgtgac   1740

ggctgtcacg gccgcgcaca tcttgcaccc ggtgaagagc gtgcgtgtgc tgaggccgga   1800
```

```
gccgcagacg gctgtggggc cctcgcaccc cgcctgggtg cccgcgcctg ccccggcccc   1860
cgcccccgcc cccgccccgg ctgcggaggg cttggacgcc aaggaggagc atgccctggc   1920
gctgggcggc gcaggcgcct tcccgctgga cgtggagtac ggaggcccag accggaggtg   1980
cccgcctccg ccctacccga agcacctgct gctgcgcagc aagtcggagc agtacgacct   2040
ggacagcctg tgcgcaggca tggagcagag cctccgtgcg ggccccaacg agcccgaggg   2100
cggcgacaag agccgcaaaa gcgccaaggg ggacaaaggc ggaaaggata aaaagcagat   2160
tcagacctct cccgttcccg tccgcaaaaa cagcagagac gaagagaaga gagagtcacg   2220
catcaagagc tactcgccat acgcctttaa gttcttcatg gagcagcacg tggagaatgt   2280
catcaaaacc taccagcaga aggttaaccg gaggctgcag ctggagcaag aaatggccaa   2340
agctggactc tgtgaagctg agcaggagca gatgcggaag atcctctacc agaaagagtc   2400
taattacaac aggttaaaga gggccaagat ggacaagtct atgtttgtca agatcaaaac   2460
cctggggatc ggtgcctttg gagaagtgtg ccttgcttgt aaggtggaca ctcacgccct   2520
gtacgccatg aagaccctaa ggaaaaagga tgtcctgaac cggaatcagg tggcccacgt   2580
caaggccgag agggacatcc tggccgaggc agacaatgag tgggtggtca aactctacta   2640
ctccttccaa gacaaagaca gcctgtactt tgtgatggac tacatccctg gtggggacat   2700
gatgagcctg ctgatccgga tggaggtctt ccctgagcac ctggcccggt tctacatcgc   2760
agagctgact ttggccattg agagtgtcca caagatgggc ttcatccacc gagacatcaa   2820
gcctgataac attttgatag atctggatgg tcacattaaa ctcacagatt tcggcctctg   2880
cactgggttc aggtggactc acaattccaa atattaccag aaagggagcc atgtcagaca   2940
ggacagcatg gagcccagcg acctctggga tgatgtgtct aactgtcggt gtggggacag   3000
gctgaagacc ctagagcaga gggcgcggaa gcagcaccag aggtgcctgg cacattcact   3060
ggtggggact ccaaactaca tcgcacccga ggtgctcctc cgcaaagggt acactcaact   3120
ctgtgactgg tggagtgttg gagtgattct cttcgagatg ctggtggggc agccgccctt   3180
tttggcacct actcccacag aaacccagct gaaggtgatc aactgggaga acacgctcca   3240
cattccagcc caggtgaagc tgagccctga ggccagggac ctcatcacca agctgtgctg   3300
ctccgcagac caccgcctgg ggcggaatgg ggccgatgac ctgaaggccc accccttctt   3360
cagcgccatt gacttctcca gtgacatccg gaagcagcca gcccccctacg ttcccaccat   3420
cagccacccc atggacacct cgaatttcga ccccgtagat gaagaaagcc cttggaacga   3480
tgccagcgaa ggtagcacca aggcctggga cacactcacc tcgcccaata acaagcatcc   3540
tgagcacgca ttttacgaat tcaccttccg aaggttcttt gatgacaatg gctacccctt   3600
tcgatgccca aagccttcag gagcagaagc ttcacaggct gagagctcag atttagaaag   3660
ctctgatctg gtggatcaga ctgaaggctg ccagcctgtg tacgtgtaga tgggggccag   3720
gcacccccac cactcgctgc ctcccaggtc agggtcccgg agccggtgcc ctcacaggcc   3780
aatagggaag ccgagggctg ttttgtttta aattagtccg tcgattactt cacttgaaat   3840
tctgctcttc accaagaaaa cccaaacagg acacttttga aaacaggact cagcatcgct   3900
ttcaataggc ttttcaggac cttcactgca ttaaaacaat atttttgaaa atttagtaca   3960
gtttagaaag agcacttatt ttgtttatat ccatttttttc ttactaaatt atagggatta   4020
actttgacaa atcatgctgc tgttattttc tacatttgta ttttatccat agcacttatt   4080
cacatttagg aaaagacata aaaactgaag aacattgatg agaaatctct gtgcaataat   4140
```

```
gtaaaaaaaa aaaaagataa cactctgctc aatgtcacgg agaccatttt atccacacaa   4200

tggtttttgt tttttatttt ttcccatgtt tcaaaattgt gatataatga tataatgtta   4260

aaagctgctt tttttggctt tttgcatatc tagtataata ggaagtgtga gcaaggtgat   4320

gatgtggctg tgatttccga cgtctggtgt gtggagagta ctgcatgagc agagttcttc   4380

tattataaaa ttaccatatc ttgccattca cagcaggtcc tgtgaatacg tttttactga   4440

gtgtctttaa atgaggtgtt ctagacagtg tgctgataat gtattgtgcg ggtgacctct   4500

tcgctatgat tgtatctctt actgttttgt taaagaaatg cagatgtgta actgagaagt   4560

gatttgtgtg tgtgtcttgg ttgtgattgg attctttggg gggggggaac tgaaacattt   4620

gtcatatact gaacttatat acatcaaaag ggattaatac agcgatgcca aaaagtttaa   4680

tcacggacac atgtccgttt ctgtagtccg tatgctcttt cattcttggt agagctggta   4740

tgtggaatgc catacctctg accctactac ttaccttttt actgacagac tgcccacact   4800

gaaagcttca gtgaatgttc ttagtcctgt tttcttctgt tactgtcagg aaactgagtg   4860

atctaatggt tctctcactt ttttttgtt ctttagtgt actttgaagt atcaaatctt   4920

aacttggttt aaacaataca tattcctaac ctttgtaaaa aagcaaagat tcttcaaaat   4980

gacattgaaa taaaaagtaa gccatacgta ttttcttaga agtatagatg tatgtgcgtg   5040

tatacacaca cacacacaca cacagagata aacacaatat tccttatttc aaattagtat   5100

gattcctatt taaagtgatt tatatttgag taaaaagttc aattcttttt tgctttttaa   5160

aaaatctgat gcttcataat tttcattata ttattccaca tatttttcct tgaagttctt   5220

agcataatgt atccattact tagtatatat ctaggcaaca acacttagaa gtttatcagt   5280

gtttaaacta aaaaaataaa gattcctgtg tactggttta catttgtgtg agtggcatac   5340

tcaagtctgc tgtgcctgtc gtcgtgactg tcagtattct cgctatttta tagtcgtgcc   5400

atgttgttac tcacagcgct ctgacatact ttcatgtggt aggttctttc tcaggaactc   5460

agtttaacta ttatttattg atatatcatt acctttgaaa agcttctact ggcacaattt   5520

attattaaaa ttttgaatcc aaaaaaaaaa aaaaaaaa                           5558
```

```
<210> SEQ ID NO 4
<211> LENGTH: 1088
<212> TYPE: PRT
<213> ORGANISM: Homo sapiens

<400> SEQUENCE: 4

Met Arg Pro Lys Thr Phe Pro Ala Thr Thr Tyr Ser Gly Asn Ser Arg
1               5                   10                  15

Gln Arg Leu Gln Glu Ile Arg Glu Gly Leu Lys Gln Pro Ser Lys Ser
            20                  25                  30

Ser Val Gln Gly Leu Pro Ala Gly Pro Asn Ser Asp Thr Ser Leu Asp
        35                  40                  45

Ala Lys Val Leu Gly Ser Lys Asp Ala Thr Arg Gln Gln Gln Gln Met
    50                  55                  60

Arg Ala Thr Pro Lys Phe Gly Pro Tyr Gln Lys Ala Leu Arg Glu Ile
65                  70                  75                  80

Arg Tyr Ser Leu Leu Pro Phe Ala Asn Glu Ser Gly Thr Ser Ala Ala
                85                  90                  95

Ala Glu Val Asn Arg Gln Met Leu Gln Glu Leu Val Asn Ala Gly Cys
            100                 105                 110

Asp Gln Glu Met Ala Gly Arg Ala Leu Lys Gln Thr Gly Ser Arg Ser
        115                 120                 125
```

```
Ile Glu Ala Ala Leu Glu Tyr Ile Ser Lys Met Gly Tyr Leu Asp Pro
    130                 135                 140

Arg Asn Glu Gln Ile Val Arg Val Ile Lys Gln Thr Ser Pro Gly Lys
145                 150                 155                 160

Gly Leu Met Pro Thr Pro Val Thr Arg Arg Pro Ser Phe Glu Gly Thr
                165                 170                 175

Gly Asp Ser Phe Ala Ser Tyr His Gln Leu Ser Gly Thr Pro Tyr Glu
            180                 185                 190

Gly Pro Ser Phe Gly Ala Asp Gly Pro Thr Ala Leu Glu Glu Met Pro
        195                 200                 205

Arg Pro Tyr Val Asp Tyr Leu Phe Pro Gly Val Gly Pro His Gly Pro
    210                 215                 220

Gly His Gln His Gln His Pro Pro Lys Gly Tyr Gly Ala Ser Val Glu
225                 230                 235                 240

Ala Ala Gly Ala His Phe Pro Leu Gln Gly Ala His Tyr Gly Arg Pro
                245                 250                 255

His Leu Leu Val Pro Gly Glu Pro Leu Gly Tyr Gly Val Gln Arg Ser
            260                 265                 270

Pro Ser Phe Gln Ser Lys Thr Pro Pro Glu Thr Gly Gly Tyr Ala Ser
        275                 280                 285

Leu Pro Thr Lys Gly Gln Gly Gly Pro Pro Gly Ala Gly Leu Ala Phe
    290                 295                 300

Pro Pro Pro Ala Ala Gly Leu Tyr Val Pro His Pro His His Lys Gln
305                 310                 315                 320

Ala Gly Pro Ala Ala His Gln Leu His Val Leu Gly Ser Arg Ser Gln
                325                 330                 335

Val Phe Ala Ser Asp Ser Pro Pro Gln Ser Leu Leu Thr Pro Ser Arg
            340                 345                 350

Asn Ser Leu Asn Val Asp Leu Tyr Glu Leu Gly Ser Thr Ser Val Gln
        355                 360                 365

Gln Trp Pro Ala Ala Thr Leu Ala Arg Arg Asp Ser Leu Gln Lys Pro
    370                 375                 380

Gly Leu Glu Ala Pro Pro Arg Ala His Val Ala Phe Arg Pro Asp Cys
385                 390                 395                 400

Pro Val Pro Ser Arg Thr Asn Ser Phe Asn Ser His Gln Pro Arg Pro
                405                 410                 415

Gly Pro Pro Gly Lys Ala Glu Pro Ser Leu Pro Ala Pro Asn Thr Val
            420                 425                 430

Thr Ala Val Thr Ala Ala His Ile Leu His Pro Val Lys Ser Val Arg
        435                 440                 445

Val Leu Arg Pro Glu Pro Gln Thr Ala Val Gly Pro Ser His Pro Ala
    450                 455                 460

Trp Val Pro Ala Pro Ala Pro Ala Pro Ala Pro Ala Pro Ala Pro Ala
465                 470                 475                 480

Ala Glu Gly Leu Asp Ala Lys Glu Glu His Ala Leu Ala Leu Gly Gly
                485                 490                 495

Ala Gly Ala Phe Pro Leu Asp Val Glu Tyr Gly Gly Pro Asp Arg Arg
            500                 505                 510

Cys Pro Pro Pro Pro Tyr Pro Lys His Leu Leu Leu Arg Ser Lys Ser
        515                 520                 525

Glu Gln Tyr Asp Leu Asp Ser Leu Cys Ala Gly Met Glu Gln Ser Leu
    530                 535                 540
```

```
Arg Ala Gly Pro Asn Glu Pro Glu Gly Gly Asp Lys Ser Arg Lys Ser
545                 550                 555                 560

Ala Lys Gly Asp Lys Gly Gly Lys Asp Lys Lys Gln Ile Gln Thr Ser
                565                 570                 575

Pro Val Pro Val Arg Lys Asn Ser Arg Asp Glu Glu Lys Arg Glu Ser
            580                 585                 590

Arg Ile Lys Ser Tyr Ser Pro Tyr Ala Phe Lys Phe Phe Met Glu Gln
        595                 600                 605

His Val Glu Asn Val Ile Lys Thr Tyr Gln Gln Lys Val Asn Arg Arg
    610                 615                 620

Leu Gln Leu Glu Gln Glu Met Ala Lys Ala Gly Leu Cys Glu Ala Glu
625                 630                 635                 640

Gln Glu Gln Met Arg Lys Ile Leu Tyr Gln Lys Glu Ser Asn Tyr Asn
                645                 650                 655

Arg Leu Lys Arg Ala Lys Met Asp Lys Ser Met Phe Val Lys Ile Lys
            660                 665                 670

Thr Leu Gly Ile Gly Ala Phe Gly Glu Val Cys Leu Ala Cys Lys Val
        675                 680                 685

Asp Thr His Ala Leu Tyr Ala Met Lys Thr Leu Arg Lys Lys Asp Val
    690                 695                 700

Leu Asn Arg Asn Gln Val Ala His Val Lys Ala Glu Arg Asp Ile Leu
705                 710                 715                 720

Ala Glu Ala Asp Asn Glu Trp Val Val Lys Leu Tyr Tyr Ser Phe Gln
                725                 730                 735

Asp Lys Asp Ser Leu Tyr Phe Val Met Asp Tyr Ile Pro Gly Gly Asp
            740                 745                 750

Met Met Ser Leu Leu Ile Arg Met Glu Val Phe Pro Glu His Leu Ala
        755                 760                 765

Arg Phe Tyr Ile Ala Glu Leu Thr Leu Ala Ile Glu Ser Val His Lys
    770                 775                 780

Met Gly Phe Ile His Arg Asp Ile Lys Pro Asp Asn Ile Leu Ile Asp
785                 790                 795                 800

Leu Asp Gly His Ile Lys Leu Thr Asp Phe Gly Leu Cys Thr Gly Phe
                805                 810                 815

Arg Trp Thr His Asn Ser Lys Tyr Tyr Gln Lys Gly Ser His Val Arg
            820                 825                 830

Gln Asp Ser Met Glu Pro Ser Asp Leu Trp Asp Asp Val Ser Asn Cys
        835                 840                 845

Arg Cys Gly Asp Arg Leu Lys Thr Leu Glu Gln Arg Ala Arg Lys Gln
    850                 855                 860

His Gln Arg Cys Leu Ala His Ser Leu Val Gly Thr Pro Asn Tyr Ile
865                 870                 875                 880

Ala Pro Glu Val Leu Leu Arg Lys Gly Tyr Thr Gln Leu Cys Asp Trp
                885                 890                 895

Trp Ser Val Gly Val Ile Leu Phe Glu Met Leu Val Gly Gln Pro Pro
            900                 905                 910

Phe Leu Ala Pro Thr Pro Thr Glu Thr Gln Leu Lys Val Ile Asn Trp
        915                 920                 925

Glu Asn Thr Leu His Ile Pro Ala Gln Val Lys Leu Ser Pro Glu Ala
    930                 935                 940

Arg Asp Leu Ile Thr Lys Leu Cys Cys Ser Ala Asp His Arg Leu Gly
945                 950                 955                 960

Arg Asn Gly Ala Asp Asp Leu Lys Ala His Pro Phe Phe Ser Ala Ile
```

```
                965                 970                 975

Asp Phe Ser Ser Asp Ile Arg Lys Gln Pro Ala Pro Tyr Val Pro Thr
            980                 985                 990

Ile Ser His Pro Met Asp Thr Ser  Asn Phe Asp Pro Val  Asp Glu Glu
        995                 1000                1005

Ser Pro  Trp Asn Asp Ala Ser  Glu Gly Ser Thr Lys  Ala Trp Asp
    1010                 1015                1020

Thr Leu  Thr Ser Pro Asn Asn  Lys His Pro Glu His  Ala Phe Tyr
    1025                 1030                1035

Glu Phe  Thr Phe Arg Arg Phe  Phe Asp Asp Asn Gly  Tyr Pro Phe
    1040                 1045                1050

Arg Cys  Pro Lys Pro Ser Gly  Ala Glu Ala Ser Gln  Ala Glu Ser
    1055                 1060                1065

Ser Asp  Leu Glu Ser Ser Asp  Leu Val Asp Gln Thr  Glu Gly Cys
    1070                 1075                1080

Gln Pro  Val Tyr Val
    1085


<210> SEQ ID NO 5
<211> LENGTH: 1893
<212> TYPE: DNA
<213> ORGANISM: Homo sapiens

<400> SEQUENCE: 5

gggctaaagg gctcagagtg caggccgtgg ggcgcgaggg tcccgggcct gagccccgcg     60

ccatggccgg ggccatcgct tcccgcatga gcttcagctc tctcaagagg aagcaaccca    120

agacgttcac cgtgaggatc gtcaccatgg acgccgagat ggagttcaat tgcgagatga    180

agtggaaagg gaaggacctc tttgatttgg tgtgccggac tctggggctc cgagaaacct    240

ggttctttgg actgcagtac acaatcaagg acacagtggc ctggctcaaa atggacaaga    300

aggtactgga tcatgatgtt tcaaaggaag aaccagtcac ctttcacttc ttggccaaat    360

tttatcctga gaatgctgaa gaggagctgg ttcaggagat cacacaacat ttattcttct    420

tacaggtaaa gaagcagatt ttagatgaaa agatctactg ccctcctgag gcttctgtgc    480

tcctggcttc ttacgccgtc caggccaagt atggtgacta cgaccccagt gttcacaagc    540

ggggattttt ggcccaagag gaattgcttc caaaaagggt aataaatctg tatcagatga    600

ctccggaaat gtgggaggag agaattactg cttggtacgc agagcaccga ggccgagcca    660

gggatgaagc tgaaatggaa tatctgaaga tagctcagga cctggagatg tacggtgtga    720

actactttgc aatccggaat aaaaagggca cagagctgct gcttggagtg gatgccctgg    780

ggcttcacat ttatgaccct gagaacagac tgacccccaa gatctccttc ccgtggaatg    840

aaatccgaaa catctcgtac agtgacaagg agtttactat taaaccactg gataagaaaa    900

ttgatgtctt caagtttaac tcctcaaagc ttcgtgttaa taagctgatt ctccagctat    960

gtatcgggaa ccatgatcta tttatgagga gaaggaaagc cgattctttg gaagttcagc   1020

agatgaaagc ccaggccagg gaggagaagg ctagaaagca gatggagcgg cagcgcctcg   1080

ctcgagagaa gcagatgagg gaggaggctg aacgcacgag ggatgagttg gagaggaggc   1140

tgctgcagat gaaagaagaa gcaacaatgg ccaacgaagc actgatgcgg tctgaggaga   1200

cagctgacct gttggctgaa aaggcccaga tcaccgagga ggaggcaaaa cttctggccc   1260

agaaggccgc agaggctgag caggaaatgc agcgcatcaa ggccacagcg attcgcacgg   1320

aggaggagaa gcgcctgatg gagcagaagg tgctggaagc cgaggtgctg gcactgaaga   1380
```

```
tggctgagga gtcagagagg agggccaaag aggcagatca gctgaagcag gacctgcagg   1440

aagcacgcga ggcggagcga agagccaagc agaagctcct ggagattgcc accaagccca   1500

cgtacccgcc catgaaccca attccagcac cgttgcctcc tgacatacca agcttcaacc   1560

tcattggtga cagcctgtct ttcgacttca aagatactga catgaagcgg ctttccatgg   1620

agatagagaa agaaaaagtg gaatacatgg aaaagagcaa gcatctgcag gagcagctca   1680

atgaactcaa gacagaaatc gaggccttga aactgaaaga gagggagaca gctctggata   1740

ttctgcacaa tgagaactcc gacaggggtg gcagcagcaa gcacaatacc attaaaaagc   1800

tcaccttgca gagcgccaag tcccgagtgg ccttctttga agagctctag caggtgaccc   1860

agccacccca ggacctgcca cttctcctgc tac                                1893
```

```
<210> SEQ ID NO 6
<211> LENGTH: 595
<212> TYPE: PRT
<213> ORGANISM: Homo sapiens

<400> SEQUENCE: 6

Met Ala Gly Ala Ile Ala Ser Arg Met Ser Phe Ser Ser Leu Lys Arg
1               5                   10                  15

Lys Gln Pro Lys Thr Phe Thr Val Arg Ile Val Thr Met Asp Ala Glu
            20                  25                  30

Met Glu Phe Asn Cys Glu Met Lys Trp Lys Gly Lys Asp Leu Phe Asp
        35                  40                  45

Leu Val Cys Arg Thr Leu Gly Leu Arg Glu Thr Trp Phe Phe Gly Leu
    50                  55                  60

Gln Tyr Thr Ile Lys Asp Thr Val Ala Trp Leu Lys Met Asp Lys Lys
65                  70                  75                  80

Val Leu Asp His Asp Val Ser Lys Glu Glu Pro Val Thr Phe His Phe
                85                  90                  95

Leu Ala Lys Phe Tyr Pro Glu Asn Ala Glu Glu Glu Leu Val Gln Glu
            100                 105                 110

Ile Thr Gln His Leu Phe Phe Leu Gln Val Lys Lys Gln Ile Leu Asp
        115                 120                 125

Glu Lys Ile Tyr Cys Pro Pro Glu Ala Ser Val Leu Leu Ala Ser Tyr
    130                 135                 140

Ala Val Gln Ala Lys Tyr Gly Asp Tyr Asp Pro Ser Val His Lys Arg
145                 150                 155                 160

Gly Phe Leu Ala Gln Glu Glu Leu Leu Pro Lys Arg Val Ile Asn Leu
                165                 170                 175

Tyr Gln Met Thr Pro Glu Met Trp Glu Glu Arg Ile Thr Ala Trp Tyr
            180                 185                 190

Ala Glu His Arg Gly Arg Ala Arg Asp Glu Ala Glu Met Glu Tyr Leu
        195                 200                 205

Lys Ile Ala Gln Asp Leu Glu Met Tyr Gly Val Asn Tyr Phe Ala Ile
    210                 215                 220

Arg Asn Lys Lys Gly Thr Glu Leu Leu Leu Gly Val Asp Ala Leu Gly
225                 230                 235                 240

Leu His Ile Tyr Asp Pro Glu Asn Arg Leu Thr Pro Lys Ile Ser Phe
                245                 250                 255

Pro Trp Asn Glu Ile Arg Asn Ile Ser Tyr Ser Asp Lys Glu Phe Thr
            260                 265                 270

Ile Lys Pro Leu Asp Lys Lys Ile Asp Val Phe Lys Phe Asn Ser Ser
```

```
        275                 280                 285

Lys Leu Arg Val Asn Lys Leu Ile Leu Gln Leu Cys Ile Gly Asn His
    290                 295                 300

Asp Leu Phe Met Arg Arg Arg Lys Ala Asp Ser Leu Glu Val Gln Gln
305                 310                 315                 320

Met Lys Ala Gln Ala Arg Glu Glu Lys Ala Arg Lys Gln Met Glu Arg
                325                 330                 335

Gln Arg Leu Ala Arg Glu Lys Gln Met Arg Glu Glu Ala Glu Arg Thr
            340                 345                 350

Arg Asp Glu Leu Glu Arg Arg Leu Leu Gln Met Lys Glu Glu Ala Thr
        355                 360                 365

Met Ala Asn Glu Ala Leu Met Arg Ser Glu Glu Thr Ala Asp Leu Leu
    370                 375                 380

Ala Glu Lys Ala Gln Ile Thr Glu Glu Glu Ala Lys Leu Leu Ala Gln
385                 390                 395                 400

Lys Ala Ala Glu Ala Glu Gln Glu Met Gln Arg Ile Lys Ala Thr Ala
                405                 410                 415

Ile Arg Thr Glu Glu Glu Lys Arg Leu Met Glu Gln Lys Val Leu Glu
            420                 425                 430

Ala Glu Val Leu Ala Leu Lys Met Ala Glu Glu Ser Glu Arg Arg Ala
        435                 440                 445

Lys Glu Ala Asp Gln Leu Lys Gln Asp Leu Gln Glu Ala Arg Glu Ala
    450                 455                 460

Glu Arg Arg Ala Lys Gln Lys Leu Leu Glu Ile Ala Thr Lys Pro Thr
465                 470                 475                 480

Tyr Pro Pro Met Asn Pro Ile Pro Ala Pro Leu Pro Pro Asp Ile Pro
                485                 490                 495

Ser Phe Asn Leu Ile Gly Asp Ser Leu Ser Phe Asp Phe Lys Asp Thr
            500                 505                 510

Asp Met Lys Arg Leu Ser Met Glu Ile Glu Lys Glu Lys Val Glu Tyr
        515                 520                 525

Met Glu Lys Ser Lys His Leu Gln Glu Gln Leu Asn Glu Leu Lys Thr
    530                 535                 540

Glu Ile Glu Ala Leu Lys Leu Lys Glu Arg Glu Thr Ala Leu Asp Ile
545                 550                 555                 560

Leu His Asn Glu Asn Ser Asp Arg Gly Gly Ser Ser Lys His Asn Thr
                565                 570                 575

Ile Lys Lys Leu Thr Leu Gln Ser Ala Lys Ser Arg Val Ala Phe Phe
            580                 585                 590

Glu Glu Leu
        595


<210> SEQ ID NO 7
<211> LENGTH: 5396
<212> TYPE: DNA
<213> ORGANISM: Homo sapiens

<400> SEQUENCE: 7

gccgccgcca gggaaaagaa agggaggaag gaaggaacaa gaaaaggaaa taaagagaaa      60

ggggaggcgg ggaaaggcaa cgagctgtcc ggcctccgtc aagggagttg gagggaaaaa     120

gttctcaggc gccgcaggtc cgagtgcctc gcagcccctc ccgaggcgca gccgccagac     180

cagtggagcc ggggcgcagg gcgggggcgg aggcgccggg gcgggggatg cggggccgcg     240

gcgcagcccc ccggccctga gagcgaggac agcgccgccc ggcccgcagc cgtcgccgct     300
```

```
tctccacctc ggcccgtgga gccggggcgt ccgggcgtag ccctcgctcg cctgggtcag    360
ggggtgcgcg tcgggggagg cagaagccat ggatcccggg cagcagccgc cgcctcaacc    420
ggccccccag ggccaagggc agccgccttc gcagccccg caggggcagg gcccgccgtc    480
cggacccggg caaccggcac ccgcggcgac ccaggcggcg ccgcaggcac cccccgccgg    540
gcatcagatc gtgcacgtcc gcggggactc ggagaccgac ctggaggcgc tcttcaacgc    600
cgtcatgaac cccaagacgg ccaacgtgcc ccagaccgtg cccatgaggc tccggaagct    660
gcccgactcc ttcttcaagc cgccggagcc caaatcccac tcccgacagg ccagtactga    720
tgcaggcact gcaggagccc tgactccaca gcatgttcga gctcattcct ctccagcttc    780
tctgcagttg ggagctgttt ctcctgggac actgaccccc actggagtag tctctggccc    840
agcagctaca cccacagctc agcatcttcg acagtcttct tttgagatac ctgatgatgt    900
acctctgcca gcaggttggg agatggcaaa gacatcttct ggtcagagat acttcttaaa    960
tcacatcgat cagacaacaa catggcagga ccccaggaag gccatgctgt cccagatgaa   1020
cgtcacagcc cccaccagtc caccagtgca gcagaatatg atgaactcgg cttcaggtcc   1080
tcttcctgat ggatgggaac aagccatgac tcaggatgga gaaatttact atataaacca   1140
taagaacaag accacctctt ggctagaccc aaggcttgac cctcgttttg ccatgaacca   1200
gagaatcagt cagagtgctc cagtgaaaca gccaccaccc ctggctcccc agagcccaca   1260
gggaggcgtc atgggtggca gcaactccaa ccagcagcaa cagatgcgac tgcagcaact   1320
gcagatggag aaggagaggc tgcggctgaa acagcaagaa ctgcttcggc aggcaatgcg   1380
gaatatcaat cccagcacag caaattctcc aaaatgtcag gagttagccc tgcgtagcca   1440
gttaccaaca ctggagcagg atggtgggac tcaaaatcca gtgtcttctc ccgggatgtc   1500
tcaggaattg agaacaatga cgaccaatag ctcagatcct ttccttaaca gtggcaccta   1560
tcactctcga gatgagagta cagacagtgg actaagcatg agcagctaca gtgtccctcg   1620
aaccccagat gacttcctga acagtgtgga tgagatggat acaggtgata ctatcaacca   1680
aagcaccctg ccctcacagc agaaccgttt cccagactac cttgaagcca ttcctgggac   1740
aaatgtggac cttggaacac tggaaggaga tggaatgaac atagaaggag aggagctgat   1800
gccaagtctg caggaagctt tgagttctga catccttaat gacatggagt ctgttttggc   1860
tgccaccaag ctagataaag aaagctttct tacatggtta tagagccctc aggcagactg   1920
aattctaaat ctgtgaagga tctaaggaga cacatgcacc ggaaatttcc ataagccagt   1980
tgcagttttc aggctaatac agaaaaagat gaacaaacgt ccagcaagat actttaatcc   2040
tctattttgc tcttccttgt ccattgctgc tgttaatgta ttgctgacct ctttcacagt   2100
tggctctaaa gaatcaaaag aaaaaaactt tttatttctt ttgctattaa aactactgtt   2160
cattttgggg gctgggggaa gtgagcctgt ttggatgatg gatgccattc cttttgccca   2220
gttaaatgtt caccaatcat tttaactaaa tactcagact tagaagtcag atgcttcatg   2280
tcacagcatt tagtttgttc aacagttgtt tcttcagctt cctttgtcca gtggaaaaac   2340
atgatttact ggtctgacaa gccaaaaatg ttatatctga tattaaatac ttaatgctga   2400
tttgaagaga tagctgaaac caaggctgaa gactgtttta ctttcagtat tttcttttcc   2460
tcctagtgct atcattagtc acataatgac cttgatttta ttttaggagc ttataaggca   2520
tgagacaatt tccatataaa tatattaatt attgccacat actctaatat agattttggt   2580
ggataatttt gtgggtgtgc attttgttct gttttgttgg gtttttttgtt tttttgttt   2640
```

```
ttggcagggt cggtgggggg gttggttggt tggttggttt tgtcggaacc taggcaaatg   2700
accatattag tgaatctgtt aatagttgta gcttgggatg gttattgtag ttgttttggt   2760
aaaatcttca tttcctggtt ttttttacca ccttatttaa atctcgatta tctgctctct   2820
cttttatata catacacaca cccaaacata acatttataa tagtgtggta gtggaatgta   2880
tccttttttta ggtttccctg ctttccagtt aatttttaaa atggtagcgc tttgtatgca   2940
tttagaatac atgactagta gtttatattt cactggtagt ttaaatctgg ttggggcagt   3000
ctgcagatgt ttgaagtagt ttagtgttct agaaagagct attactgtgg atagtgccta   3060
ggggagtgct ccacgccctc tgggcatacg gtagatatta tctgatgaat tggaaaggag   3120
caaaccagaa atggctttat tttctccctt ggactaattt ttaagtctcg attggaattc   3180
agtgagtagg ttcataatgt gcatgacaga aataagcttt atagtggttt accttcattt   3240
agctttggaa gttttctttg ccttagtttt ggaagtaaat tctagtttgt agttctcatt   3300
tgtaatgaac acattaacga ctagattaaa atattgcctt caagattgtt cttacttaca   3360
agacttgctc ctacttctat gctgaaaatt gaccctggat agaatactat aaggttttga   3420
gttagctgga aaagtgatca gattaataaa tgtatattgg tagttgaatt tagcaaagaa   3480
atagagataa tcatgattat acctttattt ttacaggaag agatgatgta actagagtat   3540
gtgtctacag gagtaataat ggtttccaaa gagtattttt taaaggaaca aaacgagcat   3600
gaattaactc ttcaatataa gctatgaagt aatagttggt tgtgaattaa agtggcacca   3660
gctagcacct ctgtgtttta agggtctttc aatgtttcta gaataagccc ttattttcaa   3720
gggttcataa caggcataaa atctcttctc ctggcaaaag ctgctatgaa aagcctcagc   3780
ttgggaagat agattttttt ccccccaatt acaaaatcta agtattttgg cccttcaatt   3840
tggaggaggg caaaagttgg aagtaagaag ttttatttta agtactttca gtgctcaaaa   3900
aaatgcaatc actgtgttgt atataatagt tcataggttg atcactcata ataattgact   3960
ctaaggcttt tattaagaaa acagcagaaa gattaaatct tgaattaagt ctgggggaa    4020
atggccactg cagatggagt tttagagtag taatgaaatt ctacctagaa tgcaaaattg   4080
ggtatatgaa ttacatagca tgttgttggg atttttttta atgtgcagaa gatcaaagct   4140
acttggaagg agtgcctata atttgccagt agccacagat taagattata tcttatatat   4200
cagcagatta gctttagctt agggggaggg tgggaaagtt tgggggggg gttgtgaaga   4260
tttaggggga ccttgataga gaactttata aacttctttc tctttaataa agacttgtct   4320
tacaccgtgc tgccattaaa ggcagctgtt ctagagtttc agtcacctaa gtacacccac   4380
aaaacaatat gaatatggag atcttccttt acccctcaac tttaatttgc ccagttatac   4440
ctcagtgttg tagcagtact gtgatacctg gcacagtgct ttgatcttac gatgccctct   4500
gtactgacct gaaggagacc taagagtcct ttcccttttt gagtttgaat catagccttg   4560
atgtggtctc ttgttttatg tccttgttcc taatgtaaaa gtgcttaact gcttcttggt   4620
tgtattgggt agcattggga taagatttta actgggtatt cttgaattgc ttttacaata   4680
aaccaatttt ataatcttta aatttatcaa ctttttacat ttgtgttatt ttcagtcagg   4740
gcttcttaga tctacttatg gttgatggag cacattgatt tggagtttca gatcttccaa   4800
agcactattt gttgtaataa cttttctaaa tgtagtgcct ttaaaggaaa aatgaacaca   4860
gggaagtgac tttgctacaa ataatgttgc tgtgttaagt attcatatta aatacatgcc   4920
ttctatatgg aacatggcag aaagactgaa aaataacagt aattaattgt gtaattcaga   4980
attcatacca atcagtgttg aaactcaaac attgcaaaag tgggtggcaa tattcagtgc   5040
```

```
ttaacacttt tctagcgttg gtacatctga gaaatgagtg ctcaggtgga ttttatcctc   5100

gcaagcatgt tgttataaga attgtgggtg tgcctatcat aacaattgtt ttctgtatct   5160

tgaaaaagta ttctccacat tttaaatgtt ttatattaga gaattcttta atgcacactt   5220

gtcaaatata tatatatagt accaatgtta cctttttatt ttttgtttta gatgtaagag   5280

catgctcata tgttaggtac ttacataaat tgttacatta ttttttctta tgtaatacct   5340

ttttgtttgt ttatgtggtt caaatatatt ctttccttaa actcttaaaa aaaaaa       5396
```

```
<210> SEQ ID NO 8
<211> LENGTH: 504
<212> TYPE: PRT
<213> ORGANISM: Homo sapiens

<400> SEQUENCE: 8

Met Asp Pro Gly Gln Gln Pro Pro Pro Gln Pro Ala Pro Gln Gly Gln
1               5                   10                  15

Gly Gln Pro Pro Ser Gln Pro Pro Gln Gly Gln Gly Pro Pro Ser Gly
            20                  25                  30

Pro Gly Gln Pro Ala Pro Ala Ala Thr Gln Ala Ala Pro Gln Ala Pro
        35                  40                  45

Pro Ala Gly His Gln Ile Val His Val Arg Gly Asp Ser Glu Thr Asp
    50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
    210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
            260                 265                 270

Ile Ser Gln Ser Ala Pro Val Lys Gln Pro Pro Pro Leu Ala Pro Gln
        275                 280                 285

Ser Pro Gln Gly Gly Val Met Gly Gly Ser Asn Ser Asn Gln Gln Gln
    290                 295                 300

Gln Met Arg Leu Gln Gln Leu Gln Met Glu Lys Glu Arg Leu Arg Leu
```

```
305                 310                 315                 320

Lys Gln Gln Glu Leu Leu Arg Gln Ala Met Arg Asn Ile Asn Pro Ser
                325                 330                 335

Thr Ala Asn Ser Pro Lys Cys Gln Glu Leu Ala Leu Arg Ser Gln Leu
            340                 345                 350

Pro Thr Leu Glu Gln Asp Gly Gly Thr Gln Asn Pro Val Ser Ser Pro
        355                 360                 365

Gly Met Ser Gln Glu Leu Arg Thr Met Thr Thr Asn Ser Ser Asp Pro
    370                 375                 380

Phe Leu Asn Ser Gly Thr Tyr His Ser Arg Asp Glu Ser Thr Asp Ser
385                 390                 395                 400

Gly Leu Ser Met Ser Ser Tyr Ser Val Pro Arg Thr Pro Asp Asp Phe
                405                 410                 415

Leu Asn Ser Val Asp Glu Met Asp Thr Gly Asp Thr Ile Asn Gln Ser
            420                 425                 430

Thr Leu Pro Ser Gln Gln Asn Arg Phe Pro Asp Tyr Leu Glu Ala Ile
        435                 440                 445

Pro Gly Thr Asn Val Asp Leu Gly Thr Leu Glu Gly Asp Gly Met Asn
    450                 455                 460

Ile Glu Gly Glu Glu Leu Met Pro Ser Leu Gln Glu Ala Leu Ser Ser
465                 470                 475                 480

Asp Ile Leu Asn Asp Met Glu Ser Val Leu Ala Ala Thr Lys Leu Asp
                485                 490                 495

Lys Glu Ser Phe Leu Thr Trp Leu
            500
```

<210> SEQ ID NO 9
<211> LENGTH: 9599
<212> TYPE: DNA
<213> ORGANISM: Homo sapiens

<400> SEQUENCE: 9

```
cgaagatggc ggcgtcgcgt cgctctcagc atcatcacca ccatcatcaa caacagctcc     60

agcccgcccc aggggcttca gcgccgccgc cgccacctcc tcccccactc agccctggcc    120

tggccccggg gaccacccca gcctctccca cggccagcgg cctggccccc ttcgcctccc    180

cgcggcacgg cctagcgctg ccggaggggg atggcagtcg ggatccgccc gacaggcccc    240

gatccccgga cccggttgac ggtaccagct gttgcagtac caccagcaca atctgtaccg    300

tcgccgccgc tcccgtggtc ccagcggttt ctacttcatc tgccgctggg gtcgctccca    360

acccagccgg cagtggcagt aacaattcac cgtcgtcctc ttcttccccg acttcttcct    420

catcttcctc tccatcctcc cctggatcga gcttggcgga gagccccgag gcggccggag    480

ttagcagcac agcaccactg gggcctgggg cagcaggacc tgggacaggg gtcccagcag    540

tgagcggggc cctacgggaa ctgctggagg cctgtcgcaa tggggacgtg tcccgggtaa    600

agaggctggt ggacgcggca aacgtaaatg caaaggacat ggccggccgg aagtcttctc    660

ccctgcactt cgctgcaggt tttggaagga aggatgttgt agaacactta ctacagatgg    720

gtgctaatgt ccacgctcgt gatgatggag gtctcatccc gcttcataat gcctgttctt    780

ttggccatgc tgaggttgtg agtctgttat tgtgccaagg agctgatcca aatgccaggg    840

ataactggaa ctatacacct ctgcatgaag ctgctattaa agggaagatc gatgtgtgca    900

ttgtgctgct gcagcacgga gctgacccaa acattcggaa cactgatggg aaatcagccc    960

tggacctggc agatccttca gcaaaagctg tccttacagg tgaatacaag aaagacgaac   1020
```

```
tcctagaagc tgctaggagt ggtaatgaag aaaaactaat ggctttactg actcctctaa   1080
atgtgaattg ccatgcaagt gatgggcgaa agtcgactcc tttacatcta gcagcgggct   1140
acaacagagt tcgaatagtt cagcttcttc ttcagcatgg tgctgatgtt catgcaaaag   1200
acaaaggtgg acttgtgcct cttcataatg catgttcata tggacattat gaagtcacag   1260
aactgctact aaagcatgga gcttgtgtta atgccatgga tctctggcag tttactccac   1320
tgcacgaggc tgcttccaag aaccgtgtag aagtctgctc tttgttactt agccatggcg   1380
ctgatcctac attagtcaac tgccatggca aaagtgctgt ggatatggct ccaactccgg   1440
agcttaggga gagattgact tatgaattta aaggtcattc tttactacaa gcagccagag   1500
aagcagactt agctaaagtt aaaaaaacac tcgctctgga aatcattaat ttcaaacaac   1560
cgcagtctca tgaaacagca ctgcactgtg ctgtggcctc tctgcatccc aaacgtaaac   1620
aagtgacaga attgttactt agaaaaggag caaatgttaa tgaaaaaaat aaagatttca   1680
tgactcccct gcatgttgca gccgaaagag cccataatga tgtcatggaa gttctgcata   1740
agcatggcgc caagatgaat gcactggaca cccttggtca gactgctttg catagagccg   1800
ccctagcagg ccacctgcag acctgccgcc tcctgctgag ttacggctct gacccctcca   1860
tcatctcctt acaaggcttc acagcagcac agatgggcaa tgaagcagtg cagcagattc   1920
tgagtgagag tacacctata cgtacttctg atgttgatta tcgactctta gaggcatcta   1980
aagctggaga cttggaaact gtgaagcaac tttgcagctc tcaaaatgtg aattgtagag   2040
acttagaggg ccggcattcc acgcccttac acttcgcagc aggctacaac cgcgtgtctg   2100
ttgtagagta cctgctacac cacggtgccg atgtccatgc caaagacaag ggtggcttgg   2160
tgccccttca taatgcctgt tcatatggac actatgaggt ggctgagctt ttagtaaggc   2220
atggggcttc tgtcaatgtg gcggacttat ggaaatttac ccctctccat gaagcagcag   2280
ctaaaggaaa gtatgaaatc tgcaagctcc ttttaaaaca tggagcagat ccaactaaaa   2340
agaacagaga tggaaataca cctttggatt tggtaaagga aggagacaca gatattcagg   2400
acttactgag aggggatgct gctttgttgg atgctgccaa gaagggctgc ctggcaagag   2460
tgcagaagct ctgtacccca gagaatatca actgcagaga cacccagggc agaaattcaa   2520
cccctctgca cctggcagca ggctataata acctggaagt agctgaatat cttctagagc   2580
atggagctga tgttaatgcc caggacaagg gtggtttaat tcctcttcat aatgcggcat   2640
cttatgggca tgttgacata gcggctttat tgataaaata caacacgtgt gtaaatgcaa   2700
cagataagtg ggcgtttact cccctccatg aagcagccca gaaaggaagg acgcagctgt   2760
gcgccctcct cctagcgcat ggtgcagacc ccaccatgaa gaaccaggaa ggccagacgc   2820
ctctggatct ggcaacagct gacgatatca gagctttgct gatagatgcc atgcccccag   2880
aggccttacc tacctgtttt aaacctcagg ctactgtagt gagtgcctct ctgatctcac   2940
cagcatccac cccctcctgc ctctcggctg ccagcagcat agacaacctc actggccctt   3000
tagcagagtt ggccgtagga ggagcctcca atgcagggga tggcgccgcg ggaacagaaa   3060
ggaaggaagg agaagttgct ggtcttgaca tgaatatcag ccaatttcta aaaagccttg   3120
gccttgaaca ccttcgggat atctttgaaa cagaacagat tacactagat gtgttggctg   3180
atatgggtca tgaagagttg aaagaaatag gcatcaatgc atatgggcac cgccacaaat   3240
taatcaaagg agtagaaaga ctcttaggtg gacaacaagg caccaatcct tatttgactt   3300
ttcactgtgt taatcaggga acgattttgc tggatcttgc tccagaagat aaagaatatc   3360
```

```
agtcagtgga agaagagatg caaagtacta ttcgagaaca cagagatggt ggtaatgctg   3420
gcggcatctt caacagatac aatgtcattc gaattcaaaa agttgtcaac aagaagttga   3480
gggagcggtt ctgccaccga cagaaggaag tgtctgagga gaatcacaac catcacaatg   3540
agcgcatgtt gtttcatggt tctcctttca ttaatgccat tattcataaa gggtttgatg   3600
agcgacatgc atacatagga ggaatgtttg ggccgggat ttattttgct gaaaactcct    3660
caaaaagcaa ccaatatgtt tatggaattg gaggaggaac aggctgccct acacacaagg   3720
acaggtcatg ctatatatgt cacagacaaa tgctcttctg tagagtgacc cttgggaaat   3780
cctttctgca gtttagcacc atgaaaatgg cccacgcgcc tccagggcac cactcagtca   3840
ttggtagacc gagcgtcaat gggctggcat atgctgaata tgtcatctac agaggagaac   3900
aggcataccc agagtatctt atcacttacc agatcatgaa gccagaagcc ccttcccaga   3960
ccgcaacagc cgcagagcag aagacctagt gaatgcctgc tggtgaaggc cagatcagat   4020
ttcaacctgg gactggatta cagaggattg tttctaataa caacatcaat attctagaag   4080
tccctgacag cctagaaata agctgtttgt cttctataaa gcattgctat agtgatgaat   4140
agtatgagta actgatacat actcaactgc tactgttccc tttgaggaaa tgtttacagg   4200
ggcggccttt taacatatct caggctcatt ttcattgcaa ttatccattt ctaaaacaag   4260
attgcttcga tctagacttg gaaatggaaa ataagaaaac caatgctttt tcaaatgttc   4320
acaattcaca cactacattt gttttgttat gcatgacgtg tctataacaa atatacacat   4380
acgacaggca acaagcttgt ttttgatttg ccagacatgc atcattggct attgtttgtt   4440
tgtttttttgt tttttgtgt tttttgggtt actttgaaaa tgagccagag ccttcttgag   4500
gatattttgc acaaagtcac gctgacaaaa tcattagcag tgcaacccaa gcttctggct   4560
gagcaagatt cagtttccac tttttaaaat tttttttattt tgctctgtag ctgcacttct   4620
cgttatcata aattgagatg aaaaggaaaa aacatcaagt tttagtacct ttttatgaat   4680
tggcctatct tacaagagaa gggcacaaac accaacctga cttaggaacg cctaaattca   4740
gagaagtcaa agccggtgaa ggccacttgc tctttccaac acaagcctgc cacagaggtc   4800
ttcgggacag tactggagat gcaggttgac acgggcttga gttccaaggt gaaaaaactg   4860
gggaggctgt gaaggaagag ctgcattaag gagggtgagg agcgtgtggt tctgtatcat   4920
ggcagcccca atggatccag gggatgcctc caaaaaatac atgcttccct tcccttaatc   4980
tgtactgttg ggattgttac ccctccaaat tagctgcctt atttcaaaag tcagtgaaat   5040
tactgcactt gatgagggtc acaaaaatac cacttgattg tttctttagt tgagaatgct   5100
gggattcaga ctcgaatagt ggatagatac acacaaatgc aaggactttt ttgtttactc   5160
cagatttggg gtttattttg agtggcatgc ttcaaatagt tcataaagat ccttgcatta   5220
aatttctgaa ccatttcttc aaacttctta gtgtgtttag acaaggagaa caaaaattga   5280
aaccaaagcc ctttctgtta ttttttcaat gaaggtgaga aagaaatacc atacaatttt   5340
ctttgtgaaa ttactgttta ttttcatcaa catttaccaa gtgccattga catttataaa   5400
aaaaaatgat cctttatagt tcttacactt gcccttttca ccttaactga atatgaattg   5460
agtgcactaa cttatttact tgatatactg tgcatctact ctgctttgaa gcgaaagaaa   5520
tataaacacg aggaggaata ggaaagacag tgtgacacaa acttgccatt gcaattcaaa   5580
gccctgaaaa cgatgggttt aatgcaaggt gattaagctg tgacctcctt taatctcctg   5640
aagcaaaata aaatggttac atgcaaaact tctagaaata gactcttaaa atatatacat   5700
tttgctttga ttttggcttc aacccagtgc tggaactagg catccagact agtttgaatg   5760
```

```
tttgtagctg aatttttatg ggtcctcaaa attaaatcga gaattagcct cagttgttgc   5820
ttcttttgaa gtttcagtga cccaagctgg gtgtttgtgt cttggctact tgtttaatag   5880
cactagaatt ccaggtgaag ctttgagagt tgatattcat taagagggct tttttcccc   5940
ttctttcctt ctcttttgct gtaacaaagg gttgaagaaa ttgccatctg tgtagttttc   6000
agtagctgtc aagtgtgtct tacttacctt cccccagacg tagtttaaaa tggtaaacac   6060
agctgtgatt tttagttaag taaaagagtt aatatgatat agatatggaa agctttatgg   6120
cttcattaaa aagataaacc actacctaac tgtggttgta tgttgtttcc atcatactaa   6180
ctagatgaat ggatgcgcca gttttcatct tggtccttac acttgagaag ttaaactgtg   6240
gttcagtatt taaactgcca gtgttatacg tctcatgctc tgtgtgccag gtgaaggtac   6300
tgtgtaagga agacatttgc ggtgcttctt gtcctataat gattcaagta tatagtagtt   6360
cttgaaagag tgtgcatata ttactcatct gcttaagaga gtgggttaat ggatatatca   6420
gaggagccaa atacattttt ttcagaactt gaaaaccaaa ggtcatcatg agtgcactca   6480
aaagttagga caagtttatt acatttggga ttttcatctg tagccgtatg aagaaccctt   6540
tccaatataa aagcatggca ttaaattagg ctgaagtctt ttattttttg tatatgtact   6600
atatagaaat actagcaagt taggatcatc caatatggcc taccccgaaa tggcccctct   6660
gtttccctaa ccacatggaa gaaagaatct gaacgtctcc accggctcta cccgagttcc   6720
aaaactaaag ggcttctcca gacctgatgg ttccagttta cctgctgttg gcctgctgga   6780
tacttgactc aggcataaat taagtgccct ggtcccgaac tttctccctg tatttgacct   6840
ccttccctct ttcctaaatt actagtctgg aattaaaatt agctccagca atgacctttg   6900
actccattca ttttctcctc atcttgggtc ttaaaaaagg agaccagata cctcctagct   6960
tttgtatcac aaccaggaat gggtattagg cctcatgcgc tttgctcaga acactgccgc   7020
tttgttaaca aatgacagca tggaacccag agttttgatt cgatgcaaaa taacagcagt   7080
gcaaccagga ttcttgtttt ccttttcctt cttggagttt ggaatttcta gcttttcaag   7140
cagcataagt agaatcaaca ttaggatgtt ttcatgaaat agcatcctta tacttctttg   7200
agcttgatgt tagtggctag actgatttcc ctttgctctc aaaatacaaa gtgcattgaa   7260
gtatacagag aaatgcctga atatggcaag caaataatgt agattaacat tctattattg   7320
tatccgtttt acaaaaaata aaattttgat atatgccgga gaacggcatt agaatgcaat   7380
aagttgtcta ggtttttctg tttcagtgtc tctcccaatg gcacgaaggg ttattgggca   7440
ttgtccccac ccccgccttt ttaacatgtg cactatctgg attcctgtaa atggccttgc   7500
aaacagaagt ggtgtgtatt ttcaagcacc tttcccccat tgtatccgaa tccctcttgt   7560
gtgatatctg tgacaaatag ccttcttctt gtgttttctg ttggactaat tgtctcacgt   7620
aaagctatag accttactaa tttggcaggt attcaaaact gccattaaga taggatttca   7680
tgtcagatac gtatttaaag agtaaagtca aatttgttta atgtcagatc agtgacagaa   7740
gtgaaaagaa agtaattgtg aaagtgatgt ttgagctatt gtacacatct agcatatgga   7800
aagcaaatgc actcgaaaac tactattcta gaacatgagg cttcttcagc aacttgtgca   7860
ctctgccatt aataaattaa atttttcccc tctagaaagc cttaactatg gcggaaactt   7920
tttaaccttt tatattttaa taaataaaac attgtagtcc catttcttag tgtttgaaag   7980
gtgtgtcagt gagtcggcca tgtctccatg tgtttcagac ctgttcatct tattttatga   8040
tggtatattt cataagtaat attcccttac atgcaatgga gctgattaaa attaatccat   8100
```

```
ttcaatttct ccatattgga acttcctcag ctaccagatt tctggtttgg agaagtgctg   8160

gaaagatttc aaagcctatt cagttgtgta tgtggggata cgacagcaac tgtgatacct   8220

tgtagaatat gagtgatatg caagctgtgt tttttaattg ttttaaaatg taaattatgg   8280

ttatgctaaa gtgaaaacct agaggaagct aatgatttta tatactttgc acgaccaaat   8340

atggtcgtag tatgacgagt tttatacatt gccagagagt tctgcctcct ctgaaataac   8400

attcgcactg tagattgcat ttcggctttt cctcctttca cattcttttt tgctttacac   8460

ttcacgtctt cgcacctgcc ctacctccca tcctttcaaa gaggtttctt tcacgttcca   8520

gaattcagat tgttctgtga tttcttttac atcagtctac ccatttctgc aggcagccct   8580

gaaagccctt gtgttgattc agagtgtttg cagagaaatg cagttgaacc ctggtagtgg   8640

ggtgtccctc acacacccgc gcacccctcc caaagttcag gatgaaaggc tagaaaaccc   8700

attcaaagtt aggaaagaac acagatcttt gaggccgata gcctagacct agaagatgac   8760

cttgagtatg taaacattgt ctccgtgaca caaaacactg aaactcttca tgtgcatata   8820

acacctgctt ctgctcccat tgtttcaagc tcatcttatc tttgtagtag taatgtttgt   8880

ctttgatacc tacaaactaa aaaggtactt ttatcaaggt ttctcaaaac atttacaaaa   8940

ccagctttga gaaaatgtta tgttgcctgg caacagcact cggagtagta attgtgtttt   9000

ctcattgtga tgttggtctg tgtgagcaac cagtgtagtg actctttggt tcattattcg   9060

tgttgttttt atttttagtc tctgtgtgac ccaacagtgg caggggttac aacccccctct   9120

cctttctttt ttgtatttat ctatttgtag gattgtcaga tcaagtacaa gatgcccagt   9180

taagtttgaa tttcagagaa acaatttcac gttaagaatg tttcatgcaa tatttggcat   9240

atatttacag taaaagcatt cattatttgt ctgaaattca aatttaactg agcatgctgg   9300

tttttctcat tgtttggttt ttctaaatct ggcaatccta cagctgtggt catgggaaat   9360

cacctacagc atgttaaagt cctctagtca tcatctcgtc acctgaaatg gaagtccttt   9420

ttccctcacc ctccacttct ttccaaagga gggcatcaag gaacttaacc tgcctgcctg   9480

gtgggtttct atttaagaca tctttgtgat tatatttaac ctgcaattgt gctttggctt   9540

aatgtctagc tcactgtact tgtaaatgat taatattcaa taaaaccatt tttaaagta    9599
```

<210> SEQ ID NO 10
<211> LENGTH: 1327
<212> TYPE: PRT
<213> ORGANISM: Homo sapiens

<400> SEQUENCE: 10

```
Met Ala Ala Ser Arg Arg Ser Gln His His His His His His Gln Gln
1               5                   10                  15

Gln Leu Gln Pro Ala Pro Gly Ala Ser Ala Pro Pro Pro Pro Pro Pro
            20                  25                  30

Pro Pro Leu Ser Pro Gly Leu Ala Pro Gly Thr Thr Pro Ala Ser Pro
        35                  40                  45

Thr Ala Ser Gly Leu Ala Pro Phe Ala Ser Pro Arg His Gly Leu Ala
    50                  55                  60

Leu Pro Glu Gly Asp Gly Ser Arg Asp Pro Pro Asp Arg Pro Arg Ser
65                  70                  75                  80

Pro Asp Pro Val Asp Gly Thr Ser Cys Cys Ser Thr Thr Ser Thr Ile
                85                  90                  95

Cys Thr Val Ala Ala Ala Pro Val Val Pro Ala Val Ser Thr Ser Ser
            100                 105                 110
```

```
Ala Ala Gly Val Ala Pro Asn Pro Ala Gly Ser Gly Ser Asn Asn Ser
        115                 120                 125

Pro Ser Ser Ser Ser Ser Pro Thr Ser Ser Ser Ser Ser Ser Pro Ser
    130                 135                 140

Ser Pro Gly Ser Ser Leu Ala Glu Ser Pro Glu Ala Ala Gly Val Ser
145                 150                 155                 160

Ser Thr Ala Pro Leu Gly Pro Gly Ala Ala Gly Pro Gly Thr Gly Val
                165                 170                 175

Pro Ala Val Ser Gly Ala Leu Arg Glu Leu Leu Glu Ala Cys Arg Asn
            180                 185                 190

Gly Asp Val Ser Arg Val Lys Arg Leu Val Asp Ala Ala Asn Val Asn
        195                 200                 205

Ala Lys Asp Met Ala Gly Arg Lys Ser Ser Pro Leu His Phe Ala Ala
    210                 215                 220

Gly Phe Gly Arg Lys Asp Val Val Glu His Leu Leu Gln Met Gly Ala
225                 230                 235                 240

Asn Val His Ala Arg Asp Asp Gly Gly Leu Ile Pro Leu His Asn Ala
                245                 250                 255

Cys Ser Phe Gly His Ala Glu Val Val Ser Leu Leu Leu Cys Gln Gly
            260                 265                 270

Ala Asp Pro Asn Ala Arg Asp Asn Trp Asn Tyr Thr Pro Leu His Glu
        275                 280                 285

Ala Ala Ile Lys Gly Lys Ile Asp Val Cys Ile Val Leu Leu Gln His
    290                 295                 300

Gly Ala Asp Pro Asn Ile Arg Asn Thr Asp Gly Lys Ser Ala Leu Asp
305                 310                 315                 320

Leu Ala Asp Pro Ser Ala Lys Ala Val Leu Thr Gly Glu Tyr Lys Lys
                325                 330                 335

Asp Glu Leu Leu Glu Ala Ala Arg Ser Gly Asn Glu Glu Lys Leu Met
            340                 345                 350

Ala Leu Leu Thr Pro Leu Asn Val Asn Cys His Ala Ser Asp Gly Arg
        355                 360                 365

Lys Ser Thr Pro Leu His Leu Ala Ala Gly Tyr Asn Arg Val Arg Ile
    370                 375                 380

Val Gln Leu Leu Leu Gln His Gly Ala Asp Val His Ala Lys Asp Lys
385                 390                 395                 400

Gly Gly Leu Val Pro Leu His Asn Ala Cys Ser Tyr Gly His Tyr Glu
                405                 410                 415

Val Thr Glu Leu Leu Leu Lys His Gly Ala Cys Val Asn Ala Met Asp
            420                 425                 430

Leu Trp Gln Phe Thr Pro Leu His Glu Ala Ala Ser Lys Asn Arg Val
        435                 440                 445

Glu Val Cys Ser Leu Leu Leu Ser His Gly Ala Asp Pro Thr Leu Val
    450                 455                 460

Asn Cys His Gly Lys Ser Ala Val Asp Met Ala Pro Thr Pro Glu Leu
465                 470                 475                 480

Arg Glu Arg Leu Thr Tyr Glu Phe Lys Gly His Ser Leu Leu Gln Ala
                485                 490                 495

Ala Arg Glu Ala Asp Leu Ala Lys Val Lys Lys Thr Leu Ala Leu Glu
            500                 505                 510

Ile Ile Asn Phe Lys Gln Pro Gln Ser His Glu Thr Ala Leu His Cys
        515                 520                 525

Ala Val Ala Ser Leu His Pro Lys Arg Lys Gln Val Thr Glu Leu Leu
```

```
    530                 535                 540

Leu Arg Lys Gly Ala Asn Val Asn Glu Lys Asn Lys Asp Phe Met Thr
545                 550                 555                 560

Pro Leu His Val Ala Ala Glu Arg Ala His Asn Asp Val Met Glu Val
                565                 570                 575

Leu His Lys His Gly Ala Lys Met Asn Ala Leu Asp Thr Leu Gly Gln
            580                 585                 590

Thr Ala Leu His Arg Ala Ala Leu Ala Gly His Leu Gln Thr Cys Arg
        595                 600                 605

Leu Leu Leu Ser Tyr Gly Ser Asp Pro Ser Ile Ile Ser Leu Gln Gly
    610                 615                 620

Phe Thr Ala Ala Gln Met Gly Asn Glu Ala Val Gln Gln Ile Leu Ser
625                 630                 635                 640

Glu Ser Thr Pro Ile Arg Thr Ser Asp Val Asp Tyr Arg Leu Leu Glu
                645                 650                 655

Ala Ser Lys Ala Gly Asp Leu Glu Thr Val Lys Gln Leu Cys Ser Ser
            660                 665                 670

Gln Asn Val Asn Cys Arg Asp Leu Glu Gly Arg His Ser Thr Pro Leu
        675                 680                 685

His Phe Ala Ala Gly Tyr Asn Arg Val Ser Val Val Glu Tyr Leu Leu
    690                 695                 700

His His Gly Ala Asp Val His Ala Lys Asp Lys Gly Gly Leu Val Pro
705                 710                 715                 720

Leu His Asn Ala Cys Ser Tyr Gly His Tyr Glu Val Ala Glu Leu Leu
                725                 730                 735

Val Arg His Gly Ala Ser Val Asn Val Ala Asp Leu Trp Lys Phe Thr
            740                 745                 750

Pro Leu His Glu Ala Ala Ala Lys Gly Lys Tyr Glu Ile Cys Lys Leu
        755                 760                 765

Leu Leu Lys His Gly Ala Asp Pro Thr Lys Lys Asn Arg Asp Gly Asn
    770                 775                 780

Thr Pro Leu Asp Leu Val Lys Glu Gly Asp Thr Asp Ile Gln Asp Leu
785                 790                 795                 800

Leu Arg Gly Asp Ala Ala Leu Leu Asp Ala Ala Lys Lys Gly Cys Leu
                805                 810                 815

Ala Arg Val Gln Lys Leu Cys Thr Pro Glu Asn Ile Asn Cys Arg Asp
            820                 825                 830

Thr Gln Gly Arg Asn Ser Thr Pro Leu His Leu Ala Ala Gly Tyr Asn
        835                 840                 845

Asn Leu Glu Val Ala Glu Tyr Leu Leu Glu His Gly Ala Asp Val Asn
    850                 855                 860

Ala Gln Asp Lys Gly Gly Leu Ile Pro Leu His Asn Ala Ala Ser Tyr
865                 870                 875                 880

Gly His Val Asp Ile Ala Ala Leu Leu Ile Lys Tyr Asn Thr Cys Val
                885                 890                 895

Asn Ala Thr Asp Lys Trp Ala Phe Thr Pro Leu His Glu Ala Ala Gln
            900                 905                 910

Lys Gly Arg Thr Gln Leu Cys Ala Leu Leu Leu Ala His Gly Ala Asp
        915                 920                 925

Pro Thr Met Lys Asn Gln Glu Gly Gln Thr Pro Leu Asp Leu Ala Thr
    930                 935                 940

Ala Asp Asp Ile Arg Ala Leu Leu Ile Asp Ala Met Pro Pro Glu Ala
945                 950                 955                 960
```

```
Leu Pro Thr Cys Phe Lys Pro Gln Ala Thr Val Val Ser Ala Ser Leu
                965                 970                 975

Ile Ser Pro Ala Ser Thr Pro Ser Cys Leu Ser Ala Ala Ser Ser Ile
            980                 985                 990

Asp Asn Leu Thr Gly Pro Leu Ala  Glu Leu Ala Val Gly  Gly Ala Ser
        995                 1000                 1005

Asn Ala  Gly Asp Gly Ala Ala  Gly Thr Glu Arg Lys  Glu Gly Glu
    1010                 1015                 1020

Val Ala  Gly Leu Asp Met Asn  Ile Ser Gln Phe Leu  Lys Ser Leu
    1025                 1030                 1035

Gly Leu  Glu His Leu Arg Asp  Ile Phe Glu Thr Glu  Gln Ile Thr
    1040                 1045                 1050

Leu Asp  Val Leu Ala Asp Met  Gly His Glu Glu Leu  Lys Glu Ile
    1055                 1060                 1065

Gly Ile  Asn Ala Tyr Gly His  Arg His Lys Leu Ile  Lys Gly Val
    1070                 1075                 1080

Glu Arg  Leu Leu Gly Gly Gln  Gln Gly Thr Asn Pro  Tyr Leu Thr
    1085                 1090                 1095

Phe His  Cys Val Asn Gln Gly  Thr Ile Leu Leu Asp  Leu Ala Pro
    1100                 1105                 1110

Glu Asp  Lys Glu Tyr Gln Ser  Val Glu Glu Glu Met  Gln Ser Thr
    1115                 1120                 1125

Ile Arg  Glu His Arg Asp Gly  Gly Asn Ala Gly Gly  Ile Phe Asn
    1130                 1135                 1140

Arg Tyr  Asn Val Ile Arg Ile  Gln Lys Val Val Asn  Lys Lys Leu
    1145                 1150                 1155

Arg Glu  Arg Phe Cys His Arg  Gln Lys Glu Val Ser  Glu Glu Asn
    1160                 1165                 1170

His Asn  His His Asn Glu Arg  Met Leu Phe His Gly  Ser Pro Phe
    1175                 1180                 1185

Ile Asn  Ala Ile Ile His Lys  Gly Phe Asp Glu Arg  His Ala Tyr
    1190                 1195                 1200

Ile Gly  Gly Met Phe Gly Ala  Gly Ile Tyr Phe Ala  Glu Asn Ser
    1205                 1210                 1215

Ser Lys  Ser Asn Gln Tyr Val  Tyr Gly Ile Gly Gly  Gly Thr Gly
    1220                 1225                 1230

Cys Pro  Thr His Lys Asp Arg  Ser Cys Tyr Ile Cys  His Arg Gln
    1235                 1240                 1245

Met Leu  Phe Cys Arg Val Thr  Leu Gly Lys Ser Phe  Leu Gln Phe
    1250                 1255                 1260

Ser Thr  Met Lys Met Ala His  Ala Pro Pro Gly His  His Ser Val
    1265                 1270                 1275

Ile Gly  Arg Pro Ser Val Asn  Gly Leu Ala Tyr Ala  Glu Tyr Val
    1280                 1285                 1290

Ile Tyr  Arg Gly Glu Gln Ala  Tyr Pro Glu Tyr Leu  Ile Thr Tyr
    1295                 1300                 1305

Gln Ile  Met Lys Pro Glu Ala  Pro Ser Gln Thr Ala  Thr Ala Ala
    1310                 1315                 1320

Glu Gln  Lys Thr
    1325
```

<210> SEQ ID NO 11
<211> LENGTH: 6274

<212> TYPE: DNA
<213> ORGANISM: Homo sapiens

<400> SEQUENCE: 11

```
ggctggacgg agctggcagg aggggccttg ccagcttccg ccgccgcgtc gtttcaggac     60
ccggacggcg gattcgcgct gcctccgccg ccgcggggca gccgggggc agggagccca    120
gcgaggggcg cgcgtgggcg cggccatggg actgcgccgg atccggtgac agcagggagc    180
caagcggccc gggccctgag cgcgtcttct ccgggggcc tcgccctcct gctcgcgggg    240
ccggggctcc tgctccggtt gctggcgctg ttgctggctg tggcggcggc caggatcatg    300
tcgggtcgcc gctgcgccgg cgggggagcg gcctgcgcga gcgccgcggc cgaggccgtg    360
gagccggccg cccgagagct gttcgaggcg tgccgcaacg gggacgtgga acgagtcaag    420
aggctggtga cgcctgagaa ggtgaacagc cgcgacacgg cgggcaggaa atccaccccg    480
ctgcacttcg ccgcaggttt tgggcggaaa gacgtagttg aatatttgct tcagaatggt    540
gcaaatgtcc aagcacgtga tgatgggggc cttattcctc ttcataatgc atgctctttt    600
ggtcatgctg aagtagtcaa tctccttttg cgacatggtg cagaccccaa tgctcgagat    660
aattggaatt atactcctct ccatgaagct gcaattaaag gaaagattga tgtttgcatt    720
gtgctgttac agcatggagc tgagccaacc atccgaaata cagatggaag gacagcattg    780
gatttagcag atccatctgc caaagcagtg cttactggtg aatataagaa agatgaactc    840
ttagaaagtg ccaggagtgg caatgaagaa aaaatgatgg ctctactcac accattaaat    900
gtcaactgcc acgcaagtga tggcagaaag tcaactccat tacatttggc agcaggatat    960
aacagagtaa agattgtaca gctgttactg caacatggag ctgatgtcca tgctaaagat   1020
aaaggtgatc tggtaccatt acacaatgcc tgttcttatg gtcattatga agtaactgaa   1080
cttttggtca agcatggtgc ctgtgtaaat gcaatggact tgtggcaatt cactcctctt   1140
catgaggcag cttctaagaa cagggttgaa gtatgttctc ttctcttaag ttatggtgca   1200
gacccaacac tgctcaattg tcacaataaa agtgctatag acttggctcc cacaccacag   1260
ttaaaagaaa gattagcata tgaatttaaa ggccactcgt tgctgcaagc tgcacgagaa   1320
gctgatgtta ctcgaatcaa aaaacatctc tctctggaaa tggtgaattt caagcatcct   1380
caaacacatg aaacagcatt gcattgtgct gctgcatctc catatcccaa aagaaagcaa   1440
atatgtgaac tgttgctaag aaaaggagca aacatcaatg aaaagactaa agaattcttg   1500
actcctctgc acgtggcatc tgagaaagct cataatgatg ttgttgaagt agtggtgaaa   1560
catgaagcaa aggttaatgc tctggataat cttggtcaga cttctctaca cagagctgca   1620
tattgtggtc atctacaaac ctgccgccta ctcctgagct atgggtgtga tcctaacatt   1680
atatcccttc agggctttac tgctttacag atgggaaatg aaaatgtaca gcaactcctc   1740
caagagggta tctcattagg taattcagag gcagacagac aattgctgga agctgcaaag   1800
gctggagatg tcgaaactgt aaaaaaactg tgtactgttc agagtgtcaa ctgcagagac   1860
attgaagggc gtcagtctac accacttcat tttgcagctg ggtataacag agtgtccgtg   1920
gtggaatatc tgctacagca tggagctgat gtgcatgcta aagataaagg aggccttgta   1980
cctttgcaca atgcatgttc ttatggacat tatgaagttg cagaacttct tgttaaacat   2040
ggagcagtag ttaatgtagc tgatttatgg aaatttacac ctttacatga agcagcagca   2100
aaaggaaaat atgaaatttg caaacttctg ctccagcatg gtgcagaccc tacaaaaaaa   2160
aacagggatg gaaatactcc tttggatctt gttaaagatg gagatacaga tattcaagat   2220
```

-continued

```
ctgcttaggg gagatgcagc tttgctagat gctgccaaga agggttgttt agccagagtg   2280
aagaagttgt cttctcctga taatgtaaat tgccgcgata cccaaggcag acattcaaca   2340
cctttacatt tagcagctgg ttataataat ttagaagttg cagagtattt gttacaacac   2400
ggagctgatg tgaatgccca agacaaagga ggacttattc ctttacataa tgcagcatct   2460
tacgggcatg tagatgtagc agctctacta ataaagtata atgcatgtgt caatgccacg   2520
gacaaatggg ctttcacacc tttgcacgaa gcagcccaaa agggacgaac acagctttgt   2580
gctttgttgc tagcccatgg agctgacccg actcttaaaa atcaggaagg acaaacacct   2640
ttagatttag tttcagcgga tgatgtcagc gctcttctga cagcagccat gcccccatct   2700
gctctgccct cttgttacaa gcctcaagtg ctcaatggtg tgagaagccc aggagccact   2760
gcagatgctc tctcttcagg tccatctagc ccatcaagcc tttctgcagc cagcagtctt   2820
gacaacttat ctgggagttt ttcagaactg tcttcagtag ttagttcaag tggaacagag   2880
ggtgcttcca gtttggagaa aaaggaggtt ccaggagtag attttagcat aactcaattc   2940
gtaaggaatc ttggacttga gcacctaatg gatatatttg agagagaaca gatcactttg   3000
gatgtattag ttgagatggg gcacaaggag ctgaaggaga ttggaatcaa tgcttatgga   3060
cataggcaca aactaattaa aggagtcgag agacttatct ccggacaaca aggtcttaac   3120
ccatatttaa ctttgaacac ctctggtagt ggaacaattc ttatagatct gtctcctgat   3180
gataaagagt ttcagtctgt ggaggaagag atgcaaagta cagttcgaga gcacagagat   3240
ggaggtcatg caggtggaat cttcaacaga tacaatattc tcaagattca gaaggtttgt   3300
aacaagaaac tatgggaaag atacactcac cggagaaaag aagtttctga agaaaaccac   3360
aaccatgcca atgaacgaat gctatttcat gggtctcctt ttgtgaatgc aattatccac   3420
aaaggctttg atgaaaggca tgcgtacata ggtggtatgt ttggagctgg catttatttt   3480
gctgaaaact cttccaaaag caatcaatat gtatatggaa ttggaggagg tactgggtgt   3540
ccagttcaca aagacagatc ttgttacatt tgccacaggc agctgctctt ttgccgggta   3600
accttgggaa agtctttcct gcagttcagt gcaatgaaaa tggcacattc tcctccaggt   3660
catcactcag tcactggtag gcccagtgta aatggcctag cattagctga atatgttatt   3720
tacagaggag aacaggctta tcctgagtat ttaattactt accagattat gaggcctgaa   3780
ggtatggtcg atggataaat agttatttta agaaactaat tccactgaac ctaaaatcat   3840
caaagcagca gtggcctcta cgttttactc ctttgctgaa aaaaaatcat cttgcccaca   3900
ggcctgtggc aaaaggataa aaatgtgaac gaagtttaac attctgactt gataaagctt   3960
taataatgta cagtgttttc taaatatttc ctgtttttc agcactttaa cagatgccat   4020
tccaggttaa actgggttgt ctgtactaaa ttataaacag agttaacttg aaccttttat   4080
atgttatgca ttgattctaa caaactgtaa tgccctcaac agaactaatt ttactaatac   4140
aatactgtgt tctttaaaac acagcattta cactgaatac aatttcattt gtaaaactgt   4200
aaataagagc ttttgtacta gcccagtatt tatttacatt gctttgtaat ataaatctgt   4260
tttagaactg cagcggttta caaaattttt tcatatgtat tgttcatcta tacttcatct   4320
tacatcgtca tgattgagtg atctttacat ttgattccag aggctatgtt cagttgttag   4380
ttgggaaaga ttgagttatc agatttaatt tgccgatggg agcctttatc tgtcattaga   4440
aatctttctc atttaagaac ttatgaatat gctgaagatt taatttgtga tacctttgta   4500
tgtatgagac acattccaaa gagctctaac tatgataggt cctgattact aaagaagctt   4560
ctttactggc ctcaatttct agctttcatg ttggaaaatt ttctgcagtc cttctgtgaa   4620
```

aattagagca aagtgctcct gtttttaga gaaactaaat cttgctgttg aacaattatt 4680
gtgttctttt catggaacat aagtaggatg ttacatttcc agggtgggaa gggtaatcct 4740
aaatcatttc ccaatctatt ctaattacct taaatctaaa ggggaaaaaa aaaatcacaa 4800
acaggactgg gtagtttttt atcctaagta tattttttcc tgttcttttt acttggtttt 4860
attgctgtat ttatagccaa tctatacatc atgggtaaac ttaacccaga actataaaat 4920
gtagttgtct cagtcccctc caggcctcct gaatgggcaa gtgcagtgaa acaggtgctt 4980
cttgctcctg ggtttctct ccatgatgtt atgcccaatt ggaaatatgc tgtcagtttg 5040
tgcaccatat ggtgaccacg cctgtgctca gtttggcagc tatagaagga aatgctgtcc 5100
cataaaatgc cattcctatt ttctaatata aaactctttt ccaggaagca tgcttaagca 5160
tcttgttaca gagacataca tccattatgg cttggcaatc tcttttattt gttgactcta 5220
gctcccttca aagtcgagga aagatcttta ctcacttaat gaggacattc cccatcactg 5280
tctgtaccag ttcaccttta ttttacgttt tattcagtct gtaaattaac tggccctttg 5340
cagtaacttg tacataaagt gctagaaaat catgttcctt gtcctgagta agagttaatc 5400
agagtaaatg catttctgga gttgtttctg tgatgtaaat tatgatcatt atttaagaag 5460
tcaaatcctg atcttgaagt gctttttata cagctctcta ataattacaa atatccgaaa 5520
gtcatttctt ggaacacaag tggagtatgc caaattttat atgaattttt cagattatct 5580
aagcttccag gttttataat tagaagataa tgagagaatt aatggggttt atatttacat 5640
tatctctcaa ctatgtagcc catattactc accctatgag tgaatctgga attgcttttc 5700
atgtgaaatc attgtggtct atgagtttac aatactgcaa actgtgttat tttatctaat 5760
ccattgctta atgagtgtgt ttttccatga atgaatatac cgtggttcat atgttagcat 5820
ggcagcattt tcagatagct ttttgtttgt tgggaagttg gggttttggg gggagggggga 5880 gtattagtac gttgcatgaa atagcttact ttataatgat ggaattgctt tttcttttgt 5940
cttgtgattt tttttttga agtgaaattt aactttttgt gcaagtagta ctattatacc 6000
catcttcagt gtcttacttg tactgtatca cattccatac cctcatttaa ttcttaataa 6060
aactgttcac ttgtttttct gggtagcatg gtaattactg gaatagtata aatgtgttga 6120
atggtctttg agaaaatgaa ttaagattac aataaaccac aattgcagga aaacaatgta 6180
gttctgagtc taatagtgat aaagaatgca gtttgaagtt tgaaatattg aatattgtag 6240
ctgtacttgc tcattaaaat gaaagtagct gtga 6274

<210> SEQ ID NO 12
<211> LENGTH: 1166
<212> TYPE: PRT
<213> ORGANISM: Homo sapiens

<400> SEQUENCE: 12

Met Ser Gly Arg Arg Cys Ala Gly Gly Gly Ala Ala Cys Ala Ser Ala
1 5 10 15

Ala Ala Glu Ala Val Glu Pro Ala Ala Arg Glu Leu Phe Glu Ala Cys
20 25 30

Arg Asn Gly Asp Val Glu Arg Val Lys Arg Leu Val Thr Pro Glu Lys
35 40 45

Val Asn Ser Arg Asp Thr Ala Gly Arg Lys Ser Thr Pro Leu His Phe
50 55 60

Ala Ala Gly Phe Gly Arg Lys Asp Val Val Glu Tyr Leu Leu Gln Asn
65 70 75 80

```
Gly Ala Asn Val Gln Ala Arg Asp Asp Gly Gly Leu Ile Pro Leu His
                85                  90                  95

Asn Ala Cys Ser Phe Gly His Ala Glu Val Val Asn Leu Leu Leu Arg
            100                 105                 110

His Gly Ala Asp Pro Asn Ala Arg Asp Asn Trp Asn Tyr Thr Pro Leu
        115                 120                 125

His Glu Ala Ala Ile Lys Gly Lys Ile Asp Val Cys Ile Val Leu Leu
    130                 135                 140

Gln His Gly Ala Glu Pro Thr Ile Arg Asn Thr Asp Gly Arg Thr Ala
145                 150                 155                 160

Leu Asp Leu Ala Asp Pro Ser Ala Lys Ala Val Leu Thr Gly Glu Tyr
                165                 170                 175

Lys Lys Asp Glu Leu Leu Glu Ser Ala Arg Ser Gly Asn Glu Glu Lys
            180                 185                 190

Met Met Ala Leu Leu Thr Pro Leu Asn Val Asn Cys His Ala Ser Asp
        195                 200                 205

Gly Arg Lys Ser Thr Pro Leu His Leu Ala Ala Gly Tyr Asn Arg Val
    210                 215                 220

Lys Ile Val Gln Leu Leu Leu Gln His Gly Ala Asp Val His Ala Lys
225                 230                 235                 240

Asp Lys Gly Asp Leu Val Pro Leu His Asn Ala Cys Ser Tyr Gly His
                245                 250                 255

Tyr Glu Val Thr Glu Leu Leu Val Lys His Gly Ala Cys Val Asn Ala
            260                 265                 270

Met Asp Leu Trp Gln Phe Thr Pro Leu His Glu Ala Ala Ser Lys Asn
        275                 280                 285

Arg Val Glu Val Cys Ser Leu Leu Leu Ser Tyr Gly Ala Asp Pro Thr
    290                 295                 300

Leu Leu Asn Cys His Asn Lys Ser Ala Ile Asp Leu Ala Pro Thr Pro
305                 310                 315                 320

Gln Leu Lys Glu Arg Leu Ala Tyr Glu Phe Lys Gly His Ser Leu Leu
                325                 330                 335

Gln Ala Ala Arg Glu Ala Asp Val Thr Arg Ile Lys Lys His Leu Ser
            340                 345                 350

Leu Glu Met Val Asn Phe Lys His Pro Gln Thr His Glu Thr Ala Leu
        355                 360                 365

His Cys Ala Ala Ala Ser Pro Tyr Pro Lys Arg Lys Gln Ile Cys Glu
    370                 375                 380

Leu Leu Leu Arg Lys Gly Ala Asn Ile Asn Glu Lys Thr Lys Glu Phe
385                 390                 395                 400

Leu Thr Pro Leu His Val Ala Ser Glu Lys Ala His Asn Asp Val Val
                405                 410                 415

Glu Val Val Val Lys His Glu Ala Lys Val Asn Ala Leu Asp Asn Leu
            420                 425                 430

Gly Gln Thr Ser Leu His Arg Ala Ala Tyr Cys Gly His Leu Gln Thr
        435                 440                 445

Cys Arg Leu Leu Leu Ser Tyr Gly Cys Asp Pro Asn Ile Ile Ser Leu
    450                 455                 460

Gln Gly Phe Thr Ala Leu Gln Met Gly Asn Glu Asn Val Gln Gln Leu
465                 470                 475                 480

Leu Gln Glu Gly Ile Ser Leu Gly Asn Ser Glu Ala Asp Arg Gln Leu
                485                 490                 495
```

```
Leu Glu Ala Ala Lys Ala Gly Asp Val Glu Thr Val Lys Lys Leu Cys
            500                 505                 510

Thr Val Gln Ser Val Asn Cys Arg Asp Ile Glu Gly Arg Gln Ser Thr
        515                 520                 525

Pro Leu His Phe Ala Ala Gly Tyr Asn Arg Val Ser Val Val Glu Tyr
    530                 535                 540

Leu Leu Gln His Gly Ala Asp Val His Ala Lys Asp Lys Gly Gly Leu
545                 550                 555                 560

Val Pro Leu His Asn Ala Cys Ser Tyr Gly His Tyr Glu Val Ala Glu
                565                 570                 575

Leu Leu Val Lys His Gly Ala Val Val Asn Val Ala Asp Leu Trp Lys
            580                 585                 590

Phe Thr Pro Leu His Glu Ala Ala Ala Lys Gly Lys Tyr Glu Ile Cys
        595                 600                 605

Lys Leu Leu Leu Gln His Gly Ala Asp Pro Thr Lys Lys Asn Arg Asp
    610                 615                 620

Gly Asn Thr Pro Leu Asp Leu Val Lys Asp Gly Asp Thr Asp Ile Gln
625                 630                 635                 640

Asp Leu Leu Arg Gly Asp Ala Ala Leu Leu Asp Ala Ala Lys Lys Gly
                645                 650                 655

Cys Leu Ala Arg Val Lys Lys Leu Ser Ser Pro Asp Asn Val Asn Cys
            660                 665                 670

Arg Asp Thr Gln Gly Arg His Ser Thr Pro Leu His Leu Ala Ala Gly
        675                 680                 685

Tyr Asn Asn Leu Glu Val Ala Glu Tyr Leu Leu Gln His Gly Ala Asp
    690                 695                 700

Val Asn Ala Gln Asp Lys Gly Gly Leu Ile Pro Leu His Asn Ala Ala
705                 710                 715                 720

Ser Tyr Gly His Val Asp Val Ala Ala Leu Leu Ile Lys Tyr Asn Ala
                725                 730                 735

Cys Val Asn Ala Thr Asp Lys Trp Ala Phe Thr Pro Leu His Glu Ala
            740                 745                 750

Ala Gln Lys Gly Arg Thr Gln Leu Cys Ala Leu Leu Leu Ala His Gly
        755                 760                 765

Ala Asp Pro Thr Leu Lys Asn Gln Glu Gly Gln Thr Pro Leu Asp Leu
    770                 775                 780

Val Ser Ala Asp Asp Val Ser Ala Leu Leu Thr Ala Ala Met Pro Pro
785                 790                 795                 800

Ser Ala Leu Pro Ser Cys Tyr Lys Pro Gln Val Leu Asn Gly Val Arg
                805                 810                 815

Ser Pro Gly Ala Thr Ala Asp Ala Leu Ser Ser Gly Pro Ser Ser Pro
            820                 825                 830

Ser Ser Leu Ser Ala Ala Ser Ser Leu Asp Asn Leu Ser Gly Ser Phe
        835                 840                 845

Ser Glu Leu Ser Ser Val Val Ser Ser Ser Gly Thr Glu Gly Ala Ser
    850                 855                 860

Ser Leu Glu Lys Lys Glu Val Pro Gly Val Asp Phe Ser Ile Thr Gln
865                 870                 875                 880

Phe Val Arg Asn Leu Gly Leu Glu His Leu Met Asp Ile Phe Glu Arg
                885                 890                 895

Glu Gln Ile Thr Leu Asp Val Leu Val Glu Met Gly His Lys Glu Leu
            900                 905                 910

Lys Glu Ile Gly Ile Asn Ala Tyr Gly His Arg His Lys Leu Ile Lys
```

```
        915                 920                 925

Gly Val Glu Arg Leu Ile Ser Gly Gln Gln Gly Leu Asn Pro Tyr Leu
    930                 935                 940

Thr Leu Asn Thr Ser Gly Ser Gly Thr Ile Leu Ile Asp Leu Ser Pro
945                 950                 955                 960

Asp Asp Lys Glu Phe Gln Ser Val Glu Glu Glu Met Gln Ser Thr Val
                965                 970                 975

Arg Glu His Arg Asp Gly Gly His Ala Gly Gly Ile Phe Asn Arg Tyr
            980                 985                 990

Asn Ile Leu Lys Ile Gln Lys Val  Cys Asn Lys Lys Leu  Trp Glu Arg
        995                 1000                1005

Tyr Thr  His Arg Arg Lys Glu  Val Ser Glu Glu Asn  His Asn His
    1010                1015                1020

Ala Asn  Glu Arg Met Leu Phe  His Gly Ser Pro Phe  Val Asn Ala
    1025                1030                1035

Ile Ile  His Lys Gly Phe Asp  Glu Arg His Ala Tyr  Ile Gly Gly
    1040                1045                1050

Met Phe  Gly Ala Gly Ile Tyr  Phe Ala Glu Asn Ser  Ser Lys Ser
    1055                1060                1065

Asn Gln  Tyr Val Tyr Gly Ile  Gly Gly Gly Thr Gly  Cys Pro Val
    1070                1075                1080

His Lys  Asp Arg Ser Cys Tyr  Ile Cys His Arg Gln  Leu Leu Phe
    1085                1090                1095

Cys Arg  Val Thr Leu Gly Lys  Ser Phe Leu Gln Phe  Ser Ala Met
    1100                1105                1110

Lys Met  Ala His Ser Pro Pro  Gly His His Ser Val  Thr Gly Arg
    1115                1120                1125

Pro Ser  Val Asn Gly Leu Ala  Leu Ala Glu Tyr Val  Ile Tyr Arg
    1130                1135                1140

Gly Glu  Gln Ala Tyr Pro Glu  Tyr Leu Ile Thr Tyr  Gln Ile Met
    1145                1150                1155

Arg Pro  Glu Gly Met Val Asp  Gly
    1160                1165
```

<210> SEQ ID NO 13
<211> LENGTH: 38
<212> TYPE: DNA
<213> ORGANISM: Artificial
<220> FEATURE:
<223> OTHER INFORMATION: Primer

<400> SEQUENCE: 13
taagcagcta gcgccacctt ggagggcacg gccggcac 38

<210> SEQ ID NO 14
<211> LENGTH: 48
<212> TYPE: DNA
<213> ORGANISM: Artificial
<220> FEATURE:
<223> OTHER INFORMATION: Primer

<400> SEQUENCE: 14
actatgggat cctcattctt tcaccagcct gtggatgtgg tgctgagc 48

<210> SEQ ID NO 15
<211> LENGTH: 19
<212> TYPE: DNA
<213> ORGANISM: Artificial

<220> FEATURE:
<223> OTHER INFORMATION: Primer

<400> SEQUENCE: 15
ccaatgacaa cgcctcctg 19

<210> SEQ ID NO 16
<211> LENGTH: 19
<212> TYPE: DNA
<213> ORGANISM: Artificial
<220> FEATURE:
<223> OTHER INFORMATION: Primer

<400> SEQUENCE: 16
tggtgcagcc agaaagctc 19

<210> SEQ ID NO 17
<211> LENGTH: 21
<212> TYPE: DNA
<213> ORGANISM: Artificial
<220> FEATURE:
<223> OTHER INFORMATION: Primer

<400> SEQUENCE: 17
agcctcgcat cctatacaac c 21

<210> SEQ ID NO 18
<211> LENGTH: 21
<212> TYPE: DNA
<213> ORGANISM: Artificial
<220> FEATURE:
<223> OTHER INFORMATION: Primer

<400> SEQUENCE: 18
ttctttcaca aggcggcact c 21

<210> SEQ ID NO 19
<211> LENGTH: 21
<212> TYPE: DNA
<213> ORGANISM: Artificial
<220> FEATURE:
<223> OTHER INFORMATION: Primer

<400> SEQUENCE: 19
cacttctagc ccaccctgtg a 21

<210> SEQ ID NO 20
<211> LENGTH: 21
<212> TYPE: DNA
<213> ORGANISM: Artificial
<220> FEATURE:
<223> OTHER INFORMATION: Primer

<400> SEQUENCE: 20
ccacaggttc cgtaatgatt t 21

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
tagccctgcg tagccagtta 20

<210> SEQ ID NO 22
<211> LENGTH: 22
<212> TYPE: DNA
<213> ORGANISM: Artificial
<220> FEATURE:
<223> OTHER INFORMATION: Primer

<400> SEQUENCE: 22
tcatgcttag tccactgtct gt 22

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
actaccacca cctccagtca 20

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
acaaggtgac gactctctgc 20

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
gcagacagga aaactgagga 20

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
aaatgtggtg ggaacagaga 20

<210> SEQ ID NO 27
<211> LENGTH: 20
<212> TYPE: DNA
<213> ORGANISM: Artificial
<220> FEATURE:
<223> OTHER INFORMATION: Primer

<400> SEQUENCE: 27
gctactgggg tagcaactga 20

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
gaaggcagtg aggaactgaa 20

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
gacccaaaca ttcggaacac 20

<210> SEQ ID NO 30
<211> LENGTH: 22
<212> TYPE: DNA
<213> ORGANISM: Artificial
<220> FEATURE:
<223> OTHER INFORMATION: Primer

<400> SEQUENCE: 30
gcagcttcta ggagttcgtc tt 22

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
aacgagtcaa gaggctggtg 20

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
ttcaactacg tctttccgcc 20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
ctctgctcct cctgttcgac 20

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
ttaaaagcag ccctggtgac 20

<210> SEQ ID NO 35

<211> LENGTH: 32
<212> TYPE: PRT
<213> ORGANISM: Homo sapiens

<400> SEQUENCE: 35

Gln Asp His His Gln Gln Leu Val Ala His Ala Ala Arg Gln Glu Pro
1 5 10 15

Gln Gly Gln Glu Ile Gln Ser Glu Asn Leu Ile Met Glu Lys Gln Leu
20 25 30

<210> SEQ ID NO 36
<211> LENGTH: 29
<212> TYPE: PRT
<213> ORGANISM: Mus musculus

<400> SEQUENCE: 36

Gln Asp His His Gln Gln Leu Val Ala His Ala Arg Gln Glu Pro Gln
1 5 10 15

Gly Gln Glu Ile Gln Ser Glu Asn Met Glu Lys Gln Leu
20 25

<210> SEQ ID NO 37
<211> LENGTH: 30
<212> TYPE: PRT
<213> ORGANISM: Canis familiaris

<400> SEQUENCE: 37

Gln Asp His His Gln Gln Leu Val Ala His Ala Ala Arg Gln Glu Pro
1 5 10 15

Gln Gly Gln Glu Ile Gln Glu Asn Ile Met Glu Lys Gln Leu
20 25 30

<210> SEQ ID NO 38
<211> LENGTH: 23
<212> TYPE: PRT
<213> ORGANISM: Xenopus

<400> SEQUENCE: 38

Gln Asp Leu Val His Ala Ala Arg Gln Glu Pro Gln Gly Gln Glu Ile
1 5 10 15

Gln Glu Asn Met Glu Lys Gln
20

<210> SEQ ID NO 39
<211> LENGTH: 18
<212> TYPE: PRT
<213> ORGANISM: Danio rerio

<400> SEQUENCE: 39

Asp Glu His Val His Ala Arg Gln Glu Pro Gln Gly Gln Glu Leu Gln
1 5 10 15

Glu Lys

<210> SEQ ID NO 40
<211> LENGTH: 32
<212> TYPE: PRT
<213> ORGANISM: Homo sapiens

<400> SEQUENCE: 40

Thr Gln Glu Asp Pro Gln Met Val Tyr Gln Ser Ala Arg Gln Glu Pro
1 5 10 15

Gln Gly Gln Glu His Gln Val Asp Asn Thr Val Met Glu Lys Gln Val

```
            20                  25                  30


<210> SEQ ID NO 41
<211> LENGTH: 32
<212> TYPE: PRT
<213> ORGANISM: Mus musculus

<400> SEQUENCE: 41

Thr Gln Glu Asp Pro Gln Met Val Tyr Gln Ser Ala Arg Gln Glu Pro
1               5                   10                  15

Gln Gly Gln Glu His Gln Gly Asp Asn Thr Val Met Glu Lys Gln Val
            20                  25                  30


<210> SEQ ID NO 42
<211> LENGTH: 32
<212> TYPE: PRT
<213> ORGANISM: Canis familiaris

<400> SEQUENCE: 42

Ala Gln Glu Asp Pro Pro Met Val Tyr Gln Ser Ala Arg Gln Glu Pro
1               5                   10                  15

Gln Gly Gln Glu His Gln Val Asp Asn Thr Val Met Glu Lys Gln Gly
            20                  25                  30


<210> SEQ ID NO 43
<211> LENGTH: 26
<212> TYPE: PRT
<213> ORGANISM: Xenopus

<400> SEQUENCE: 43

Gln Glu Asp Pro Gln Met Val Gln Ser Ala Arg Gln Glu Pro Gln Gly
1               5                   10                  15

Gln Glu His Asp Asn Thr Val Met Glu Lys
            20                  25


<210> SEQ ID NO 44
<211> LENGTH: 14
<212> TYPE: PRT
<213> ORGANISM: Danio rerio

<400> SEQUENCE: 44

Arg Gln Glu Pro Gln Gly Gln Glu His Gln Asp Met Glu Lys
1               5                   10


<210> SEQ ID NO 45
<211> LENGTH: 32
<212> TYPE: PRT
<213> ORGANISM: Homo sapiens

<400> SEQUENCE: 45

Ala Pro Glu Asp Ser Gln Val Leu Gln Gln Ala Thr Arg Gln Glu Pro
1               5                   10                  15

Gln Gly Gln Glu His Gln Gly Gly Glu Asn His Leu Ala Glu Asn Thr
            20                  25                  30


<210> SEQ ID NO 46
<211> LENGTH: 31
<212> TYPE: PRT
<213> ORGANISM: Mus musculus

<400> SEQUENCE: 46

Ala Pro Glu Asp Ser Gln Val Leu Gln Gln Ala Thr Arg Gln Glu Pro
1               5                   10                  15
```

-continued

```
Gln Gly Gln Glu His Gln Gly Gly Glu Thr His Leu Ala Glu Asn
            20                  25                  30


<210> SEQ ID NO 47
<211> LENGTH: 32
<212> TYPE: PRT
<213> ORGANISM: Canis familiaris

<400> SEQUENCE: 47

Ala Pro Glu Asp Thr Gln Val Leu Gln Gln Ala Thr Arg Gln Glu Pro
1               5                   10                  15

Gln Gly Gln Glu His Gln Gly Gly Glu Ser His Leu Ala Glu Asn Thr
            20                  25                  30


<210> SEQ ID NO 48
<211> LENGTH: 15
<212> TYPE: PRT
<213> ORGANISM: Xenopus

<400> SEQUENCE: 48

Glu Ser Gln Arg Gln Glu Pro Gln Gly Gln Glu His Gln Gly His
1               5                   10                  15


<210> SEQ ID NO 49
<211> LENGTH: 9
<212> TYPE: PRT
<213> ORGANISM: Danio rerio

<400> SEQUENCE: 49

Arg Gln Glu Pro Gln Gly Gln Glu Leu
1               5
```

TREATMENT OF HIPPO PATHWAY MUTANT TUMORS AND METHODS OF IDENTIFYING SUBJECTS AS CANDIDATES FOR TREATMENT

This application is a national stage application under ±U.S.C. 0 371 of PCT Application No. PCT/US2017/029646, filed Apr. 26, 2017, which claims the priority benefit of U.S. Provisional Patent Application Ser. No. 62/327,903, filed Apr. 26, 2016, each of which is hereby incorporated by reference in its entirety.

This invention was made with Government support under CA170702 awarded by the National Institutes of Health. The Government has certain rights in the invention.

FIELD OF THE INVENTION

The present invention relates to treatment of Hippo pathway mutant tumors and methods of identifying subjects as candidates for treatment.

BACKGROUND OF THE INVENTION

The Hippo pathway is an evolutionarily conserved signaling pathway that plays a fundamental role in growth control, stem cell function, tissue regeneration, and tumor suppression (Johnson and Halder, "The Two Faces of Hippo: Targeting the Hippo Pathway for Regenerative Medicine and Cancer Treatment," *Nat. Rev. Drug Disc.* 13(1):63-79 (2014); Pan, "The Hippo Signaling Pathway in Development and Cancer," *Dev. Cell* 19(4):491-505 (2010)). It features a core kinase module characterized by MST1/2 and LATS1/2 that phosphorylate and inhibit the transcriptional co-activators, YAP/TAZ, by preventing their nuclear localization (Johnson and Halder, "The Two Faces of Hippo: Targeting the Hippo Pathway for Regenerative Medicine and Cancer Treatment," *Nat. Rev. Drug Disc.* 13(1):63-79 (2014)). YAP/TAZ lack an intrinsic DNA-binding domain and thus they can contact the DNA only through transcription factor partners such as TEAD1/-2/-3/-4, Runx1/-2, p73, Pax3, AP-1, or TBXS (Varelas, "The Hippo Pathway Effectors TAZ and YAP in Development, Homeostasis and Disease," *Development* 141(8):1614-1626 (2014)).

Among these, TEAD family members appear to play a dominant role as primary mediators of YAP/TAZ-dependent gene regulation with target genes, including a number involved in cell proliferation and cell motility (Stein et al., "YAP1 Exerts Its Transcriptional Control via TEAD-Mediated Activation of Enhancers," *PLoS Genet.* 11(8):e1005465 (2015); Zanconato et al., "Genome-Wide Association Between YAP/TAZ/TEAD and AP-1 at Enhancers Drives Oncogenic Growth," *Nat. Cell Biol.* 17(9):1218-1227 (2015); Zhao et al., "TEAD Mediates YAP-Dependent Gene Induction and Growth Control," *Genes & Dev.* 22(14):1962-1971 (2008)).

YAP overexpression in model systems in vivo was initially shown to confer transforming, invasive, and prosurvival properties (Dong et al., "Elucidation of a Universal Size-Control Mechanism in *Drosophila* and Mammals," *Cell* 130(6):1120-1133 (2007)), which could be abrogated by YAP downregulation (Camargo et al., "YAP1 Increases Organ Size and Expands Undifferentiated Progenitor Cells," *Curr. Biol.* 17(23):2054-2060 (2007)), and Hippo pathway alterations have increasingly been implicated in human tumorigenesis.

In addition to YAP amplification or over expression observed in various epithelial malignancies (Yu et al., "Hippo Pathway in Organ Size Control, Tissue Homeostasis, and Cancer," *Cell* 163(4):811-828 (2015)) as well as YAP or TAZ translocations (Yu et al., "Hippo Pathway in Organ Size Control, Tissue Homeostasis, and Cancer," *Cell* 163(4):811-828 (2015)) or point mutation (Chen et al., "R331W Missense Mutation of Oncogene YAP1 Is a Germline Risk Allele for Lung Adenocarcinoma With Medical Actionability," *J. Clin. Oncol.* 33(20):2303-2310 (2015)), loss of function mutations of core components of the Hippo inhibitory pathway such as LATS or NF2 are found at high frequencies in mesotheliomas (Murakami et al., "LATS2 is a Tumor Suppressor Gene of Malignant Mesothelioma," *Cancer Res.* 71(3):873-883 (2011); Sekido, "Inactivation of Merlin in Malignant Mesothelioma Cells and the Hippo Signaling Cascade Dysregulation," *Pathol. Int.* 61(6):331-344 (2011)). Moreover, NF2 is commonly mutated in familial meningiomas and schwannomas as well as in spontaneous tumors of these and other tumor types (Xiao et al., "NF2: The Wizardry of Merlin," *Genes Chrom. Cancer* 38(4):389-399 (2003)).

Recent studies have identified G-Protein-Coupled Receptors ("GPCRs"), which signal to either activate or inhibit Hippo signaling (Yu et al., "Regulation of the Hippo-YAP Pathway by G-Protein-Coupled Receptor Signaling," *Cell* 150(4):780-791 (2012)), and mutations in of some G proteins have now been shown to activate YAP-dependent TEAD transcriptional activity in a high fraction of uveal melanomas and at lower frequency in other melanomas (Feng et al., "Hippo-Independent Activation of YAP by the GNAQ Uveal Melanoma Oncogene Through a Trio-Regulated Rho GTPase Signaling Circuitry," *Cancer Cell* 25(6):831-845 (2014); Yu et al., "Mutant Gq/11 Promote Uveal Melanoma Tumorigenesis by Activating YAP," *Cancer Cell* 25(6):822-830 (2014)).

Deep sequencing studies have revealed that almost 20% of human tumors harbor mutations in GPCRs (O'Hayre et al., "The Emerging Mutational Landscape of G Proteins and G-Protein-Coupled Receptors in Cancer," *Nat. Rev. Cancer* 13(6):412-424 (2013)), suggesting that mutations in other GPCRs and G proteins may also deregulate the Hippo pathway. Epigenetic silencing of Hippo components has been reported in human cancer as well (Takahashi et al., "Down-Regulation of LATS1 and LATS2 mRNA Expression by Promoter Hypermethylation and its Association with Biologically Aggressive Phenotype in Human Breast Cancers," *Clin. Cancer Res.* 11(4):1380-1385 (2005); Seidel et al., "Frequent Hypermethylation of MST1 and MST2 in Soft Tissue Sarcoma," *Mol. Carcinog.* 46(10):865-871 (2007); Jiang et al., "Promoter Hypermethylation-Mediated Down-Regulation of LATS1 and LATS2 in Human Astrocytoma," *Neurosci. Res.* 56(4):450-458 (2006)).

The emerging role of Hippo pathway deregulation in cancer has increasingly focused attention on this signaling pathway as an anticancer target (Johnson and Halder, "The Two Faces of Hippo: Targeting the Hippo Pathway for Regenerative Medicine and Cancer Treatment," *Nat. Rev. Drug Disc.* 13(1):63-79 (2014)). However, efforts focused on chemical inhibition of deregulated Hippo signaling tumors are still in their infancy.

The present invention is directed to overcoming deficiencies in the art.

SUMMARY OF THE INVENTION

One aspect of the present invention relates to a method of treating a tumor in a subject. This method involves administering to a subject having a Hippo pathway mutant tumor a tankyrase inhibitor, where the tumor is susceptible to treatment with the tankyrase inhibitor, and said administering is carried out to treat the tumor.

Another aspect of the present invention relates to a method of treating cancer in a subject. This method involves administering to a subject having a cancer comprising a Hippo pathway mutant tumor susceptible to treatment with a tankyrase inhibitor a tankyrase inhibitor, where the tankyrase inhibitor treats the subject for cancer.

A further aspect of the present invention relates to a method of identifying a subject as a candidate for treatment. This method involves obtaining a tissue sample from a tumor in a subject and determining whether the tumor is a Hippo pathway mutant tumor susceptible to treatment with a tankyrase inhibitor. A determination that the tumor is a Hippo pathway mutant tumor susceptible to treatment with a tankyrase inhibitor identifies the subject as a candidate for treatment.

In the present invention, and as specifically illustrated in the Examples provided infra, constitutive high TEAD transcriptional activity was genetically validated in human tumor cells with loss of function mutations in well-established Hippo pathway core components, LATS and NF2, as therapeutic targets and identified a mechanism by which small molecule tankyrase inhibitors specifically antagonize such Hippo pathway deregulated tumor cells. The results shown herein demonstrate an actual reduction to practice that tankyrase inhibitors antagonize proliferation of human tumor cells with Hippo pathway mutations, and further that this inhibition of growth is specifically by angiomotin stabilization (see FIGS. 12A-J). Wang et al., "Tankyrase Inhibitors Target YAP by Stabilizing Angiomotin Family Proteins," *Cell Reports* 13:524-532 (2015) ("Wang") discuss the therapeutic potential of tankyrase inhibitors in cancer, and highlight at least three different oncogenic proteins/pathways (YAP, WNT, and AKT). However, Wang et al. utilize artificially manipulated nontumorigenic epithelial cells, and nowhere show that tankyrase inhibitor induced growth inhibition is specifically mediated by angiomotin stabilization. Further, the present invention establishes that the level and durability of angiomotin stabilization in response to tankyrase inhibition is important in determining tumor sensitivity to this treatment.

BRIEF DESCRIPTION OF THE DRAWINGS

FIGS. 1A-D show that Hippo pathway mutant tumors are reliant on TEAD transcriptional activity for proliferation. FIG. 1A is a graph showing TEAD reporter activity in Hippo pathway wild type (black) and mutant (gray) cells. Cells were seeded at either low ($2\times10^4$ cells) or high ($1.5\times10^5$ cells) density in 24 well plates, in the absence or presence of 10% serum, and reporter activity was measured after 15 hours incubation. FIGS. 1B-C are graphs showing TEAD reporter activity (FIG. 1B) and mRNA expression levels relative to those in the 293T empty vector (FIG. 1C) in Hippo pathway wild type and mutant cells stably expressing dnTEAD4. FIG. 1D shows representative images of colony formation by the cell lines as indicated in FIG. 1B. Error bars indicate standard deviation (SD) of experiments performed in triplicate. ***P≤0.001. Student t-Test.

FIGS. 2A-J show that dnTEAD4 inhibits TEAD transcriptional activity. FIG. 2A shows the results of a Western blot analysis showing the expression of Hippo pathway core components in the indicated cell lines. The discontinuity in the bands is due to deletion of irrelevant lanes in the gel. FIG. 2B is a graph showing relative YAP mRNA expression levels in the indicated cell lines. YAP expression of each line is shown relative to 293T cells. FIG. 2C shows Western blot analysis of 293T cells stably expressing dnTEAD4. FIG. 2D is a graph showing relative CTGF and CYR61 mRNA expression levels in 293T treated as in FIG. 2C. FIG. 2E shows Western blot analysis of MCF10A cells stably expressing dnTEAD4. FIG. 2F is a graph showing relative CTGF and CYR61 mRNA expression levels in MCF10A treated as in FIG. 2E. FIGS. 2G-J show the results of Western blot analysis of the indicated cell lines stably expressing dnTEAD4. Error bars indicate SD of experiments performed in triplicate. ***P≤0.001. Student t-Test.

FIGS. 3A-C show that a small molecule screen identifies XAV939 as a novel inhibitor of TEAD transcriptional activity. FIG. 3A is a plot showing TEAD reporter activity of 293 cells treated for 24 hours with inhibitors at a concentration of 10 μM. FIG. 3B is a graph showing TEAD reporter activity of Hippo pathway wild-type and mutant cells treated with XAV939 or 0.1% DMSO as control ("CTR") for 24 hours. FIG. 3C shows representative images of colony formation by the indicated cell lines treated with XAV939 or CTR. Error bars indicate SD of experiments performed in triplicate. ***P≤0.001. Student t-Test.

FIGS. 4A-F show that XAV939 inhibits TEAD target genes. Specifically, FIGS. 4A-F are graphs showing relative mRNA expression levels of CTGF, CYR61, and ANKRD1 in the indicated cell lines treated with XAV939 or CTR for 24 hours. Error bars indicate SD of experiments performed in triplicate. *P≤0.05, P≤0.01, *P≤0.001. Student t-Test.

FIGS. 5A-B show that dnTEAD4 and XAV939 induce G1 arrest in Hippo pathway mutant tumor cells but not Hippo pathway wild-type cells. Specifically, FIGS. 5A-B show cell cycle profiles by Propidium Iodide staining of the indicated cell lines stably expressing dnTEAD4 (FIG. 5A) and treated with 10 μM of XAV939 or CTR for 72 hours (FIG. 5B). Statistical analysis of the cell cycle profile is shown below. Error bars indicate SD of experiments performed in triplicate.

FIGS. 6A-H show that XAV939 downregulates TEAD transcriptional activity transcription through tankyrase inhibition. FIGS. 6A-B are graphs showing TEAD reporter activity of 293T (FIG. 6A) or H2373 (FIG. 6B) cells treated for 24 hours with the indicated inhibitors or CTR. FIGS. 6C-D show representative images of colony formation by 293T (FIG. 6C) or H2373 (FIG. 6D) cells treated with the indicated inhibitors or CTR. FIGS. 6E-F show TEAD reporter activity in 293T (FIG. 6E) or H2373 (FIG. 6F) cells in the absence or presence of tankyrase ("TNKS") silencing. Western blot analysis showing knockdown efficiency of TNKS1/2 is also shown. FIGS. 6G-H show representative images of colony formation by 293T (FIG. 6G) or H2373 (FIG. 6H) cells with TNKS silencing. Error bars indicate SD of representative experiments performed in triplicate. *P≤0.05, P≤0.01, *P≤0.001. Student t-Test.

FIGS. 7A-H show that tankyrase inhibition downregulates expression of TEAD target genes. Relative mRNA expression levels of CTGF, CYR61, and ANKRD1 in 293T (FIGS. 7A-C) and H2373 (FIGS. 7D-F) cells treated with 10 μM of the indicated inhibitors or CTR for 24 hours is shown. FIGS. 7G-H are graphs showing relative mRNA expression levels of CTGF, CYR61, and ANKRD1 in 293T (FIG. 7G) and H2373 (FIG. 7H) cells stably silenced for TNKS1/2. Error bars indicate SD of experiments performed in triplicate. *P≤0.05, **P≤0.01.

FIGS. 8A-F show TCF (TOP/FOP) reporter activity in the indicated cell lines (FIG. 8A); anchorage-independent growth of MCF10A cells stably expressing empty vector (EV), YAP-WT, YAP-S127A, or YAP-S94A (FIG. 8B); Western blot analysis of MCF10A cells stably expressing HRAS-V12 for the proteins indicated (FIG. 8C); TEAD reporter activity of EV and HRAS-V12 MCF10A cells (FIG. 8D); Western blot analysis of 211H and MESO25 cells treated with 10 μM of XAV939 or CTR for 24 hours (FIG. 8E); and relative AMOTL2 mRNA expression level in 211H and MESO25 cells treated with 10 μM XAV939 or CTR for 24 hours (FIG. 8F). Error bars indicate SD of experiments performed in triplicate.

FIGS. 9A-E show that XAV939 inhibits YAP-dependent transformation by a S127 phosphorylation-independent mechanism. FIGS. 9A-C show the results of Western blot analysis (FIG. 9A), TEAD reporter activity (FIG. 9B), and relative mRNA expression of TEAD target genes (FIG. 9C) in MCF10A cells stably expressing YAP-WT, YAP-S127A, or YAP-S94A. FIG. 9D shows images of anchorage-independent growth of MCF10A cells stably expressing YAP-WT, YAP-S127A, or HRAS-V12 and treated with XAV939, verteporfin (VP), or CTR. FIG. 9E shows images of anchorage-independent growth of MCF10A cells stably expressing YAP-WT, YAP-S127A, or HRAS-V12 in the presence or absence of dnTEAD4 overexpression. Error bars indicate SD of experiments performed in triplicate. ***P≤0.001. Student t-Test.

FIGS. 10A-F show that XAV939 induces YAP cytoplasmic relocalization. FIGS. 5A-B show immunofluorescence images of endogenous YAP expression (FIG. 10A) and Western blot analysis of indicated proteins (FIG. 10B) in H2373 cells treated with XAV939 or CTR for 24 hours. FIGS. 10C-E show Western blot analysis (FIG. 10C), TEAD reporter activity (FIG. 10D), and relative mRNA expression levels of TEAD target genes (FIG. 10E) in MCF10A cells stably overexpressing YAP-S127A. FIG. 10F shows images from immunofluorescence analysis of MCF10A stably expressing YAP-S127A treated with XAV939 or CTR for 24 hours. Bar: 10 μm. Error bars represent SD of experiments performed in triplicate. ***P≤0.001. Student t-Test.

FIGS. 11A-I show that tankyrase inhibition stabilizes angiomotin proteins and increases AMOT-YAP protein complex formation. FIG. 11A is a graph showing mRNA expression levels of AMOT, AMOTL1, and AMOTL2 in the indicated cell lines. Values are represented relative to AMOT levels in MCF10A. FIG. 11B shows Western blot analysis images showing AMOT, AMOTL1, and AMOTL2 expression in the indicated cell lines. FIGS. 11C-D are graphs showing mRNA expression levels of AMOT, AMOTL1, and AMOTL2 in 293T (FIG. 11C) and H2373 (FIG. 11D) cells treated with 10 μM of the indicated inhibitors or CTR for 24 hours. FIG. 11E shows Western blot analysis of 293T and H2373 cells treated as in FIGS. 11C-D. FIG. 11F shows Western blot analysis of 293T cells treated with 10 μM of XAV939 or CTR for 24 hours. At 24 hours, cycloheximide (20 μg/ml) was added for additional times as indicated. AMOT and Tubulin protein levels were quantified with an Odyssey Infrared Imaging System, and relative expression levels are as shown. FIG. 11G shows co-immunoprecipitation results of endogenous AMOT and TNKS in 293T CTR cells or treated with 10 μM of XAV939 for 24 hours. FIG. 11H shows co-immunoprecipitation results of endogenous AMOT and YAP in 293T CTR cells or treated with 10 μM of XAV939 for 24 hours. FIG. 11I shows co-immunoprecipitation results of endogenous YAP and AMOT in 293T CTR cells or treated with 10 μM of XAV939 for 24 hours. In all co-immunoprecipitation experiments, 10% of total cell lysate was used as Input. Error bars indicate SD of experiments performed in triplicate.

FIGS. 12A-J show that angiomotin stabilization determines the ability of XAV939 to inhibit TEAD-mediated transcription and proliferation of Hippo pathway mutant tumor cells. FIG. 12A shows the results of Western blot analysis of H2052 cell lysates following treatment with 10 μM of XAV939 or CTR for 24 hours. FIG. 12B is a graph showing TEAD reporter activity in H2052 and H2373 cells treated with 10 μM of XAV939 or CTR for the indicated time points. Fresh medium with XAV939 was replaced every 2 days. FIGS. 12C-D show relative CTGF mRNA expression level (FIG. 12C) and Western blot analysis of TNKS, AMOTL2, and PTEN (FIG. 12D) in H2052 and H2373 cells treated as in FIG. 12B. AMOTL2 and Tubulin protein levels in FIG. 12D were measured with the Odyssey Infrared Imaging System and relative expression was normalized to H2052 t=0 as shown. FIGS. 12E-F show relative AMOTL2 mRNA expression and protein level in H2373 cells stably expressing doxycycline-inducible shRNA, treated with 1 μg/ml of doxycycline (DOX) for 72 hours and with 10 μM of XAV939 or CTR in the 24 hours prior to lysing the cells. FIGS. 12G-I are graphs showing TEAD reporter activity (FIG. 12G) and relative mRNA expression levels of TEAD target genes (FIGS. 12H-I) in H2373 cells treated as in FIG. 12E. FIG. 12J shows representative images of colony formation by H2373 cells treated initially as in FIG. 12E and then cultured under the same conditions for a total of 14 days by replacing the media containing XAV939 or DOX, as indicated, every 48 hours. Error bars indicate SD of experiments performed in triplicate. *P≤0.05, P≤0.01, *P≤0.001. Student t-Test.

FIGS. 13A-D show that the durability and level of Angiomotin stabilization is crucial for XAV939 effectiveness in inhibiting TEAD dependent transcription and growth of Hippo deregulated tumor cells. FIG. 13A shows the results of Western blot analysis of Angiomotin (AMOTL2) in MCF10A, 211H, and H2052 cell lysates following treatment with either 10 μM of XAV939 or overexpression of Angiomotin (AMOTL2) or empty vector (EV). FIG. 13B is a graph showing TEAD reporter activity in MCF10A, 211H, and H2052 cells treated with either 10 μM of XAV939 or overexpression of Angiomotin (AMOTL2) or empty vector (EV). FIG. 13C shows representative images of colony formation by MCF10A, 211H, and H2052 cells treated as in FIGS. 13A-B. FIG. 13D is a graph showing % colony formation based on the images shown in FIG. 13C.

FIGS. 14A-D show that AMOTL2 mRNA levels are not affected by XAV939 treatment. FIG. 14A is a graph showing relative AMOTL2 mRNA expression level in H2052 cells treated 10 μM of XAV939 or CTR for 24 hours. FIGS. 14B-C are graphs showing relative AMOTL2, TNKS1, and TNKS2 mRNA expression levels in H2052 and H2373 cells treated with 10 μM of XAV939 or CTR for the indicated time points. Values are shown relative to H2052 expression level at time 0. FIG. 14D is a graph showing relative ANKRD1 mRNA expression levels in H2373 cells stably expressing doxycycline-inducible shRNA treated with 1 μg/ml of doxycycline (DOX) for 72 hours and with 10 μM of XAV939 or CTR in the 24 hours prior to lysing the cells for RNA extraction. Error bars indicate SD of experiments performed in triplicate.

DETAILED DESCRIPTION OF THE INVENTION

The present invention relates to treatment of Hippo pathway mutant tumors and methods of identifying subjects as candidates for treatment.

One aspect of the present invention relates to a method of treating a tumor in a subject. This method involves administering to a subject having a Hippo pathway mutant tumor a tankyrase inhibitor, where the tumor is susceptible to treatment with the tankyrase inhibitor, and said administering is carried out to treat the tumor.

As used herein, Hippo pathway mutant tumors are tumors comprising at least one mutation in one or more Hippo pathway genes selected from LATS1, LATS2, NF2, and YAP. These Hippo pathway genes are well known.

Human LATS1, also known as Large Tumor Suppressor Kinase 1, comprises the published nucleotide sequence set forth in Accession No. NM_004690 (SEQ ID NO:1), as follows:

```
gcgacgctca cgaacgatca gagctgcggg cgacgcaacg aagcccggag gccgcaggct    60
gcgcgctccc tcgcagcagc cgggcgggca aaagccccca gtcctcggcc cccgcgcaag   120
cgacgccggg aaatgcccac atccgggaaa cctgcagcgg agtgcggcgg cggcgacact   180
gagtggaagg caaaatggcg gcggcggcgg cggtggcctg gtgttaaggg gagagccagg   240
tcctcacgac ccctgggacg ggccgcgctg gcccgcggca gcccccccgt tcgtctcccc   300
gctctgcccc accagggata cttggggttg ctgggacgga ctctggccgc ctcagcgtcc   360
gccctcaggc ccgtggccgc tgtccaggag ctctgctctc ccctccagag ttaattattt   420
atattgtaaa gaattttaac agtcctgggg acttccttga aggatcattt tcacttttgc   480
tcagaagaaa gctctggatc tatcaaataa agaagtcctt cgtgtgggct acatatatag   540
atgttttcat gaagaggagt gaaaagccag aaggatatag acaaatgagg cctaagacct   600
ttcctgccag taactatact gtcagtagcc ggcaaatgtt acaagaaatt cgggaatccc   660
ttaggaattt atctaaacca tctgatgctg ctaaggctga gcataacatg agtaaaatgt   720
caaccgaaga tcctcgacaa gtcagaaatc cacccaaatt tgggacgcat cataaagcct   780
tgcaggaaat tcgaaactct ctgcttccat ttgcaaatga aacaaattct tctcggagta   840
cttcagaagt taatccacaa atgcttcaag acttgcaagc tgctggattt gatgaggata   900
tggttataca agctcttcag aaaactaaca acagaagtat agaagcagca attgaattca   960
ttagtaaaat gagttaccaa gatcctcgac gagagcagat ggctgcagca gctgccagac  1020
ctattaatgc cagcatgaaa ccagggaatg tgcagcaatc agttaaccgc aaacagagct  1080
ggaaaggttc taaagaatcc ttagttcctc agaggcatgg cccgccacta ggagaaagtg  1140
tggcctatca ttctgagagt cccaactcac agacagatgt aggaagacct ttgtctggat  1200
ctggtatatc agcatttgtt caagctcacc ctagcaacgg acagagagtg aacccccccac  1260
caccacctca agtaaggagt gttactcctc caccacctcc aagaggccag actccccctc  1320
caagaggtac aactccacct ccccccttcat gggaaccaaa ctctcaaaca aagcgctatt  1380
ctggaaacat ggaatacgta atctcccgaa tctctcctgt cccacctggg gcatggcaag  1440
agggctatcc tccaccacct ctcaacactt cccccatgaa tcctcctaat caaggacaga  1500
gaggcattag ttctgttcct gttggcagac aaccaatcat catgcagagt tctagcaaat  1560
ttaactttcc atcagggaga cctggaatgc agaatggtac tggacaaact gatttcatga  1620
tacaccaaaa tgttgtccct gctggcactg tgaatcggca gccaccacct ccatatcctc  1680
tgacagcagc taatggacaa agcccttctg ctttacaaac agggggatct gctgctcctt  1740
cgtcatatac aaatggaagt attcctcagt ctatgatggt gccaaacaga aatagtcata  1800
acatggaact atataacatt agtgtacctg gactgcaaac aaattggcct cagtcatctt  1860
ctgctccagc ccagtcatcc ccgagcagtg ggcatgaaat ccctacatgg caacctaaca  1920
taccagtgag gtcaaattct tttaataacc cattaggaaa tagagcaagt cactctgcta  1980
attctcagcc ttctgctaca acagtcactg caattacacc agctcctatt caacagcctg  2040
tgaaaagtat gcgtgtatta aaaccagagc tacagactgc tttagcacct acacaccctt  2100
cttggatacc acagccaatt caaactgttc aacccagtcc ttttcctgag ggaaccgctt  2160
caaatgtgac tgtgatgcca cctgttgctg aagctccaaa ctatcaagga ccaccaccac  2220
cctacccaaa acatctgctg caccaaaacc catctgttcc tccatacgag tcaatcagta  2280
```

-continued

```
agcctagcaa agaggatcag ccaagcttgc ccaaggaaga tgagagtgaa aagagttatg  2340

aaaatgttga tagtggggat aaagaaaaga aacagattac aacttcacct attactgtta  2400

ggaaaaacaa gaaagatgaa gagcgaaggg aatctcgtat tcaaagttat tctcctcaag  2460

catttaaatt ctttatggag caacatgtag aaaatgtact caaatctcat cagcagcgtc  2520

tacatcgtaa aaaacaatta gagaatgaaa tgatgcgggt tggattatct caagatgccc  2580

aggatcaaat gagaaagatg ctttgccaaa aagaatctaa ttacatccgt cttaaaaggg  2640

ctaaaatgga caagtctatg tttgtgaaga taaagacact aggaatagga gcatttggtg  2700

aagtctgtct agcaagaaaa gtagatacta aggctttgta tgcaacaaaa actcttcgaa  2760

agaaagatgt tcttcttcga aatcaagtcg ctcatgttaa ggctgagaga gatatcctgg  2820

ctgaagctga caatgaatgg gtagttcgtc tatattattc attccaagat aaggacaatt  2880

tatactttgt aatggactac attcctgggg gtgatatgat gagcctatta attagaatgg  2940

gcatctttcc agaaagtctg gcacgattct acatagcaga acttacctgt gcagttgaaa  3000

gtgttcataa aatgggtttt attcatagag atattaaacc tgataatatt ttgattgatc  3060

gtgatggtca tattaaattg actgactttg gcctctgcac tggcttcaga tggacacacg  3120

attctaagta ctatcagagt ggtgaccatc cacggcaaga tagcatggat ttcagtaatg  3180

aatgggggga tccctcaagc tgtcgatgtg gagacagact gaagccatta gagcggagag  3240

ctgcacgcca gcaccagcga tgtctagcac attctttggt tgggactccc aattatattg  3300

cacctgaagt gttgctacga acaggataca cacagttgtg tgattggtgg agtgttggtg  3360

ttattctttt tgaaatgttg gtgggacaac ctcctttctt ggcacaaaca ccattagaaa  3420

cacaaatgaa ggttatcaac tggcaaacat ctcttcacat tccaccacaa gctaaactca  3480

gtcctgaagc ttctgatctt attattaaac tttgccgagg acccgaagat cgcttaggca  3540

agaatggtgc tgatgaaata aaagctcatc catttttttaa aacaattgac ttctccagtg  3600

acctgagaca gcagtctgct tcatacattc ctaaaatcac acacccaaca gatacatcaa  3660

attttgatcc tgttgatcct gataaattat ggagtgatga taacgaggaa gaaaatgtaa  3720

atgacactct caatggatgg tataaaaatg gaaagcatcc tgaacatgca ttctatgaat  3780

ttaccttccg aaggtttttt gatgacaatg gctacccata taattatccg aagcctattg  3840

aatatgaata cattaattca caaggctcag agcagcagtc ggatgaagat gatcaaaaca  3900

caggctcaga gattaaaaat cgcgatctag tatatgttta acacactagt aaataaatgt  3960

aatgaggatt tgtaaaaggg cctgaaatgc gaggtgtttt gaggttctga gagtaaaatt  4020

atgcaaatat gacagagcta tatatgtgtg ctctgtgtac aatattttat tttcctaaat  4080

tatgggaaat ccttttaaaa tgttaattta ttccagccgt ttaaatcagt atttagaaaa  4140

aaattgttat aaggaaagta aattatgaac tgaatattat agtcagttct tggtacttaa  4200

agtacttaaa ataagtagtg ctttgtttaa aaggagaaac ctggtatcta tttgtatata  4260

tgctaaataa ttttaaaata caagagtttt tgaaattttt ttgaaagaca gttttagttt  4320

tatcttgctt taaccaaata tgaaacatac cccctatttt acagagctct tttttcccct  4380

cataaccttg tttttggtag aaaataagct agagaaatta agccatcgtg ttggtgagtg  4440

ttcctaggct aatgataatc tgtataattc acatcctgaa actaaggaat acagggttga  4500

aaaaatatta atatgtttgt cagaaggaaa aataatgcat ttatcttccc ccccaccccc  4560

cgccccatgg aatatttaat ctatttaatc ttcttgcatt tatttctcaa gaattactgg  4620

ctttaaaaga agccaaagca ctactagctt tttttccata ttggtatttt tgatgctgct  4680
```

-continued

```
tccaatttta aaagggaaca aagctgccat aaatcgaaat gttcaatact aaaagctaaa  4740
atatttctca ccatcctaag cagataatta ttttaatttt catatacttt tcctgtatag  4800
taactatttt gattatatca tcaatgttac ctgtttcctc tttcagaaca gtgctgcata  4860
tacagattgt tattggcaaa ggaaaatctg gctatctggc aatattttac ctaagcgcag  4920
attaattggt gaaaaaatta actcttaaga tggccattaa taattaggaa agtttacaga  4980
gtggtcttag tagaaaattc aagtcctcct aatttattta aggttcaata atgcgttcaa  5040
catgcctgtt atgtataacg cttaggttct aaggaagatt aaggtttcat accaaaatac  5100
atgtagctta tcttttagga aggggaaaaa ggctccattt tgaccatagt aaaatttgtg  5160
ttgtgtttta tttccttttc ttaagctcca ctgataaggg attgttttta tcaaaagtta  5220
ctatttgtag attggaggca taattttagt gattttcata cttttagctt tcttcgcata  5280
aaagctaatt gaaaccgtat atgtagtaaa attaaaggca gagctgttgc agttgaattg  5340
gagagttagg gcaaagaaca cttattagcc cacacttccc acctttctac aggtggtcct  5400
ttcagagctc agcctgaaaa cccactactg tgttatcgtg cgtcttttgg ggttagtggt  5460
tcttttgaga atctgaagga agctgtggac tcttcctaga aaaaaaaacc acacatacac  5520
atacaatgtt gcatgcagtt tcaagggatt ttggacatat tgaaacctat cacaggctgt  5580
aggttatgga cctctgtgcc atgagaaaat tgatacatta aactaagaac tttgttttta  5640
acttaccaat cactactcag cacatcttat ataagctgat aatttgtgat ggaaaaggtc  5700
tgtagcatgt gatataaggt gaccttatga atgcctctct tgctggtaca ttaagttgtt  5760
ttaatatatc atttggaggg gactgaaatg ttaggctcat tacaagcttg atacagaaat  5820
atttctgaag gatttctaat cagaattgta aaacaatgtg ctatcatgaa atcgcagtct  5880
tcacctcatg gttcatggaa catttggtta gtcccataaa atcctatgca aaacaaagta  5940
gttcaagaat ttttaggtgg gtagtcacat ttataaggta ttcctcttac tctttgggct  6000
ttttcagtct gatttattta aattttcatt tagttgtttt acttttggac taaggtgcaa  6060
tacagtagaa gataactttg ttacatttat gttgtaggaa aactaaggtg ctgtctcctc  6120
ccccttccct tcccacaaaa tctgtattcc ccctattgct gaaatgtaac agacactaca  6180
aattttgtat tctttttttg tttttgtttt tgagacaggg tctcactctg tcacccaggc  6240
tggagggcag tggcgcttca cagctcactg catcctcaac cttgggggct cacgcagtcc  6300
tcccgcctca gcctcccaag tagctgggca tgcgccacca agcccagcta atttttgtat  6360
ctttagtaga gatggggttt cgccatgttg cccaggttgg tgtggaattc ctgggctcca  6420
gttatatgcc cacctcagcc tcccaaagtg ctgggattac agacgtgacc caccgcgcct  6480
ggcgcaaata tgtattcttt taaaatttcc tctgatacta taagcttttt gcatttatct  6540
gaagcagtat acatgccttt ggtatcagca attttaacag tttggatata cttatcagct  6600
atcttattcc aaaactacat ctacttcttc cagtatagaa tctggtgctt cctgaccaaa  6660
aagatgagaa aacaatgtt  aaaaatatag atgctttcca ttgaaatgga gtgaaaacat  6720
tggttctata tgttttcttt taaaataatt ttcttattaa aaacttgctg tctttattat  6780
acttaccctt tttatgcata tcaatagtat ttataagatg tgttctataa ttatgtaatt  6840
gtagatactg ttatgcattg tccagtgaca tcataaggca ggccctactg ctgtatcttt  6900
tctaccttct tatttgtaat agaaactata gaatgtatga ctaaaaagtc actttgagat  6960
tgactttttt aaaaagttat taccttctgc tgttgcaaag tgcaaaactg tgagtggaat  7020
tgttttattc tgacttaatg tgttagaaat tagagaatac agtgggagga tttttagaca  7080
ttgctgctgc tgttacccaa ggtattttag ataaaaaatt tttaataaac atccctttgg  7140
```

-continued

```
tatttaaagt ggaacattta gcctgttcat tttaatctaa agcaaaaagt aatttgggtc  7200
aaaatattgg tatatttgta aagcgcctta atatatccct ttgtggaagg cactacacag  7260
tttactttta tattgtattg tgtatataag tattttgtat taaaattgaa tcagtggcaa  7320
cattaaagtt ttataaaatc atgctttgtt agaaaaagaa ttacagcttt gcaatataac  7380
taattgtttc gcataattct gaatgtaata gatatgaata atcagcctgt gtttttaatg  7440
aacttatttg tattttccca atcattttct ctagtgtaat gtttgctggg ataataaaaa  7500
aaattcaaat ctttcaaaaa aaaaaaaaaa aaa                               7533
```

The human LATS1 protein encoded by this nucleotide sequence is as follows (SEQ ID NO:2):

```
MKRSEKPEGY RQMRPKTFPA SNYTVSSRQM LQEIRESLRN
LSKPSDAAKA EHNMSKMSTE DPRQVRNPPK FGTHHKALQE
IRNSLLPFAN ETNSSRSTSE VNPQMLQDLQ AAGFDEDMVI
QALQKTNNRS IEAAIEFISK MSYQDPRREQ MAAAAARPIN
ASMKPGNVQQ SVNRKQSWKG SKESLVPQRH GPPLGESVAY
HSESPNSQTD VGRPLSGSGI SAFVQAHPSN GQRVNPPPPP
QVRSVTPPPP PRGQTPPPRG TTPPPPSWEP NSQTKRYSGN
MEYVISRISP VPPGAWQEGY PPPPLNTSPM NPPNQGQRGI
SSVPVGRQPI IMQSSSKFNF PSGRPGMQNG TGQTDFMIHQ
NVVPAGTVNR QPPPPYPLTA ANGQSPSALQ TGGSAAPSSY
TNGSIPQSMM VPNRNSHNME LYNISVPGLQ TNWPQSSSAP
AQSSPSSGHE IPTWQPNIPV RSNSFNNPLG NRASHSANSQ
PSATTVTAIT PAPIQQPVKS MRVLKPELQT ALAPTHPSWI
PQPIQTVQPS PFPEGTASNV TVMPPVAEAP NYQGPPPPYP
KHLLHQNPSV PPYESISKPS KEDQPSLPKE DESEKSYENV
```

-continued

```
DSGDKEKKQI TTSPITVRKN KKDEERRESR IQSYSPQAFK
FFMEQHVENV LKSHQQRLHR KKQLENEMMR VGLSQDAQDQ
MRKMLCQKES NYIRLKRAKM DKSMFVKIKT LGIGAFGEVC
LARKVDTKAL YATKTLRKKD VLLRNQVAHV KAERDILAEA
DNEWVVRLYY SFQDKDNLYF VMDYIPGGDM MSLLIRMGIF
PESLARFYIA ELTCAVESVH KMGFIHRDIK PDNILIDRDG
HIKLTDFGLC TGFRWTHDSK YYQSGDHPRQ DSMDFSNEWG
DPSSCRCGDR LKPLERRAAR QHQRCLAHSL VGTPNYIAPE
VLLRTGYTQL CDWWSVGVIL FEMLVGQPPF LAQTPLETQM
KVINWQTSLH IPPQAKLSPE ASDLIIKLCR GPEDRLGKNG
ADEIKAHPFF KTIDFSSDLR QQSASYIPKI THPTDTSNFD
PVDPDKLWSD DNEEENVNDT LNGWYKNGKH PEHAFYEFTF
RRFFDDNGYP YNYPKPIEYE YINSQGSEQQ SDEDDQNTGS
EIKNRDLVYV
```

Human LATS2, also known as Large Tumor Suppressor Kinase 2, comprises the published nucleotide sequence set forth in Accession No. NM_014572 (SEQ ID NO:3), as follows:

```
gcccgtggaa tgccaacaat gtagcgaatg tcccacttgg gtctgcgctt tggaaccgcg    60
gcgtgagcgc cccgggaaga tggagcagtc gccgtccacg ccaccgccgc cgcccggggc   120
tccccccgtcc ctgcggggcc agcagcagct ccagccacca gtgcccggtc tcccggcgcg   180
agaggcccgg gagccgccgg ccaggacgcc cccgagggtg tagaccgcgc ccctggagag   240
agtgataatc ttcaaaatga agactttgga aaattttagg ttctctatag gaactacaaa   300
aatggaagga aagaacattt tcaaaaggaa attattttga aagtatgttt acaacaaact   360
gatactattg acagtttttt tttttaaata ataaaacact ttaagaagat tgtatttatg   420
gtaaaaggaa actggactaa caatgaggcc aaagactttt cctgccacga cttattctgg   480
aaatagccgg cagcgactgc aagagattcg tgaggggtta aaacagccat ccaagtcttc   540
ggttcagggg ctacccgcag gaccaaacag tgacacttcc ctggatgcca aagtcctggg   600
gagcaaagat gccaccaggc agcagcagca gatgagagcc accccaaagt tcggacctta   660
tcagaaagcc ttgagggaaa tcagatattc cttgttgcct tttgctaatg aatcgggcac   720
ctctgcagct gcagaagtga accggcaaat gctgcaggaa ctggtgaacg caggatgcga   780
ccaggagatg gctggccgag ctctcaagca gactggcagc aggagcatcg aggccgccct   840
```

-continued

```
ggagtacatc agcaagatgg gctacctgga cccgaggaat gagcagattg tgcgggtcat    900
taagcagacc tccccaggaa aggggctcat gccaacccca gtgacgcgga ggcccagctt    960
cgaaggaacc ggcgattcgt ttgcgtccta ccaccagctg agcggtaccc cctacgaggg   1020
cccaagcttc ggcgctgacg gccccacggc gctggaggag atgccgcggc cgtacgtgga   1080
ctaccttttc cccggagtcg gcccccacgg gcccggccac cagcaccagc acccacccaa   1140
gggctacggt gccagcgtag aggcagcagg ggcacacttc ccgctgcagg gcgcgcacta   1200
cgggcggccg cacctgctgg tgcctgggga acccctgggc tacggagtgc agcgcagccc   1260
ctccttccag agcaagacgc cgccggagac cgggggttac gccagcctgc ccacgaaggg   1320
ccagggagga ccgccaggcg ccggcctcgc tttcccaccc cctgccgccg ggctctacgt   1380
gccgcaccca caccacaagc aggccggtcc cgcggcccac cagctgcatg tgctgggctc   1440
ccgcagccag gtgttcgcca gcgacagccc cccgcagagc ctgctcactc cctcgcggaa   1500
cagcctcaac gtggacctgt atgaattggg cagcacctcc gtccagcagt ggccggctgc   1560
caccctggcc cgccgggact ccctgcagaa gccgggcctg gaggcgccgc cgcgcgcgca   1620
cgtggccttc cggcctgact gcccagtgcc cagcaggacc aactccttca acagccacca   1680
gccgcggccc ggtccgcctg gcaaggccga gccctccctg cccgccccca acaccgtgac   1740
ggctgtcacg gccgcgcaca tcttgcaccc ggtgaagagc gtgcgtgtgc tgaggccgga   1800
gccgcagacg gctgtggggc cctcgcaccc cgcctgggtg cccgcgcctg ccccggcccc   1860
cgcccccgcc cccgccccgg ctgcggaggg cttggacgcc aaggaggagc atgccctggc   1920
gctgggcggc gcaggcgcct tcccgctgga cgtggagtac ggaggcccag accggaggtg   1980
cccgcctccg ccctacccga agcacctgct gctgcgcagc aagtcggagc agtacgacct   2040
ggacagcctg tgcgcaggca tggagcagag cctccgtgcg ggccccaacg agcccgaggg   2100
cggcgacaag agccgcaaaa gcgccaaggg ggacaaaggc ggaaaggata aaaagcagat   2160
tcagacctct cccgttcccg tccgcaaaaa cagcagagac gaagagaaga gagagtcacg   2220
catcaagagc tactcgccat acgcctttaa gttcttcatg gagcagcacg tggagaatgt   2280
catcaaaacc taccagcaga aggttaaccg gaggctgcag ctggagcaag aaatggccaa   2340
agctggactc tgtgaagctg agcaggagca gatgcggaag atcctctacc agaaagagtc   2400
taattacaac aggttaaaga gggccaagat ggacaagtct atgtttgtca agatcaaaac   2460
cctggggatc ggtgcctttg gagaagtgtg ccttgcttgt aaggtggaca ctcacgccct   2520
gtacgccatg aagaccctaa ggaaaaagga tgtcctgaac cggaatcagg tggcccacgt   2580
caaggccgag agggacatcc tggccgaggc agacaatgag tgggtggtca aactctacta   2640
ctccttccaa gacaaagaca gcctgtactt tgtgatggac tacatccctg gtggggacat   2700
gatgagcctg ctgatccgga tggaggtctt ccctgagcac ctggcccggt tctacatcgc   2760
agagctgact ttggccattg agagtgtcca caagatgggc ttcatccacc gagacatcaa   2820
gcctgataac attttgatag atctggatgg tcacattaaa ctcacagatt tcggcctctg   2880
cactgggttc aggtggactc acaattccaa atattaccag aaagggagcc atgtcagaca   2940
ggacagcatg gagcccagcg acctctggga tgatgtgtct aactgtcggt gtggggacag   3000
gctgaagacc ctagagcaga gggcgcggaa gcagcaccag aggtgcctgg cacattcact   3060
ggtggggact ccaaactaca tcgcacccga ggtgctcctc cgcaaagggt acactcaact   3120
ctgtgactgg tggagtgttg gagtgattct cttcgagatg ctggtggggc agccgccctt   3180
tttggcacct actcccacag aaacccagct gaaggtgatc aactgggaga acacgctcca   3240
cattccagcc caggtgaagc tgagccctga ggccagggac ctcatcacca agctgtgctg   3300
```

-continued

```
ctccgcagac caccgcctgg ggcggaatgg ggccgatgac ctgaaggccc accccttctt  3360
cagcgccatt gacttctcca gtgacatccg gaagcagcca gccccctacg ttcccaccat  3420
cagccacccc atggacacct cgaatttcga ccccgtagat gaagaaagcc cttggaacga  3480
tgccagcgaa ggtagcacca aggcctggga cacactcacc tcgcccaata acaagcatcc  3540
tgagcacgca ttttacgaat tcaccttccg aaggttcttt gatgacaatg gctacccctt  3600
tcgatgccca aagccttcag gagcagaagc ttcacaggct gagagctcag atttagaaag  3660
ctctgatctg gtggatcaga ctgaaggctg ccagcctgtg tacgtgtaga tgggggccag  3720
gcacccccac cactcgctgc ctcccaggtc agggtcccgg agccggtgcc ctcacaggcc  3780
aatagggaag ccgagggctg ttttgtttta aattagtccg tcgattactt cacttgaaat  3840
tctgctcttc accaagaaaa cccaaacagg acacttttga aaacaggact cagcatcgct  3900
ttcaataggc ttttcaggac cttcactgca ttaaaacaat atttttgaaa atttagtaca  3960
gtttagaaag agcacttatt ttgtttatat ccatttttc ttactaaatt atagggatta  4020
actttgacaa atcatgctgc tgttattttc tacatttgta ttttatccat agcacttatt  4080
cacatttagg aaaagacata aaaactgaag aacattgatg agaaatctct gtgcaataat  4140
gtaaaaaaaa aaaaagataa cactctgctc aatgtcacgg agaccatttt atccacacaa  4200
tggtttttgt tttttatttt ttcccatgtt tcaaaattgt gatataatga tataatgtta  4260
aaagctgctt tttttggctt tttgcatatc tagtataata ggaagtgtga gcaaggtgat  4320
gatgtggctg tgatttccga cgtctggtgt gtggagagta ctgcatgagc agagttcttc  4380
tattataaaa ttaccatatc ttgccattca cagcaggtcc tgtgaatacg tttttactga  4440
gtgtctttaa atgaggtgtt ctagacagtg tgctgataat gtattgtgcg ggtgacctct  4500
tcgctatgat tgtatctctt actgttttgt taaagaaatg cagatgtgta actgagaagt  4560
gatttgtgtg tgtgtcttgg ttgtgattgg attctttggg ggggggggaac tgaaacattt  4620
gtcatatact gaacttatat acatcaaaag ggattaatac agcgatgcca aaaagtttaa  4680
tcacggacac atgtccgttt ctgtagtccg tatgctcttt cattcttggt agagctggta  4740
tgtggaatgc catacctctg accctactac ttaccttttt actgacagac tgcccacact  4800
gaaagcttca gtgaatgttc ttagtcctgt tttcttctgt tactgtcagg aaactgagtg  4860
atctaatggt tctctcactt ttttttgtt cttttagtgt actttgaagt atcaaatctt  4920
aacttggttt aaacaataca tattcctaac ctttgtaaaa aagcaaagat tcttcaaaat  4980
gacattgaaa taaaaagtaa gccatacgta ttttcttaga agtatagatg tatgtgcgtg  5040
tatacacaca cacacacaca cacagagata aacacaatat tccttatttc aaattagtat  5100
gattcctatt taaagtgatt tatatttgag taaaaagttc aattcttttt tgctttttaa  5160
aaaatctgat gcttcataat tttcattata ttattccaca tatttttcct tgaagttctt  5220
agcataatgt atccattact tagtatatat ctaggcaaca acacttagaa gtttatcagt  5280
gtttaaacta aaaaaataaa gattcctgtg tactggttta catttgtgtg agtggcatac  5340
tcaagtctgc tgtgcctgtc gtcgtgactg tcagtattct cgctatttta tagtcgtgcc  5400
atgttgttac tcacagcgct ctgacatact ttcatgtggt aggttctttc tcaggaactc  5460
agtttaacta ttatttattg atatatcatt acctttgaaa agcttctact ggcacaattt  5520
attattaaaa ttttgaatcc aaaaaaaaaa aaaaaaaa                           5558
```

The human LATS2 protein encoded by this nucleotide sequence is as follows (SEQ ID NO:4):

```
MRPKTFPATT YSGNSRQRLQ EIREGLKQPS KSSVQGLPAG
PNSDTSLDAK VLGSKDATRQ QQQMRATPKF GPYQKALREI
RYSLLPFANE SGTSAAAEVN RQMLQELVNA GCDQEMAGRA
LKQTGSRSIE AALEYISKMG YLDPRNEQIV RVIKQTSPGK
GLMPTPVTRR PSFEGTGDSF ASYHQLSGTP YEGPSFGADG
PTALEEMPRP YVDYLFPGVG PHGPGHQHQH PPKGYGASVE
AAGAHFPLQG AHYGRPHLLV PGEPLGYGVQ RSPSFQSKTP
PETGGYASLP TKGQGGPPGA GLAFPPPAAG LYVPHPHHKQ
AGPAAHQLHV LGSRSQVFAS DSPPQSLLTP SRNSLNVDLY
ELGSTSVQQW PAATLARRDS LQKPGLEAPP RAHVAFRPDC
PVPSRTNSFN SHQPRPGPPG KAEPSLPAPN TVTAVTAAHI
LHPVKSVRVL RPEPQTAVGP SHPAWVPAPA PAPAPAPAPA
AEGLDAKEEH ALALGGAGAF PLDVEYGGPD RRCPPPPYPK
HLLLRSKSEQ YDLDSLCAGM EQSLRAGPNE PEGGDKSRKS
```

-continued

```
AKGDKGGKDK KQIQTSPVPV RKNSRDEEKR ESRIKSYSPY
AFKFFMEQHV ENVIKTYQQK VNRRLQLEQE MAKAGLCEAE
QEQMRKILYQ KESNYNRLKR AKMDKSMFVK IKTLGIGAFG
EVCLACKVDT HALYAMKTLR KKDVLNRNQV AHVKAERDIL
AEADNEWVVK LYYSFQDKDS LYFVMDYIPG GDMMSLLIRM
EVFPEHLARF YIAELTLAIE SVHKMGFIHR DIKPDNILID
LDGHIKLTDF GLCTGFRWTH NSKYYQKGSH VRQDSMEPSD
LWDDVSNCRC GDRLKTLEQR ARKQHQRCLA HSLVGTPNYI
APEVLLRKGY TQLCDWWSVG VILFEMLVGQ PPFLAPTPTE
TQLKVINWEN TLHIPAQVKL SPEARDLITK LCCSADHRLG
RNGADDLKAH PFFSAIDFSS DIRKQPAPYV PTISHPMDTS
NFDPVDEESP WNDASEGSTK AWDTLTSPNN KHPEHAFYEF
TFRRFFDDNG YPFRCPKPSG AEASQAESSD LESSDLVDQT
EGCQPVYV
```

Human NF2 comprises the published nucleotide sequence set forth in Accession No. CR456530 (SEQ ID NO:5), as follows:

```
gggctaaagg gctcagagtg caggccgtgg ggcgcgaggg tcccgggcct gagccccgcg    60
ccatggccgg ggccatcgct tcccgcatga gcttcagctc tctcaagagg aagcaaccca   120
agacgttcac cgtgaggatc gtcaccatgg acgccgagat ggagttcaat tgcgagatga   180
agtggaaagg gaaggacctc tttgatttgg tgtgccggac tctggggctc cgagaaacct   240
ggttctttgg actgcagtac acaatcaagg acacagtggc ctggctcaaa atggacaaga   300
aggtactgga tcatgatgtt tcaaaggaag aaccagtcac ctttcacttc ttggccaaat   360
tttatcctga gaatgctgaa gaggagctgg ttcaggagat cacacaacat ttattcttct   420
tacaggtaaa gaagcagatt ttagatgaaa agatctactg ccctcctgag gcttctgtgc   480
tcctggcttc ttacgccgtc caggccaagt atggtgacta cgaccccagt gttcacaagc   540
ggggattttt ggcccaagag gaattgcttc caaaaagggt aataaatctg tatcagatga   600
ctccggaaat gtgggaggag agaattactg cttggtacgc agagcaccga ggccgagcca   660
gggatgaagc tgaaatggaa tatctgaaga tagctcagga cctggagatg tacggtgtga   720
actactttgc aatccggaat aaaaagggca cagagctgct gcttggagtg gatgccctgg   780
ggcttcacat ttatgaccct gagaacagac tgacccccaa gatctccttc ccgtggaatg   840
aaatccgaaa catctcgtac agtgacaagg agtttactat taaaccactg gataagaaaa   900
ttgatgtctt caagtttaac tcctcaaagc ttcgtgttaa taagctgatt ctccagctat   960
gtatcgggaa ccatgatcta tttatgagga gaaggaaagc cgattctttg gaagttcagc  1020
agatgaaagc ccaggccagg gaggagaagg ctagaaagca gatggagcgg cagcgcctcg  1080
ctcgagagaa gcagatgagg gaggaggctg aacgcacgag ggatgagttg gagaggaggc  1140
tgctgcagat gaaagaagaa gcaacaatgg ccaacgaagc actgatgcgg tctgaggaga  1200
cagctgacct gttggctgaa aaggcccaga tcaccgagga ggaggcaaaa cttctggccc  1260
agaaggccgc agaggctgag caggaaatgc agcgcatcaa ggccacagcg attcgcacgg  1320
aggaggagaa gcgcctgatg gagcagaagg tgctggaagc cgaggtgctg gcactgaaga  1380
```

-continued

```
tggctgagga gtcagagagg agggccaaag aggcagatca gctgaagcag gacctgcagg  1440
aagcacgcga ggcggagcga agagccaagc agaagctcct ggagattgcc accaagccca  1500
cgtacccgcc catgaaccca attccagcac cgttgcctcc tgacatacca agcttcaacc  1560
tcattggtga cagcctgtct ttcgacttca aagatactga catgaagcgg ctttccatgg  1620
agatagagaa agaaaaagtg gaatacatgg aaaagagcaa gcatctgcag gagcagctca  1680
atgaactcaa gacagaaatc gaggccttga aactgaaaga gagggagaca gctctggata  1740
ttctgcacaa tgagaactcc gacaggggtg gcagcagcaa gcacaatacc attaaaaagc  1800
tcaccttgca gagcgccaag tcccgagtgg ccttctttga agagctctag caggtgaccc  1860
agccacccca ggacctgcca cttctcctgc tac                                1893
```

The human NF2 protein encoded by this nucleotide sequence is as follows (SEQ ID NO:6):

```
MAGAIASRMS FSSLKRKQPK TFTVRIVTMD AEMEFNCEMK
WKGKDLFDLV CRTLGLRETW FFGLQYTIKD TVAWLKMDKK
VLDHDVSKEE PVTFHFLAKF YPENAEEELV QEITQHLFFL
QVKKQILDEK IYCPPEASVL LASYAVQAKY GDYDPSVHKR
GFLAQEELLP KRVINLYQMT PEMWEERITA WYAEHRGRAR
DEAEMEYLKI AQDLEMYGVN YFAIRNKKGT ELLLGVDALG
LHIYDPENRL TPKISFPWNE IRNISYSDKE FTIKPLDKKI
DVFKFNSSKL RVNKLILQLC IGNHDLFMRR RKADSLEVQQ
```

-continued

```
MKAQAREEKA RKQMERQRLA REKQMREEAE RTRDELERRL
LQMKEEATMA NEALMRSEET ADLLAEKAQI TEEEAKLLAQ
KAAEAEQEMQ RIKATAIRTE EEKRLMEQKV LEAEVLALKM
AEESERRAKE ADQLKQDLQE AREAERRAKQ KLLEIATKPT
YPPMNPIPAP LPPDIPSFNL IGDSLSFDFK DTDMKRLSME
IEKEKVEYME KSKHLQEQLN ELKTEIEALK LKERETALDI
LHNENSDRGG SSKHNTIKKL TLQSAKSRVA FFEEL
```

Human YAP, also known as Yes Associated Protein 1, comprises the published nucleotide sequence set forth in Accession No. NM_001130145 (SEQ ID NO:7), as follows:

```
gccgccgcca gggaaaagaa agggaggaag gaaggaacaa gaaaaggaaa taaagagaaa    60
ggggaggcgg ggaaaggcaa cgagctgtcc ggcctccgtc aagggagttg gagggaaaaa   120
gttctcaggc gccgcaggtc cgagtgcctc gcagcccctc ccgaggcgca gccgccagac   180
cagtggagcc ggggcgcagg gcgggggcgg aggcgccggg gcgggggatg cggggccgcg   240
gcgcagcccc ccggccctga gagcgaggac agcgccgccc ggcccgcagc cgtcgccgct   300
tctccacctc ggcccgtgga gccggggcgt ccgggcgtag ccctcgctcg cctgggtcag   360
ggggtgcgcg tcgggggagg cagaagccat ggatcccggg cagcagccgc cgcctcaacc   420
ggcccccag ggccaagggc agccgccttc gcagcccccg caggggcagg gcccgccgtc   480
cggacccggg caaccggcac ccgcggcgac ccaggcggcg ccgcaggcac cccccgccgg   540
gcatcagatc gtgcacgtcc gcggggactc ggagaccgac ctggaggcgc tcttcaacgc   600
cgtcatgaac cccaagacgg ccaacgtgcc ccagaccgtg cccatgaggc tccggaagct   660
gcccgactcc ttcttcaagc cgccggagcc caaatcccac tcccgacagg ccagtactga   720
tgcaggcact gcaggagccc tgactccaca gcatgttcga gctcattcct ctccagcttc   780
tctgcagttg ggagctgttt ctcctgggac actgaccccc actggagtag tctctggccc   840
agcagctaca cccacagctc agcatcttcg acagtcttct tttgagatac ctgatgatgt   900
acctctgcca gcaggttggg agatggcaaa gacatcttct ggtcagagat acttcttaaa   960
tcacatcgat cagacaacaa catggcagga ccccaggaag gccatgctgt cccagatgaa  1020
cgtcacagcc cccaccagtc caccagtgca gcagaatatg atgaactcgg cttcaggtcc  1080
tcttcctgat ggatgggaac aagccatgac tcaggatgga gaaatttact atataaacca  1140
taagaacaag accacctctt ggctagaccc aaggcttgac cctcgttttg ccatgaacca  1200
```

-continued

```
gagaatcagt cagagtgctc cagtgaaaca gccaccaccc ctggctcccc agagcccaca  1260
gggaggcgtc atgggtggca gcaactccaa ccagcagcaa cagatgcgac tgcagcaact  1320
gcagatggag aaggagaggc tgcggctgaa acagcaagaa ctgcttcggc aggcaatgcg  1380
gaatatcaat cccagcacag caaattctcc aaaatgtcag gagttagccc tgcgtagcca  1440
gttaccaaca ctggagcagg atggtgggac tcaaaatcca gtgtcttctc ccgggatgtc  1500
tcaggaattg agaacaatga cgaccaatag ctcagatcct ttccttaaca gtggcaccta  1560
tcactctcga gatgagagta cagacagtgg actaagcatg agcagctaca gtgtccctcg  1620
aaccccagat gacttcctga acagtgtgga tgagatggat acaggtgata ctatcaacca  1680
aagcaccctg ccctcacagc agaaccgttt cccagactac cttgaagcca ttcctgggac  1740
aaatgtggac cttggaacac tggaaggaga tggaatgaac atagaaggag aggagctgat  1800
gccaagtctg caggaagctt tgagttctga catccttaat gacatggagt ctgttttggc  1860
tgccaccaag ctagataaag aaagctttct tacatggtta tagagccctc aggcagactg  1920
aattctaaat ctgtgaagga tctaaggaga cacatgcacc ggaaatttcc ataagccagt  1980
tgcagttttc aggctaatac agaaaaagat gaacaaacgt ccagcaagat actttaatcc  2040
tctattttgc tcttccttgt ccattgctgc tgttaatgta ttgctgacct ctttcacagt  2100
tggctctaaa gaatcaaaag aaaaaaactt tttatttctt ttgctattaa aactactgtt  2160
cattttgggg gctgggggaa gtgagcctgt ttggatgatg gatgccattc cttttgccca  2220
gttaaatgtt caccaatcat tttaactaaa tactcagact tagaagtcag atgcttcatg  2280
tcacagcatt tagtttgttc aacagttgtt tcttcagctt cctttgtcca gtggaaaaac  2340
atgatttact ggtctgacaa gccaaaaatg ttatatctga tattaaatac ttaatgctga  2400
tttgaagaga tagctgaaac caaggctgaa gactgtttta ctttcagtat tttcttttcc  2460
tcctagtgct atcattagtc acataatgac cttgatttta ttttaggagc ttataaggca  2520
tgagacaatt tccatataaa tatattaatt attgccacat actctaatat agattttggt  2580
ggataatttt gtgggtgtgc attttgttct gttttgttgg gtttttttgtt ttttttgttt  2640
ttggcagggt cggtgggggg gttggttggt tggttggttt tgtcggaacc taggcaaatg  2700
accatattag tgaatctgtt aatagttgta gcttgggatg gttattgtag ttgttttggt  2760
aaaatcttca tttcctggtt ttttttacca ccttatttaa atctcgatta tctgctctct  2820
cttttatata catacacaca cccaaacata acatttataa tagtgtggta gtggaatgta  2880
tccttttttta ggtttccctg ctttccagtt aatttttaaa atggtagcgc tttgtatgca  2940
tttagaatac atgactagta gtttatattt cactggtagt ttaaatctgg ttggggcagt  3000
ctgcagatgt ttgaagtagt ttagtgttct agaaagagct attactgtgg atagtgccta  3060
ggggagtgct ccacgccctc tgggcatacg gtagatatta tctgatgaat tggaaaggag  3120
caaaccagaa atggctttat tttctccctt ggactaattt ttaagtctcg attggaattc  3180
agtgagtagg ttcataatgt gcatgacaga aataagcttt atagtggttt accttcattt  3240
agctttggaa gttttctttg ccttagtttt ggaagtaaat tctagtttgt agttctcatt  3300
tgtaatgaac acattaacga ctagattaaa atattgcctt caagattgtt cttacttaca  3360
agacttgctc ctacttctat gctgaaaatt gaccctggat agaatactat aaggttttga  3420
gttagctgga aaagtgatca gattaataaa tgtatattgg tagttgaatt tagcaaagaa  3480
atagagataa tcatgattat acctttattt ttacaggaag agatgatgta actagagtat  3540
gtgtctacag gagtaataat ggtttccaaa gagtattttt taaaggaaca aaacgagcat  3600
```

-continued

```
gaattaactc ttcaatataa gctatgaagt aatagttggt tgtgaattaa agtggcacca  3660
gctagcacct ctgtgtttta agggtctttc aatgtttcta gaataagccc ttattttcaa  3720
gggttcataa caggcataaa atctcttctc ctggcaaaag ctgctatgaa aagcctcagc  3780
ttgggaagat agattttttt ccccccaatt acaaaatcta agtattttgg cccttcaatt  3840
tggaggaggg caaaagttgg aagtaagaag ttttatttta agtactttca gtgctcaaaa  3900
aaatgcaatc actgtgttgt atataatagt tcataggttg atcactcata ataattgact  3960
ctaaggcttt tattaagaaa acagcagaaa gattaaatct tgaattaagt ctgggggGaa  4020
atggccactg cagatggagt tttagagtag taatgaaatt ctacctagaa tgcaaaattg  4080
ggtatatgaa ttacatagca tgttgttggg atttttttta atgtgcagaa gatcaaagct  4140
acttggaagg agtgcctata atttgccagt agccacagat taagattata tcttatatat  4200
cagcagatta gctttagctt agggggaggg tgggaaagtt tggggggggg gttgtgaaga  4260
tttaggggga ccttgataga gaactttata aacttctttc tctttaataa agacttgtct  4320
tacaccgtgc tgccattaaa ggcagctgtt ctagagtttc agtcacctaa gtacacccac  4380
aaaacaatat gaatatggag atcttccttt acccctcaac tttaatttgc ccagttatac  4440
ctcagtgttg tagcagtact gtgatacctg gcacagtgct ttgatcttac gatgccctct  4500
gtactgacct gaaggagacc taagagtcct ttcccttttt gagtttgaat catagccttg  4560
atgtggtctc ttgttttatg tccttgttcc taatgtaaaa gtgcttaact gcttcttggt  4620
tgtattgggt agcattggga taagatttta actgggtatt cttgaattgc ttttacaata  4680
aaccaatttt ataatcttta aatttatcaa ctttttacat ttgtgttatt ttcagtcagg  4740
gcttcttaga tctacttatg gttgatggag cacattgatt tggagtttca gatcttccaa  4800
agcactattt gttgtaataa cttttctaaa tgtagtgcct ttaaaggaaa aatgaacaca  4860
gggaagtgac tttgctacaa ataatgttgc tgtgttaagt attcatatta aatacatgcc  4920
ttctatatgg aacatggcag aaagactgaa aaataacagt aattaattgt gtaattcaga  4980
attcatacca atcagtgttg aaactcaaac attgcaaaag tgggtggcaa tattcagtgc  5040
ttaacacttt tctagcgttg gtacatctga gaaatgagtg ctcaggtgga ttttatcctc  5100
gcaagcatgt tgttataaga attgtgggtg tgcctatcat aacaattgtt ttctgtatct  5160
tgaaaaagta ttctccacat tttaaatgtt ttatattaga gaattcttta atgcacactt  5220
gtcaaatata tatatatagt accaatgtta cctttttatt ttttgtttta gatgtaagag  5280
catgctcata tgttaggtac ttacataaat tgttacatta ttttttctta tgtaatacct  5340
ttttgtttgt ttatgtggtt caaatatatt ctttccttaa actcttaaaa aaaaaa      5396
```

The YAP protein encoded by this nucleotide sequence is as follows (SEQ ID NO:8):

```
MDPGQQPPPQ PAPQGQGQPP SQPPQGQGPP SGPGQPAPAA
TQAAPQAPPA GHQIVHVRGD SETDLEALFN AVMNPKTANV
PQTVPMRLRK LPDSFFKPPE PKSHSRQAST DAGTAGALTP
QHVRAHSSPA SLQLGAVSPG TLTPTGVVSG PAATPTAQHL
RQSSFEIPDD VPLPAGWEMA KTSSGQRYFL NHIDQTTTWQ
DPRKAMLSQM NVTAPTSPPV QQNMMNSASG PLPDGWEQAM
TQDGEIYYIN HKNKTTSWLD PRLDPRFAMN QRISQSAPVK
QPPPLAPQSP QGGVMGGSNS NQQQQMRLQQ LQMEKERLRL
```

-continued

```
KQQELLRQAM RNINPSTANS PKCQELALRS QLPTLEQDGG
TQNPVSSPGM SQELRTMTTN SSDPFLNSGT YHSRDESTDS
GLSMSSYSVP RTPDDFLNSV DEMDTGDTIN QSTLPSQQNR
FPDYLEAIPG TNVDLGTLEG DGMNIEGEEL MPSLQEALSS
DILNDMESVL AATKLDKESF LTWL
```

Mutations in Hippo pathway genes that give rise to tumors and cancers are known and continue to be discovered. Examples of those currently known in human tumors and cancers include, without limitation, NF2 deletion or inactivating mutation in mesothelioma, schwannoma, and meningioma; LATS2 deletion in mesothelioma; LATS1/2 deletion or inactivating mutations in mesotheloioma;

LATS1-PSEN1 gene fusion in mesothelioma; YAP amplification in hepatocellular carcinoma, medulloblastoma, and esophageal squamous cell carcinoma; and GNAQ/GNA11 mutation in uveal melanoma.

As used herein, a "Hippo pathway gene mutation" is a mutation in a Hippo pathway gene (e.g., LATS1, LATS2, NF2, or YAP) that may include, for example and without limitation, an insertion, a truncation, a deletion, a nonsense mutation, a frameshift mutation, a splice-site mutation, or a missense mutation.

Identifying a Hippo pathway gene mutation in a tumor can be carried out using methods that are well known in the art. In one embodiment, detecting or identifying a Hippo pathway gene mutation comprises sequencing at least a portion of the nucleotide sequence of LATS1, LATS2, NF2, or YAP comprising the mutation. This can be performed by direct sequencing of the gene, such as gene regions comprising the mutation, from a tissue sample obtained from the tumor of a subject. Direct sequencing assays typically involve isolating a DNA sample from the subject using any suitable method known in the art, and cloning the region of interest to be sequenced into a suitable vector for amplification by growth in a host cell (e.g., bacteria) or direct amplification by PCR or other amplification assay. Following amplification, the DNA can be sequenced using any suitable method. One sequencing method involves high-throughput next generation sequencing ("NGS") to identify genetic variation. Various NGS sequencing chemistries are available and suitable for use in carrying out the claimed invention, including pyrosequencing (Roche® 454), sequencing by reversible dye terminators (Illumina® HiSeq, Genome Analyzer and MiSeq systems), sequencing by sequential ligation of oligonucleotide probes (Life Technologies® SOLiD), and hydrogen ion semiconductor sequencing (Life Technologies®, Ion Torrent™). Alternatively, classic sequencing methods, such as the Sanger chain termination method or Maxam-Gilbert sequencing, which are well known to those of ordinary skill in the art, can be used to carry out the methods of the present invention (i.e., to identify or detect a Hippo pathway gene mutation).

In another embodiment, the Hippo pathway gene mutation is identified or detected in a hybridization assay utilizing one or more oligonucleotide probes comprising a nucleotide sequence that is complementary to a nucleic acid molecule comprising one or more of the Hippo pathway genes. In a hybridization assay, the presence or absence of a gene mutation is determined based on the hybridization of one or more oligonucleotide probes to one or more nucleic acid molecules in a sample from the subject. The oligonucleotide probe or probes comprise a nucleotide sequence that is complementary to at least the region of the gene that contains the identified mutation. The oligonucleotide probes are designed to be complementary to the wild type, non-mutant nucleotide sequence and/or the mutant nucleotide sequence of the one or more genes to effectuate the detection of the presence or the absence of the mutation in the sample from the subject upon contacting the sample with the oligonucleotide probe(s).

A variety of hybridization assays that are known in the art are suitable for use in the methods of the present invention. These methods include, without limitation, direct hybridization assays, such as northern blot or Southern blot (see e.g., Ausabel et al., *Current Protocols in Molecular Biology*, John Wiley & Sons, NY (1991), which is hereby incorporated by reference in its entirety). Alternatively, direct hybridization can be carried out using an array based method where oligonucleotide probe(s) designed to be complementary to a particular non-mutant or mutant gene region are affixed to a solid support. A labeled DNA or cDNA sample from the subject is contacted with the array containing the oligonucleotide probe(s), and hybridization of nucleic acid molecules from the sample to their complementary oligonucleotide probes on the array surface is detected. Examples of direct hybridization array platforms include, without limitation, the Affymetrix GeneChip or SNP arrays and Illumina's Bead Array.

In another embodiment, identifying is carried out with an amplification-based assay which amplifies a nucleic acid molecule comprising a Hippo pathway gene or a portion thereof. Amplification based assays include assays such as molecular beacon assays, nucleic acid arrays, and allele-specific PCR. Other common genotyping methods include, but are not limited to, restriction fragment length polymorphism assays; primer extension assays, such as allele-specific primer extension (e.g., Illumina® Infinium® assay), arrayed primer extension (see Krjutskov et al., "Development of a Single Tube 640-plex Genotyping Method for Detection of Nucleic Acid Variations on Microarrays," *Nucleic Acids Res.* 36(12):e75 (2008), which is hereby incorporated by reference in its entirety), homogeneous primer extension assays, primer extension with detection by mass spectrometry (e.g., Sequenom® iPLEX SNP genotyping assay) (see Zheng et al., "Cumulative Association of Five Genetic Variants with Prostate Cancer," *N. Eng. J. Med.* 358(9):910-919 (2008), which is hereby incorporated by reference in its entirety), multiplex primer extension sorted on genetic arrays; flap endonuclease assays (e.g., the Invader® assay) (see Olivier "The Invader Assay for SNP Genotyping," *Mutat. Res.* 573(1-2):103-10 (2005), which is hereby incorporated by reference in its entirety); 5' nuclease assays, such as the TaqMan® assay (see U.S. Pat. No. 5,210,015 to Gelfand et al. and U.S. Pat. No. 5,538,848 to Livak et al., which are hereby incorporated by reference in their entirety); and oligonucleotide ligation assays, such as ligation with rolling circle amplification, homogeneous ligation, OLA (see U.S. Pat. No. 4,988,617 to Landgren et al., which is hereby incorporated by reference in its entirety), multiplex ligation reactions followed by PCR, wherein zipcodes are incorporated into ligation reaction probes, and amplified PCR products are determined by electrophoretic or universal zipcode array readout (see U.S. Pat. Nos. 7,429,453 and 7,312,039 to Barany et al., which are hereby incorporated by reference in their entirety). Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

As described infra in the Examples, TEAD transcriptional activity can be measured in tumor lines to determine the effects of mutations in Hippo pathway core components on the proliferation of human tumor cells. For example, and without limitation, loss of function mutations in NF2 (H2373, MESO25), LATS1 (MSTO-211H (211H)), and NF2/LATS2 (H2052) or in immortalized non-tumorigenic (293T, MCF10A) cell lines, which are wild-type for NF2, LATS1, and LATS2 genes can provide means for determining mutations in Hippo pathway genes that give rise to tumors and cancers. Using a TEAD luciferase reporter assay, tumor lines harboring Hippo pathway mutations will show much higher reporter levels, which are insensitive to serum deprivation or high cell density as compared to Hippo pathway wild-type lines. Quantification by RT-QPCR techniques of mRNA levels of well-established TEAD target genes such as CTGF, CYR61, and ANKRD1 can be used as markers to identify Hippo pathway deregulation in tumor cells or tissues. Moreover, antibody can be used to recognize Hippo pathway proteins (e.g., YAP and TAZ) or products of TEAD target genes. For example, YAP protein levels may be markedly higher in a Hippo mutant as compared to wild-type cells despite their similar mRNA levels.

According to this method of the present invention, a subject to be treated has a Hippo pathway mutant tumor that is susceptible to treatment with a tankyrase inhibitor. As used herein, a Hippo pathway mutant tumor that is susceptible to treatment with a tankyrase inhibitor is a tumor where, upon treatment with a tankyrase inhibitor, the level and durability of angiomotin stabilization in response to tankyrase inhibition determines susceptibility or sensitivity of the tumor to treatment.

A specific non-limiting example of tumor susceptibility or sensitivity to tankyrase inhibition is illustrated in the Examples infra, and specifically in FIGS. 12B-D. In particular, H2052 cells sensitive to TEAD4 inhibition of TEAD transcriptional activity and proliferation but resistant to tankyrase inhibition by the tankyrase inhibitor XAV939, when treated with a tankyrase inhibitor experienced an initial increase in AMOTL2 protein levels at 24 hours, but then declined over the course of 12 days. In contrast, in H2373 cells, which are sensitive to tankyrase inhibition, treatment with a tankyrase inhibitor caused higher, more durable levels of AMOTL2 protein over the course of 12 days as compared to the resistant H2052 cells (see FIG. 12D). These findings are unique to the results published by Wang et al., “Tankyrase Inhibitors Target YAP by Stabilizing Angiomotin Family Proteins,” *Cell Reports* 13:524-532 (2015) (“Wang”), which discuss the therapeutic potential of tankyrase inhibitors in cancer, but nowhere show that a tankyrase inhibitor can induce growth inhibition specifically mediated by angiomotin stabilization. Further, the experimental work described in the Examples infra demonstrate that some Hippo pathway mutant tumors are susceptible to treatment with tankyrase inhibitors and some are not, and that susceptibility to treatment is determined by the extent and/or duration of stabilization of AMOT family proteins in response to treatment with a tankyrase inhibitor.

Thus, according to one embodiment, a Hippo pathway mutant tumor that is susceptible to treatment with a tankyrase inhibitor demonstrates or experiences an induction or increase in stabilization of one or more AMOT family proteins at initial treatment with a tankyrase inhibitor (e.g., higher AMOT family protein expression at the time of treatment than at pre-treatment by any amount or an amount of about 1.1, 1.2, 1.3, 1.4, 1.5, 2, 3, 4, or 5 or more times the amount of AMOT family protein expression after treatment compared to pre-treatment), and maintains an elevated level of AMOT family protein stabilization over a period of about 2, 3, 4, 5, 6, 7, 8, 9, 10, 11, or 12 or more days (i.e., shows durable stabilization of AMOT family proteins).

As used herein, AMOT family protein means any one or more of the well-known members of the AMOT family of proteins, including AMOT, AMOTL1, and AMOTL2.

According to one embodiment, the method of this aspect of the present invention further involves identifying a subject with a tumor susceptible to treatment with the tankyrase inhibitor prior to administering a tankyrase inhibitor.

In one embodiment, identifying a subject with a tumor susceptible to treatment with the tankyrase inhibitor may involve obtaining a tissue sample from a tumor in the subject and determining whether the tissue sample from the tumor exhibits Hippo pathway mutations and if so, the level and durability of angiomotin stabilization in the tissue sample from the tumor following treatment with the tankyrase inhibitor.

“Obtaining a tissue sample” as used herein, refers to obtaining possession of a sample by “directly acquiring” or “indirectly acquiring” the sample. “Directly acquiring a sample” means performing a process (e.g., performing a physical method such as a surgery, biopsy, or extraction) to obtain the sample. “Indirectly acquiring a sample” refers to receiving the sample from another party or source (e.g., a third party laboratory that directly acquired the sample). Methods described herein can include obtaining a tissue sample from a tumor.

The source of the tissue sample can be solid tissue as from a fresh, frozen, and/or preserved organ, tissue sample, biopsy, or aspirate; blood or any blood constituents; bodily fluids such as cerebral spinal fluid, amniotic fluid, peritoneal fluid, or interstitial fluid; or cells from any time in gestation or development of the subject. Preferably, the tissue sample is from a tumor. The tissue sample can contain compounds that are not naturally intermixed with the tissue in nature such as preservatives, anticoagulants, buffers, fixatives, nutrients, antibiotics or the like. The sample may be preserved as a frozen sample or as formaldehyde- or paraformaldehyde-fixed paraffin-embedded (“FFPE”) tissue preparation. For example, the sample can be embedded in a matrix, e.g., an FFPE block or a frozen sample. Typically, the sample is a tumor sample, e.g., includes one or more premalignant or malignant cells. In certain, embodiments, the sample, e.g., the tumor sample, is acquired from a solid tumor, a soft tissue tumor, or a metastatic lesion. In other embodiments, the sample, e.g., the tumor sample, includes tissue or cells from a surgical margin. In an embodiment, the sample, e.g., tumor sample, includes one or more circulating tumor cells (“CTC”) (e.g., a CTC acquired from a blood sample). In certain, embodiments, the sample, e.g., the tumor sample, is acquired from a solid tumor, a soft tissue tumor or a metastatic lesion.

Determining level and durability of angiomotin family protein stabilization can be carried out by techniques that include, for example, immunostaining for angiomotin protein family members or immunoblot analysis for these proteins. Quantification can be based on comparative analysis as taught in the Examples infra (e.g., FIGS. 12A-J).

According to one embodiment, a Hippo pathway mutant tumor susceptible to treatment with a tankyrase inhibitor would show low or undetectable levels prior to treatment and readily detectable levels in a post treatment sample. In contrast, a Hippo pathway mutant tumor not susceptible to treatment with a tankyrase inhibitor (i.e., a resistant tumor) would show low or undetectable levels both prior to and following treatment.

Thus, in carrying out this and other methods of the present invention, a subject, e.g., a human subject with a tumor, has a sample of the tumor tested to determine if the tumor is a Hippo pathway mutant tumor susceptible to treatment with a tankyrase inhibitor and, if so, the tumor in the subject is treated with a tankyrase inhibitor.

As used herein, the term “treat” or “treatment” refer to both therapeutic treatment and prophylactic or preventative measures, where the object is to prevent or slow down (lessen) an undesired physiological change or disorder, such as the development or spread of a tumor or cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and/or remission (whether partial or total), whether detectable or undetectable. "Treatment" can also mean prolonging survival as compared to expected survival if not receiving treatment. Subjects in need of treatment include those already with the condition or disorder (i.e., a tumor or cancer) as well as those prone to have the condition or disorder or those in which the condition or disorder is to be prevented. The term "treat" or "treatment" with respect to a tumor or tumor cells refers to stopping the progression of said cells, slowing down growth, inducing regression, or amelioration of symptoms associated with the presence of said cells.

In one embodiment, a tankyrase inhibitor is a small molecule. Exemplary small molecule tankyrase inhibitors include, without limitation, XAV939, MN-64, IWRI, a pyrimidinone nicotinamide mimetic (e.g., AZ-6102), and combinations thereof.

According to another embodiment, the tankyrase inhibitor is an inhibitory molecule (e.g., a nucleic acid inhibitor). Exemplary nucleic acid tankyrase inhibitors include antisense RNAs or RNAi, such as short interfering RNAs (siRNA), short hairpin RNAs (shRNA), and microRNAs.

The use of anti sense methods to inhibit the in vivo translation of genes and subsequent protein expression is well known in the art (see e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al., which are hereby incorporated by reference in their entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an mRNA molecule (see e.g., Weintraub, "Antisense DNA and RNA," *Scientific Am.* 262:40-46 (1990), which is hereby incorporated by reference in its entirety). The antisense nucleic acid molecule hybridizes to its corresponding target nucleic acid molecule, such as tankyrase mRNA, to form a double-stranded molecule, which interferes with translation of the mRNA, as the cell will not translate a double-stranded mRNA. Antisense nucleic acids used in the methods of the present invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the TANKYRASE nucleotide sequence (the nucleotide sequences of tankyrase are provided infra). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., PCT Publication Nos. WO 2004/015107 to Giese et al., WO 2003/070918 to McSwiggen et al., WO 1998/39352 to Imanishi et al and U.S. Patent Application Publication Nos. 2002/0068708 to Jesper et al., 2002/0147332 to Kaneko et al., and 2008/0119427 to Bhat et al., all of which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway.

Nucleic acid aptamers that specifically bind to TANKYRASE are also useful in the methods of the present invention. Nucleic acid aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. Nucleic acid aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

Tankyrase inhibitors suitable for use in the methods of the present invention may also include inhibitory peptides. Suitable inhibitory peptides include, without limitation, modified tankyrase inhibitor peptides that bind, preferably, specifically to the tankyrase protein but prevent normal tankyrase function. Such inhibitory peptides may be chemically synthesized using known peptide synthesis methodology or may be prepared and purified using recombinant technology. Such peptides are usually at least about 5 amino acids in length, but can be anywhere from 5 to 100 amino acids in length. Such peptides may be identified without undue experimentation using well known techniques. Techniques for screening peptide libraries for peptides that are capable of specifically binding to a polypeptide target, in this case tankyrase, are well known in the art (see e.g., U.S. Pat. No. 5,556,762 to Pinilla et al.; U.S. Pat. No. 5,750,373 to Garrard et al.; U.S. Pat. No. 4,708,871 to Geysen; U.S. Pat. No. 4,833,092 to Geysen; U.S. Pat. No. 5,223,409 to Ladner et al.; U.S. Pat. No. 5,403,484 to Ladner et al.; U.S. Pat. No. 5,571,689 to Heuckeroth et al.; U.S. Pat. No. 5,663,143 to Ley et al.; and PCT Publication Nos. WO 84/03506 and WO 84/03564 to Geysen, which are hereby incorporated by reference in their entirety).

There are two human tankyrases—tankyrase 1 and tankyrase 2. Human tankyrase 1 has a published nucleotide sequence as set forth in Accession No. NM_003747 (SEQ ID NO:9), as follows:

```
cgaagatggc ggcgtcgcgt cgctctcagc atcatcacca ccatcatcaa caacagctcc    60
agcccgcccc aggggcttca gcgccgccgc cgccacctcc tcccccactc agccctggcc   120
tggccccggg gaccacccca gcctctccca cggccagcgg cctggccccc ttcgcctccc   180
cgcggcacgg cctagcgctg ccggaggggg atggcagtcg ggatccgccc gacaggcccc   240
gatccccgga cccggttgac ggtaccagct gttgcagtac caccagcaca atctgtaccg   300
tcgccgccgc tcccgtggtc ccagcggttt ctacttcatc tgccgctggg gtcgctccca   360
acccagccgg cagtggcagt aacaattcac cgtcgtcctc ttcttccccg acttcttcct   420
catcttcctc tccatcctcc cctggatcga gcttggcgga gagccccgag gcggccggag   480
ttagcagcac agcaccactg gggcctgggg cagcaggacc tgggacaggg gtcccagcag   540
tgagcggggc cctacgggaa ctgctggagg cctgtcgcaa tggggacgtg tcccgggtaa   600
agaggctggt ggacgcggca aacgtaaatg caaaggacat ggccggccgg aagtcttctc   660
ccctgcactt cgctgcaggt tttggaagga aggatgttgt agaacactta ctacagatgg   720
gtgctaatgt ccacgctcgt gatgatggag gtctcatccc gcttcataat gcctgttctt   780
ttggccatgc tgaggttgtg agtctgttat tgtgccaagg agctgatcca aatgccaggg   840
ataactggaa ctatacacct ctgcatgaag ctgctattaa agggaagatc gatgtgtgca   900
ttgtgctgct gcagcacgga gctgacccaa acattcggaa cactgatggg aaatcagccc   960
tggacctggc agatccttca gcaaaagctg tccttacagg tgaatacaag aaagacgaac  1020
tcctagaagc tgctaggagt ggtaatgaag aaaaactaat ggctttactg actcctctaa  1080
atgtgaattg ccatgcaagt gatgggcgaa agtcgactcc tttacatcta gcagcgggct  1140
acaacagagt tcgaatagtt cagcttcttc ttcagcatgg tgctgatgtt catgcaaaag  1200
acaaaggtgg acttgtgcct cttcataatg catgttcata tggacattat gaagtcacag  1260
aactgctact aaagcatgga gcttgtgtta atgccatgga tctctggcag tttactccac  1320
tgcacgaggc tgcttccaag aaccgtgtag aagtctgctc tttgttactt agccatggcg  1380
ctgatcctac attagtcaac tgccatggca aaagtgctgt ggatatggct ccaactccgg  1440
agcttaggga gagattgact tatgaattta aaggtcattc tttactacaa gcagccagag  1500
aagcagactt agctaaagtt aaaaaaacac tcgctctgga aatcattaat ttcaaacaac  1560
cgcagtctca tgaaacagca ctgcactgtg ctgtggcctc tctgcatccc aaacgtaaac  1620
aagtgacaga attgttactt agaaaaggag caaatgttaa tgaaaaaaat aaagatttca  1680
tgactcccct gcatgttgca gccgaaagag cccataatga tgtcatggaa gttctgcata  1740
agcatggcgc caagatgaat gcactggaca cccttggtca gactgctttg catagagccg  1800
ccctagcagg ccacctgcag acctgccgcc tcctgctgag ttacggctct gacccctcca  1860
tcatctcctt acaaggcttc acagcagcac agatgggcaa tgaagcagtg cagcagattc  1920
tgagtgagag tacacctata cgtacttctg atgttgatta tcgactctta gaggcatcta  1980
aagctggaga cttggaaact gtgaagcaac tttgcagctc tcaaaatgtg aattgtagag  2040
acttagaggg ccggcattcc acgcccttac acttcgcagc aggctacaac cgcgtgtctg  2100
ttgtagagta cctgctacac cacggtgccg atgtccatgc caaagacaag ggtggcttgg  2160
tgccccttca taatgcctgt tcatatggac actatgaggt ggctgagctt ttagtaaggc  2220
atggggcttc tgtcaatgtg gcggacttat ggaaatttac ccctctccat gaagcagcag  2280
ctaaaggaaa gtatgaaatc tgcaagctcc ttttaaaaca tggagcagat ccaactaaaa  2340
agaacagaga tggaaataca cctttggatt tggtaaagga aggagacaca gatattcagg  2400
acttactgag aggggatgct gctttgttgg atgctgccaa gaagggctgc ctggcaagag  2460
```

-continued

```
tgcagaagct ctgtacccca gagaatatca actgcagaga cacccagggc agaaattcaa  2520
cccctctgca cctggcagca ggctataata acctggaagt agctgaatat cttctagagc  2580
atggagctga tgttaatgcc caggacaagg gtggtttaat tcctcttcat aatgcggcat  2640
cttatgggca tgttgacata gcggctttat tgataaaata caacacgtgt gtaaatgcaa  2700
cagataagtg ggcgtttact cccctccatg aagcagccca gaaaggaagg acgcagctgt  2760
gcgccctcct cctagcgcat ggtgcagacc ccaccatgaa gaaccaggaa ggccagacgc  2820
ctctggatct ggcaacagct gacgatatca gagctttgct gatagatgcc atgcccccag  2880
aggccttacc tacctgtttt aaacctcagg ctactgtagt gagtgcctct ctgatctcac  2940
cagcatccac cccctcctgc ctctcggctg ccagcagcat agacaacctc actggccctt  3000
tagcagagtt ggccgtagga ggagcctcca atgcagggga tggcgccgcg ggaacagaaa  3060
ggaaggaagg agaagttgct ggtcttgaca tgaatatcag ccaatttcta aaaagccttg  3120
gccttgaaca ccttcgggat atctttgaaa cagaacagat tacactagat gtgttggctg  3180
atatgggtca tgaagagttg aaagaaatag gcatcaatgc atatgggcac cgccacaaat  3240
taatcaaagg agtagaaaga ctcttaggtg gacaacaagg caccaatcct tatttgactt  3300
ttcactgtgt taatcaggga acgattttgc tggatcttgc tccagaagat aaagaatatc  3360
agtcagtgga agaagagatg caaagtacta ttcgagaaca cagagatggt ggtaatgctg  3420
gcggcatctt caacagatac aatgtcattc gaattcaaaa agttgtcaac aagaagttga  3480
gggagcggtt ctgccaccga cagaaggaag tgtctgagga gaatcacaac catcacaatg  3540
agcgcatgtt gtttcatggt tctcctttca ttaatgccat tattcataaa gggtttgatg  3600
agcgacatgc atacatagga ggaatgtttg gggccgggat ttattttgct gaaaactcct  3660
caaaaagcaa ccaatatgtt tatggaattg gaggaggaac aggctgccct acacacaagg  3720
acaggtcatg ctatatatgt cacagacaaa tgctcttctg tagagtgacc cttgggaaat  3780
cctttctgca gtttagcacc atgaaaatgg cccacgcgcc tccagggcac cactcagtca  3840
ttggtagacc gagcgtcaat gggctggcat atgctgaata tgtcatctac agaggagaac  3900
aggcataccc agagtatctt atcacttacc agatcatgaa gccagaagcc ccttcccaga  3960
ccgcaacagc cgcagagcag aagacctagt gaatgcctgc tggtgaaggc cagatcagat  4020
ttcaacctgg gactggatta cagaggattg tttctaataa caacatcaat attctagaag  4080
tccctgacag cctagaaata agctgtttgt cttctataaa gcattgctat agtgatgaat  4140
agtatgagta actgatacat actcaactgc tactgttccc tttgaggaaa tgtttacagg  4200
ggcggccttt taacatatct caggctcatt ttcattgcaa ttatccattt ctaaaacaag  4260
attgcttcga tctagacttg gaaatggaaa ataagaaaac caatgctttt tcaaatgttc  4320
acaattcaca cactacattt gttttgttat gcatgacgtg tctataacaa atatacacat  4380
acgacaggca acaagcttgt ttttgatttg ccagacatgc atcattggct attgtttgtt  4440
tgtttttttgt ttttttgtgt tttttgggtt actttgaaaa tgagccagag ccttcttgag  4500
gatattttgc acaaagtcac gctgacaaaa tcattagcag tgcaacccaa gcttctggct  4560
gagcaagatt cagtttccac tttttaaaat ttttttattt tgctctgtag ctgcacttct  4620
cgttatcata aattgagatg aaaaggaaaa aacatcaagt tttagtacct ttttatgaat  4680
tggcctatct tacaagagaa gggcacaaac accaacctga cttaggaacg cctaaattca  4740
gagaagtcaa agccggtgaa ggccacttgc tctttccaac acaagcctgc cacagaggtc  4800
ttcgggacag tactggagat gcaggttgac acgggcttga gttccaaggt gaaaaaactg  4860
```

-continued

```
gggaggctgt gaaggaagag ctgcattaag gagggtgagg agcgtgtggt tctgtatcat   4920
ggcagcccca atggatccag ggatgcctc caaaaaatac atgcttccct tcccttaatc   4980
tgtactgttg ggattgttac ccctccaaat tagctgcctt atttcaaaag tcagtgaaat   5040
tactgcactt gatgagggtc acaaaaatac cacttgattg tttctttagt tgagaatgct   5100
gggattcaga ctcgaatagt ggatagatac acacaaatgc aaggactttt ttgtttactc   5160
cagatttggg gtttattttg agtggcatgc ttcaaatagt tcataaagat ccttgcatta   5220
aatttctgaa ccatttcttc aaacttctta gtgtgtttag acaaggagaa caaaaattga   5280
aaccaaagcc ctttctgtta ttttttcaat gaaggtgaga aagaaatacc atacaatttt   5340
ctttgtgaaa ttactgttta ttttcatcaa catttaccaa gtgccattga catttataaa   5400
aaaaaatgat cctttatagt tcttacactt gccctttca ccttaactga atatgaattg   5460
agtgcactaa cttatttact tgatatactg tgcatctact ctgctttgaa gcgaaagaaa   5520
tataaacacg aggaggaata ggaaagacag tgtgacacaa acttgccatt gcaattcaaa   5580
gccctgaaaa cgatgggttt aatgcaaggt gattaagctg tgacctcctt taatctcctg   5640
aagcaaaata aaatggttac atgcaaaact tctagaaata gactcttaaa atatatacat   5700
tttgctttga ttttggcttc aacccagtgc tggaactagg catccagact agtttgaatg   5760
tttgtagctg aatttttatg ggtcctcaaa attaaatcga gaattagcct cagttgttgc   5820
ttcttttgaa gtttcagtga cccaagctgg gtgtttgtgt cttggctact tgtttaatag   5880
cactagaatt ccaggtgaag ctttgagagt tgatattcat taagagggct tttttcccc   5940
ttctttcctt ctcttttgct gtaacaaagg gttgaagaaa ttgccatctg tgtagttttc   6000
agtagctgtc aagtgtgtct tacttacctt cccccagacg tagtttaaaa tggtaaacac   6060
agctgtgatt tttagttaag taaaagagtt aatatgatat agatatggaa agctttatgg   6120
cttcattaaa aagataaacc actacctaac tgtggttgta tgttgtttcc atcatactaa   6180
ctagatgaat ggatgcgcca gttttcatct tggtccttac acttgagaag ttaaactgtg   6240
gttcagtatt taaactgcca gtgttatacg tctcatgctc tgtgtgccag gtgaaggtac   6300
tgtgtaagga agacatttgc ggtgcttctt gtcctataat gattcaagta tatagtagtt   6360
cttgaaagag tgtgcatata ttactcatct gcttaagaga gtgggttaat ggatatatca   6420
gaggagccaa atacattttt ttcagaactt gaaaaccaaa ggtcatcatg agtgcactca   6480
aaagttagga caagtttatt acatttggga ttttcatctg tagccgtatg aagaaccctt   6540
tccaatataa aagcatggca ttaaattagg ctgaagtctt ttattttttg tatatgtact   6600
atatagaaat actagcaagt taggatcatc caatatggcc taccccgaaa tggcccctct   6660
gtttccctaa ccacatggaa gaaagaatct gaacgtctcc accggctcta cccgagttcc   6720
aaaactaaag ggcttctcca gacctgatgg ttccagttta cctgctgttg gcctgctgga   6780
tacttgactc aggcataaat taagtgccct ggtcccgaac tttctccctg tatttgacct   6840
ccttccctct ttcctaaatt actagtctgg aattaaaatt agctccagca atgacctttg   6900
actccattca ttttctcctc atcttgggtc ttaaaaaagg agaccagata cctcctagct   6960
tttgtatcac aaccaggaat gggtattagg cctcatgcgc tttgctcaga acactgccgc   7020
tttgttaaca aatgacagca tggaacccag agttttgatt cgatgcaaaa taacagcagt   7080
gcaaccagga ttcttgtttt ccttttcctt cttggagttt ggaatttcta gcttttcaag   7140
cagcataagt agaatcaaca ttaggatgtt ttcatgaaat agcatcctta tacttctttg   7200
agcttgatgt tagtggctag actgatttcc ctttgctctc aaaatacaaa gtgcattgaa   7260
gtatacagag aaatgcctga atatggcaag caaataatgt agattaacat tctattattg   7320
```

-continued

```
tatccgtttt acaaaaaata aaattttgat atatgccgga gaacggcatt agaatgcaat  7380
aagttgtcta ggtttttctg tttcagtgtc tctcccaatg gcacgaaggg ttattgggca  7440
ttgtccccac ccccgccttt ttaacatgtg cactatctgg attcctgtaa atggccttgc  7500
aaacagaagt ggtgtgtatt ttcaagcacc tttcccccat tgtatccgaa tccctcttgt  7560
gtgatatctg tgacaaatag ccttcttctt gtgttttctg ttggactaat tgtctcacgt  7620
aaagctatag accttactaa tttggcaggt attcaaaact gccattaaga taggatttca  7680
tgtcagatac gtatttaaag agtaaagtca aatttgttta atgtcagatc agtgacagaa  7740
gtgaaaagaa agtaattgtg aaagtgatgt ttgagctatt gtacacatct agcatatgga  7800
aagcaaatgc actcgaaaac tactattcta gaacatgagg cttcttcagc aacttgtgca  7860
ctctgccatt aataaattaa atttttcccc tctagaaagc cttaactatg gcggaaactt  7920
tttaaccttt tatattttaa taaataaaac attgtagtcc catttcttag tgtttgaaag  7980
gtgtgtcagt gagtcggcca tgtctccatg tgtttcagac ctgttcatct tattttatga  8040
tggtatattt cataagtaat attcccttac atgcaatgga gctgattaaa attaatccat  8100
ttcaatttct ccatattgga acttcctcag ctaccagatt tctggtttgg agaagtgctg  8160
gaaagatttc aaagcctatt cagttgtgta tgtggggata cgacagcaac tgtgatacct  8220
tgtagaatat gagtgatatg caagctgtgt tttttaattg ttttaaaatg taaattatgg  8280
ttatgctaaa gtgaaaacct agaggaagct aatgatttta tatactttgc acgaccaaat  8340
atggtcgtag tatgacgagt tttatacatt gccagagagt tctgcctcct ctgaaataac  8400
attcgcactg tagattgcat ttcggctttt cctcctttca cattcttttt tgctttacac  8460
ttcacgtctt cgcacctgcc ctacctccca tcctttcaaa gaggtttctt tcacgttcca  8520
gaattcagat tgttctgtga tttcttttac atcagtctac ccatttctgc aggcagccct  8580
gaaagccctt gtgttgattc agagtgtttg cagagaaatg cagttgaacc ctggtagtgg  8640
ggtgtccctc acacacccgc gcacccctcc caaagttcag gatgaaaggc tagaaaaccc  8700
attcaaagtt aggaaagaac acagatcttt gaggccgata gcctagacct agaagatgac  8760
cttgagtatg taaacattgt ctccgtgaca caaaacactg aaactcttca tgtgcatata  8820
acacctgctt ctgctcccat tgtttcaagc tcatcttatc tttgtagtag taatgtttgt  8880
ctttgatacc tacaaactaa aaaggtactt ttatcaaggt ttctcaaaac atttacaaaa  8940
ccagctttga gaaaatgtta tgttgcctgg caacagcact cggagtagta attgtgtttt  9000
ctcattgtga tgttggtctg tgtgagcaac cagtgtagtg actctttggt tcattattcg  9060
tgttgttttt atttttagtc tctgtgtgac ccaacagtgg caggggttac aaccccctct  9120
cctttctttt ttgtatttat ctatttgtag gattgtcaga tcaagtacaa gatgcccagt  9180
taagtttgaa tttcagagaa acaatttcac gttaagaatg tttcatgcaa tatttggcat  9240
atatttacag taaaagcatt cattatttgt ctgaaattca aatttaactg agcatgctgg  9300
tttttctcat tgtttggttt ttctaaatct ggcaatccta cagctgtggt catgggaaat  9360
cacctacagc atgttaaagt cctctagtca tcatctcgtc acctgaaatg gaagtccttt  9420
ttccctcacc ctccacttct ttccaaagga gggcatcaag gaacttaacc tgcctgcctg  9480
gtgggtttct atttaagaca tctttgtgat tatatttaac ctgcaattgt gctttggctt  9540
aatgtctagc tcactgtact tgtaaatgat taatattcaa taaaaccatt tttaaagta   9599
```

The human tankyrase 1 protein encoded by this nucleotide sequence is as follows (SEQ ID NO:10):

```
MAASRRSQHH HHHHQQQLQP APGASAPPPP PPPPLSPGLA
PGTTPASPTA SGLAPFASPR HGLALPEGDG SRDPPDRPRS
PDPVDGTSCC STTSTICTVA AAPVVPAVST SSAAGVAPNP
AGSGSNNSPS SSSSPTSSSS SSPSSPGSSL AESPEAAGVS
STAPLGPGAA GPGTGVPAVS GALRELLEAC RNGDVSRVKR
LVDAANVNAK DMAGRKSSPL HFAAGFGRKD VVEHLLQMGA
NVHARDDGGL IPLHNACSFG HAEVVSLLLC QGADPNARDN
WNYTPLHEAA IKGKIDVCIV LLQHGADPNI RNTDGKSALD
LADPSAKAVL TGEYKKDELL EAARSGNEEK LMALLTPLNV
NCHASDGRKS TPLHLAAGYN RVRIVQLLLQ HGADVHAKDK
GGLVPLHNAC SYGHYEVTEL LLKHGACVNA MDLWQFTPLH
EAASKNRVEV CSLLLSHGAD PTLVNCHGKS AVDMAPTPEL
RERLTYEFKG HSLLQAAREA DLAKVKKTLA LEIINFKQPQ
SHETALHCAV ASLHPKRKQV TELLLRKGAN VNEKNKDFMT
PLHVAAERAH NDVMEVLHKH GAKMNALDTL GQTALHRAAL
AGHLQTCRLL LSYGSDPSII SLQGFTAAQM GNEAVQQILS
ESTPIRTSDV DYRLLEASKA GDLETVKQLC SSQNVNCRDL
```

-continued

```
EGRHSTPLHF AAGYNRVSVV EYLLHHGADV HAKDKGGLVP
LHNACSYGHY EVAELLVRHG ASVNVADLWK FTPLHEAAAK
GKYEICKLLL KHGADPTKKN RDGNTPLDLV KEGDTDIQDL
LRGDAALLDA AKKGCLARVQ KLCTPENINC RDTQGRNSTP
LHLAAGYNNL EVAEYLLEHG ADVNAQDKGG LIPLHNAASY
GHVDIAALLI KYNTCVNATD KWAFTPLHEA AQKGRTQLCA
LLLAHGADPT MKNQEGQTPL DLATADDIRA LLIDAMPPEA
LPTCFKPQAT VVSASLISPA STPSCLSAAS SIDNLTGPLA
ELAVGGASNA GDGAAGTERK EGEVAGLDMN ISQFLKSLGL
EHLRDIFETE QITLDVLADM GHEELKEIGI NAYGHRHKLI
KGVERLLGGQ QGTNPYLTFH CVNQGTILLD LAPEDKEYQS
VEEEMQSTIR EHRDGGNAGG IFNRYNVIRI QKVVNKKLRE
RFCHRQKEVS EENHNHHNER MLFHGSPFIN AIIHKGFDER
HAYIGGMFGA GIYFAENSSK SNQYVYGIGG GTGCPTHKDR
SCYICHRQML FCRVTLGKSF LQFSTMKMAH APPGHHSVIG
RPSVNGLAYA EYVIYRGEQA YPEYLITYQI MKPEAPSQTA
TAAEQKT
```

Human tankyrase 2 has a published nucleotide sequence as set forth in Accession No. NM_025235 (SEQ ID NO:11), as follows:

```
ggctggacgg agctggcagg aggggccttg ccagcttccg ccgccgcgtc gtttcaggac    61
ccggacggcg gattcgcgct gcctccgccg ccgcggggca gccgggggc agggagccca    121
gcgaggggcg cgcgtgggcg cggccatggg actgcgccgg atccggtgac agcagggagc   181
caagcggccc gggccctgag cgcgtcttct ccgggggccc tcgccctcct gctcgcgggg   241
ccggggctcc tgctccggtt gctggcgctg ttgctggctg tggcggcggc caggatcatg   301
tcgggtcgcc gctgcgccgg cgggggagcg gcctgcgcga gcgccgcggc cgaggccgtg   361
gagccggccg cccgagagct gttcgaggcg tgccgcaacg gggacgtgga acgagtcaag   421
aggctggtga cgcctgagaa ggtgaacagc cgcgacacgg cgggcaggaa atccaccccg   481
ctgcacttcg ccgcaggttt tgggcggaaa gacgtagttg aatatttgct tcagaatggt   541
gcaaatgtcc aagcacgtga tgatgggggc cttattcctc ttcataatgc atgctctttt   601
ggtcatgctg aagtagtcaa tctccttttg cgacatggtg cagaccccaa tgctcgagat   661
aattggaatt atactcctct ccatgaagct gcaattaaag gaaagattga tgtttgcatt   721
gtgctgttac agcatggagc tgagccaacc atccgaaata cagatggaag gacagcattg   781
gatttagcag atccatctgc caaagcagtg cttactggtg aatataagaa agatgaactc   841
ttagaaagtg ccaggagtgg caatgaagaa aaaatgatgg ctctactcac accattaaat   901
gtcaactgcc acgcaagtga tggcagaaag tcaactccat tacatttggc agcaggatat   961
aacagagtaa agattgtaca gctgttactg caacatggag ctgatgtcca tgctaaagat  1021
aaaggtgatc tggtaccatt acacaatgcc tgttcttatg gtcattatga agtaactgaa  1081
cttttggtca agcatggtgc ctgtgtaaat gcaatggact tgtggcaatt cactcctctt  1141
catgaggcag cttctaagaa cagggttgaa gtatgttctc ttctcttaag ttatggtgca  1201
```

-continued

```
gacccaacac tgctcaattg tcacaataaa agtgctatag acttggctcc cacaccacag  1261
ttaaaagaaa gattagcata tgaatttaaa ggccactcgt tgctgcaagc tgcacgagaa  1321
gctgatgtta ctcgaatcaa aaaacatctc tctctggaaa tggtgaattt caagcatcct  1381
caaacacatg aaacagcatt gcattgtgct gctgcatctc catatcccaa aagaaagcaa  1441
atatgtgaac tgttgctaag aaaaggagca aacatcaatg aaaagactaa agaattcttg  1501
actcctctgc acgtggcatc tgagaaagct cataatgatg ttgttgaagt agtggtgaaa  1561
catgaagcaa aggttaatgc tctggataat cttggtcaga cttctctaca cagagctgca  1621
tattgtggtc atctacaaac ctgccgccta ctcctgagct atgggtgtga tcctaacatt  1681
atatcccttc agggctttac tgctttacag atgggaaatg aaaatgtaca gcaactcctc  1741
caagagggta tctcattagg taattcagag gcagacagac aattgctgga agctgcaaag  1801
gctggagatg tcgaaactgt aaaaaaactg tgtactgttc agagtgtcaa ctgcagagac  1861
attgaagggc gtcagtctac accacttcat tttgcagctg ggtataacag agtgtccgtg  1921
gtggaatatc tgctacagca tggagctgat gtgcatgcta aagataaagg aggccttgta  1981
cctttgcaca atgcatgttc ttatggacat tatgaagttg cagaacttct tgttaaacat  2041
ggagcagtag ttaatgtagc tgatttatgg aaatttacac ctttacatga agcagcagca  2101
aaaggaaaat atgaaatttg caaacttctg ctccagcatg gtgcagaccc tacaaaaaaa  2161
aacagggatg gaaatactcc tttggatctt gttaaagatg gagatacaga tattcaagat  2221
ctgcttaggg gagatgcagc tttgctagat gctgccaaga agggttgttt agccagagtg  2281
aagaagttgt cttctcctga taatgtaaat tgccgcgata cccaaggcag acattcaaca  2341
cctttacatt tagcagctgg ttataataat ttagaagttg cagagtattt gttacaacac  2401
ggagctgatg tgaatgccca agacaaagga ggacttattc ctttacataa tgcagcatct  2461
tacgggcatg tagatgtagc agctctacta ataaagtata atgcatgtgt caatgccacg  2521
gacaaatggg ctttcacacc tttgcacgaa gcagcccaaa agggacgaac acagctttgt  2581
gctttgttgc tagcccatgg agctgacccg actcttaaaa atcaggaagg acaaacacct  2641
ttagatttag tttcagcgga tgatgtcagc gctcttctga cagcagccat gccccccatct 2701
gctctgccct cttgttacaa gcctcaagtg ctcaatggtg tgagaagccc aggagccact  2761
gcagatgctc tctcttcagg tccatctagc ccatcaagcc tttctgcagc cagcagtctt  2821
gacaacttat ctgggagttt ttcagaactg tcttcagtag ttagttcaag tggaacagag  2881
ggtgcttcca gtttggagaa aaaggaggtt ccaggagtag attttagcat aactcaattc  2941
gtaaggaatc ttggacttga gcacctaatg gatatatttg agagagaaca gatcactttg  3001
gatgtattag ttgagatggg gcacaaggag ctgaaggaga ttggaatcaa tgcttatgga  3061
cataggcaca aactaattaa aggagtcgag agacttatct ccggacaaca aggtcttaac  3121
ccatatttaa ctttgaacac ctctggtagt ggaacaattc ttatagatct gtctcctgat  3181
gataaagagt ttcagtctgt ggaggaagag atgcaaagta cagttcgaga gcacagagat  3241
ggaggtcatg caggtggaat cttcaacaga tacaatattc tcaagattca gaaggtttgt  3301
aacaagaaac tatgggaaag atacactcac cggagaaaag aagtttctga agaaaaccac  3361
aaccatgcca atgaacgaat gctatttcat gggtctcctt ttgtgaatgc aattatccac  3421
aaaggctttg atgaaaggca tgcgtacata ggtggtatgt ttggagctgg catttatttt  3481
gctgaaaact cttccaaaag caatcaatat gtatatggaa ttggaggagg tactgggtgt  3541
ccagttcaca aagacagatc ttgttacatt tgccacaggc agctgctctt ttgccgggta  3601
accttgggaa agtctttcct gcagttcagt gcaatgaaaa tggcacattc tcctccaggt  3661
```

-continued

```
catcactcag tcactggtag gcccagtgta aatggcctag cattagctga atatgttatt  3721
tacagaggag aacaggctta tcctgagtat ttaattactt accagattat gaggcctgaa  3781
ggtatggtcg atggataaat agttatttta agaaactaat tccactgaac ctaaaatcat  3841
caaagcagca gtggcctcta cgttttactc ctttgctgaa aaaaaatcat cttgcccaca  3901
ggcctgtggc aaaaggataa aaatgtgaac gaagtttaac attctgactt gataaagctt  3961
taataatgta cagtgttttc taaatatttc ctgtttttttc agcactttaa cagatgccat  4021
tccaggttaa actgggttgt ctgtactaaa ttataaacag agttaacttg aaccttttat  4081
atgttatgca ttgattctaa caaactgtaa tgccctcaac agaactaatt ttactaatac  4141
aatactgtgt tctttaaaac acagcattta cactgaatac aatttcattt gtaaaactgt  4201
aaataagagc ttttgtacta gcccagtatt tatttacatt gctttgtaat ataaatctgt  4261
tttagaactg cagcggttta caaaattttt tcatatgtat tgttcatcta tacttcatct  4321
tacatcgtca tgattgagtg atctttacat ttgattccag aggctatgtt cagttgttag  4381
ttgggaaaga ttgagttatc agatttaatt tgccgatggg agcctttatc tgtcattaga  4441
aatctttctc atttaagaac ttatgaatat gctgaagatt taatttgtga tacctttgta  4501
tgtatgagac acattccaaa gagctctaac tatgataggt cctgattact aaagaagctt  4561
ctttactggc ctcaatttct agctttcatg ttggaaaatt ttctgcagtc cttctgtgaa  4621
aattagagca aagtgctcct gttttttaga gaaactaaat cttgctgttg aacaattatt  4681
gtgttctttt catggaacat aagtaggatg ttacatttcc agggtgggaa gggtaatcct  4741
aaatcatttc ccaatctatt ctaattacct taaatctaaa ggggaaaaaa aaaatcacaa  4801
acaggactgg gtagtttttt atcctaagta tattttttcc tgttcttttt acttggtttt  4861
attgctgtat ttatagccaa tctatacatc atgggtaaac ttaacccaga actataaaat  4921
gtagttgtct cagtcccctc caggcctcct gaatgggcaa gtgcagtgaa acaggtgctt  4981
cttgctcctg ggttttctct ccatgatgtt atgcccaatt ggaaatatgc tgtcagtttg  5041
tgcaccatat ggtgaccacg cctgtgctca gtttggcagc tatagaagga aatgctgtcc  5101
cataaaatgc cattcctatt ttctaatata aaactctttt ccaggaagca tgcttaagca  5161
tcttgttaca gagacataca tccattatgg cttggcaatc tcttttattt gttgactcta  5221
gctcccttca aagtcgagga aagatcttta ctcacttaat gaggacattc cccatcactg  5281
tctgtaccag ttcaccttta ttttacgttt tattcagtct gtaaattaac tggccctttg  5341
cagtaacttg tacataaagt gctagaaaat catgttcctt gtcctgagta agagttaatc  5401
agagtaaatg catttctgga gttgtttctg tgatgtaaat tatgatcatt atttaagaag  5461
tcaaatcctg atcttgaagt gcttttttata cagctctcta ataattacaa atatccgaaa  5521
gtcatttctt ggaacacaag tggagtatgc caaattttat atgaattttt cagattatct  5581
aagcttccag gttttataat tagaagataa tgagagaatt aatggggttt atatttacat  5641
tatctctcaa ctatgtagcc catattactc accctatgag tgaatctgga attgcttttc  5701
atgtgaaatc attgtggtct atgagtttac aatactgcaa actgtgttat tttatctaat  5761
ccattgctta atgagtgtgt ttttccatga atgaatatac cgtggttcat atgttagcat  5821
ggcagcattt tcagatagct ttttgtttgt tgggaagttg gggttttggg gggaggggga  5881
gtattagtac gttgcatgaa atagcttact ttataatgat ggaattgctt tttcttttgt  5941
cttgtgattt ttttttttga agtgaaattt aacttttttgt gcaagtagta ctattatacc  6001
catcttcagt gtcttacttg tactgtatca cattccatac cctcatttaa ttcttaataa  6061
```

-continued

```
aactgttcac ttgtttttct gggtagcatg gtaattactg gaatagtata aatgtgttga  6121

atggtctttg agaaaatgaa ttaagattac aataaaccac aattgcagga aaacaatgta  6181

gttctgagtc taatagtgat aaagaatgca gtttgaagtt tgaaatattg aatattgtag  6241

ctgtacttgc tcattaaaat gaaagtagct gtga
```

The human tankyrase 2 protein encoded by this nucleotide sequence is as follows (SEQ ID NO:12):

```
MSGRRCAGGG AACASAAAEA VEPAARELFE ACRNGDVERV
KRLVTPEKVN SRDTAGRKST PLHFAAGFGR KDVVEYLLQN
GANVQARDDG GLIPLHNACS FGHAEVVNLL LRHGADPNAR
DNWNYTPLHE AAIKGKIDVC IVLLQHGAEP TIRNTDGRTA
LDLADPSAKA VLTGEYKKDE LLESARSGNE EKMMALLTPL
NVNCHASDGR KSTPLHLAAG YNRVKIVQLL LQHGADVHAK
DKGDLVPLHN ACSYGHYEVT ELLVKHGACV NAMDLWQFTP
LHEAASKNRV EVCSLLLSYG ADPTLLNCHN KSAIDLAPTP
QLKERLAYEF KGHSLLQAAR EADVTRIKKH LSLEMVNFKH
PQTHETALHC AAASPYPKRK QICELLLRKG ANINEKTKEF
LTPLHVASEK AHNDVVEVVV KHEAKVNALD NLGQTSLHRA
AYCGHLQTCR LLLSYGCDPN IISLQGFTAL QMGNENVQQL
LQEGISLGNS EADRQLLEAA KAGDVETVKK LCTVQSVNCR
DIEGRQSTPL HFAAGYNRVS VVEYLLQHGA DVHAKDKGGL
VPLHNACSYG HYEVAELLVK HGAVVNVADL WKFTPLHEAA
AKGKYEICKL LLQHGADPTK KNRDGNTPLD LVKDGDTDIQ
DLLRGDAALL DAAKKGCLAR VKKLSSPDNV NCRDTQGRHS
TPLHLAAGYN NLEVAEYLLQ HGADVNAQDK GGLIPLHNAA
SYGHVDVAAL LIKYNACVNA TDKWAFTPLH EAAQKGRTQL
CALLLAHGAD PTLKNQEGQT PLDLVSADDV SALLTAAMPP
SALPSCYKPQ VLNGVRSPGA TADALSSGPS SPSSLSAASS
LDNLSGSFSE LSSVVSSSGT EGASSLEKKE VPGVDFSITQ
FVRNLGLEHL MDIFEREQIT LDVLVEMGHK ELKEIGINAY
GHRHKLIKGV ERLISGQQGL NPYLTLNTSG SGTILIDLSP
DDKEFQSVEE EMQSTVREHR DGGHAGGIFN RYNILKIQKV
CNKKLWERYT HRRKEVSEEN HNHANERMLF HGSPFVNAII
HKGFDERHAY IGGMFGAGIY FAENSSKSNQ YVYGIGGGTG
CPVHKDRSCY ICHRQLLFCR VTLGKSFLQF SAMKMAHSPP
GHHSVTGRPS VNGLALAEYV IYRGEQAYPE YLITYQIMRP
EGMVDG
```

Pharmaceutical compositions containing a tankyrase inhibitor suitable for use in the methods of the present invention can include a pharmaceutically acceptable carrier as described infra, one or more active agents (i.e., the tankyrase inhibitor), and a suitable delivery vehicle. Suitable delivery vehicles include, but are not limited to, viruses, bacteria, biodegradable microspheres, microparticles, nanoparticles, liposomes, collagen minipellets, and cochleates.

In one embodiment, the pharmaceutical composition or formulation containing an inhibitory nucleic acid molecule (e.g., siRNA molecule) is encapsulated in a lipid formulation to form a nucleic acid-lipid particle as described in Semple et al., "Rational Design of Cationic Lipids for siRNA Delivery," *Nature Biotech.* 28:172-176 (2010), PCT Publication No. WO 2011/034798 to Bumcrot et al., PCT Publication No. WO 2009/111658 to Bumcrot et al., and PCT Publication No. WO 2010/105209 to Bumcrot et al., which are hereby incorporated by reference in their entirety.

In another embodiment, the delivery vehicle is a nanoparticle. A variety of nanoparticle delivery vehicles are known in the art and are suitable for delivery of a tankyrase inhibitor (see e.g., van Vlerken et al., "Multi-functional Polymeric Nanoparticles for Tumour-Targeted Drug Delivery," *Expert Opin. Drug Deliv.* 3(2):205-216 (2006), which is hereby incorporated by reference in its entirety). Suitable nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly (ethylene glycol) copolymers (Park et al., "Degradable Polyethylenimine-alt-Poly(ethylene glycol) Copolymers As Novel Gene Carriers," *J. Control Release* 105(3):367-80 (2005) and Park et al., "Intratumoral Administration of Anti-KITENIN shRNA-Loaded PEI-alt-PEG Nanoparticles Suppressed Colon Carcinoma Established Subcutaneously in Mice," *J. Nanosci. Nanotechnology* 10(5):3280-3 (2010), which are hereby incorporated by reference in their entirety), and liposome-entrapped siRNA nanoparticles (Kenny et al., "Novel Multifunctional Nanoparticle Mediates siRNA Tumor Delivery, Visualization and Therapeutic Tumor Reduction In Vivo," *J. Control Release* 149(2):111-116 (2011), which is hereby incorporated by reference in its entirety). Other nanoparticle delivery vehicles suitable for use in the present invention include microcapsule nanotube devices disclosed in U.S. Patent Publication No. 2010/0215724 to Prakash et al., which is hereby incorporated by reference in its entirety.

In another embodiment, the pharmaceutical composition is contained in a liposome delivery vehicle. The term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Several advantages of liposomes include: their biocompatibility and biodegradability, incorporation of a wide range of water and lipid soluble drugs; and they afford protection to encapsulated drugs from metabolism and degradation. Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Methods for preparing liposomes for use in the present invention include those disclosed in Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda, and U.S. Pat. No. 5,059,421 to Loughrey et al., which are hereby incorporated by reference in their entirety.

A liposome containing a tankyrase inhibitor can be contacted with the target primary cancer (or tumor) cells under conditions effective for delivery of the inhibitory agent into the cancer (or tumor) cell. For administration to a primary tumor site, the liposomal vesicles need not be targeted to the cancer (or tumor) cells per se.

A liposome and nanoparticle delivery system can be made to accumulate at a target organ, tissue, or cell via active targeting (e.g., by incorporating an antibody or other ligand on the surface of the delivery vehicle). For example, when the target cell is a cancer (or tumor) cell as in the present invention, delivery vehicle may be conjugated to an anti-C3B(I) antibody as disclosed by U.S. Pat. No. 6,572,856 to Taylor et al., which is hereby incorporated by reference in its entirety. Alternatively, the delivery vehicle may be conjugated to an alphafeto protein receptor as disclosed by U.S. Pat. No. 6,514,685 to Moro, or to a monoclonal GAH antibody as disclosed by U.S. Pat. No. 5,837,845 to Hosokawa, both of which are hereby incorporated by reference in their entirety.

In another embodiment, the delivery vehicle is a viral vector. Viral vectors are particularly suitable for the delivery of inhibitory nucleic acid molecules, such as siRNA or shRNA molecules, but can also be used to deliver molecules encoding an anti-tankyrase antibody. Suitable gene therapy vectors include, without limitation, adenoviral vectors, adeno-associated viral vectors, retroviral vectors, lentiviral vectors, and herpes viral vectors.

Adenoviral viral vector delivery vehicles can be readily prepared and utilized as described in Berkner, "Development of Adenovirus Vectors for the Expression of Heterologous Genes," *Biotechniques* 6:616-627 (1988); Rosenfeld et al., "Adenovirus-Mediated Transfer of a Recombinant Alpha 1-Antitrypsin Gene to the Lung Epithelium In Vivo," *Science* 252:431-434 (1991); PCT Publication No. WO 93/07283 to Curiel et al.; PCT Publication No. WO 93/06223 to Perricaudet et al.; and PCT Publication No. WO 93/07282 to Curiel et al., which are hereby incorporated by reference in their entirety. Adeno-associated viral delivery vehicles can be constructed and used to deliver an inhibitory nucleic acid molecule of the present invention to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-associated Virus Antisense Vector," *Science* 258:1485-1488 (1992); Ponnazhagan et al., "Suppression of Human Alpha-Globin Gene Expression Mediated by the Recombinant Adeno-associated Virus 2-Based Antisense Vectors," *J. Exp. Med.* 179:733-738 (1994); and Zhou et al., "Adeno-associated Virus 2-Mediated Transduction and Erythroid Cell-specific Expression of a Human Beta-globin Gene," *Gene Ther.* 3:223-229 (1996), which are hereby incorporated by reference in their entirety. In vivo use of these vehicles is described in Flotte et al., "Stable In Vivo Expression of the Cystic Fibrosis Transmembrane Conductance Regulator With an Adeno-Associated Virus Vector," *PNAS* 90:10613-10617 (1993) and Kaplitt et al., "Long-Term Gene Expression and Phenotypic Correction Using Adeno-associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver a nucleic acid molecule to a target cell or tissue. One such type of retroviral vector is disclosed in U.S. Pat. No. 5,849,586 to Kriegler et al., which is hereby incorporated by reference in its entirety. Other suitable nucleic acid delivery vehicles include those disclosed in U.S. Patent Application Publication No. 2007/0219118 to Lu et al., which is hereby incorporated by reference in its entirety.

Regardless of the type of infective transformation system employed, it should be targeted for delivery of the nucleic acid to the desired cell type. For example, for delivery into a cluster of cells (e.g., cancer or tumor cells) a high titer of the infective transformation system can be injected directly within the site of those cells so as to enhance the likelihood of cell infection. The infected cells will then express the inhibitory nucleic acid molecule targeting the inhibition of integrin expression. The expression system can further contain a promoter to control or regulate the strength and specificity of expression of the nucleic acid molecule in the target tissue or cell.

In one embodiment, the administering step is carried out to treat a tumor in a subject. Such administration can be carried out systemically or via direct or local administration to the tumor or tumor site. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterialy, intralesionally, or by application to mucous membranes. Suitable modes of local administration include, without limitation, catheterization, implantation, direct injection, dermal/transdermal application, or portal vein administration to relevant tissues, or by any other local administration technique, method, or procedure generally known in the art. The mode of affecting delivery of an agent will vary depending on the type of therapeutic agent (e.g., an antibody, an inhibitory nucleic acid molecule, or a small molecule) and the tumor or cancer to be treated.

A tankyrase inhibitor of the present invention may be orally administered, for example, with an inert diluent, or with an assimilable edible carrier, or it may be enclosed in hard or soft shell capsules, or it may be compressed into tablets, or it may be incorporated directly with the food of the diet. Tankyrase inhibitors may also be administered in a time release manner incorporated within such devices as time-release capsules or nanotubes. Such devices afford flexibility relative to time and dosage. For oral therapeutic administration, tankyrase inhibitors may be incorporated with excipients and used in the form of tablets, capsules, elixirs, suspensions, syrups, and the like. Such compositions and preparations should contain at least 0.1% of the inhibitor, although lower concentrations may be effective and indeed optimal. The percentage of the inhibitor in these compositions may, of course, be varied and may be between about 0.1% to about 60% of the weight of the unit. The amount of an inhibitor of the present invention in such therapeutically useful compositions is such that a suitable dosage will be obtained.

When the tankyrase inhibitor of the present invention is administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, may be preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver a tankyrase inhibitor systemically, it may be formulated for parenteral administration by injection, e.g., by bolus injection or continuous infusion. Formulations for injection may be presented in unit dosage form, e.g., in ampoules or in multi-dose containers, with an added preservative. The composition may take such forms as suspensions, solutions, or emulsions in oily or aqueous vehicles, and may contain formulatory agents such as suspending, stabilizing, and/or dispersing agents.

Intraperitoneal or intrathecal administration of tankyrase inhibitors can also be achieved using infusion pump devices. Such devices allow continuous infusion of desired compounds avoiding multiple injections and multiple manipulations.

In addition to the formulations described previously, the inhibitors may also be formulated as a depot preparation. Such long acting formulations may be formulated with suitable polymeric or hydrophobic materials (e.g., as an emulsion in an acceptable oil) or ion exchange resins, or as sparingly soluble derivatives, e.g., as a sparingly soluble salt Effective doses of the compositions containing an inhibitor may vary depending upon many different factors, including type and stage of the tumor or cancer, means of administration, target site, physiological state of the subject, other medications or therapies administered, and physical state of the subject relative to other medical complications. Treatment dosages may need to be titrated to optimize safety and efficacy.

For the treatment of tumors, tankyrase inhibitors can be administered to a subject in need of treatment alone, or in combination with other antitumor or anticancer substances and/or with radiation therapy and/or with surgical treatment to remove a tumor or cancerous tissue. These other substances or radiation treatments may be given at the same or different times as administering the inhibitor. For example, administration of an inhibitor can be used in combination with mitotic inhibitors, such as taxol or vinblastine; alkylating agents, such as cisplatin, cyclophosamide, or ifosfamide; antimetabolites, such as 5-fluorouracil or hydroxyurea; DNA intercalators, such as adriamycin or bleomycin; topoisomerase inhibitors, such as etoposide or camptothecin; antiangiogenic agents, such as angiostatin; antiestrogens, such as tamoxifen; and/or other drugs or antibodies that inhibit cancer or tumor cells, such as, for example, GLEEVEC (Novartis) and HERCEPTIN (Genetech).

In accordance with all aspects of the present invention, a "subject" encompasses any animal, but preferably a mammal, e.g., human, non-human primate, a dog, a cat, a horse, a cow, or a rodent. More preferably, the subject is a human.

As used herein, a "tumor" is any kind of new growth, benign or malignant.

Another aspect of the present invention is directed to a method of treating cancer in a subject. This method involves administering to a subject having a cancer comprising a Hippo pathway mutant tumor susceptible to treatment with a tankyrase inhibitor a tankyrase inhibitor, where the tankyrase inhibitor treats the subject for cancer.

As used herein, the term "cancer" refers to a form of a tumor, namely malignant. Cancers and tumors to be treated according to the methods of the present invention include, without limitation, carcinoma of the bladder, breast, colon, kidney, liver, lung, head and neck, gall-bladder, ovary, pancreas, stomach, cervix, thyroid, prostate, or skin; a hematopoietic tumor of lymphoid lineage (i.e., leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); a hematopoietic tumor of myeloid lineage (i.e., acute myelogenous leukemia, chronic myelogenous leukemia, multiple myelogenous leukemia, myelodysplastic syndrome, and promyelocytic leukemia); a tumor of mesenchymal origin (i.e., fibrosarcoma and rhabdomyosarcoma); a tumor of the central or peripheral nervous system (i.e., astrocytoma, neuroblastoma, glioma, and schwannomas); melanoma; seminoma; teratocarcinoma; osteosarcoma; thyroid follicular cancer; Kaposi's sarcoma; hepatoma; and mesothelioma.

A further aspect of the present invention relates to a method of identifying a subject as a candidate for treatment. This method involves obtaining a tissue sample from a tumor in a subject and determining whether the tumor is a Hippo pathway mutant tumor susceptible to treatment with a tankyrase inhibitor. A determination that the tumor is a Hippo pathway mutant tumor susceptible to treatment with a tankyrase inhibitor, as described supra and, e.g., as exemplified in the Examples infra, identifies the subject as a candidate for treatment.

According to one embodiment, determining whether the tumor is a Hippo pathway mutant tumor susceptible to treatment with a tankyrase inhibitor comprises determining the level and durability of angiomotin stabilization in the tumor sample following treatment with a tankyrase inhibitor, as described supra.

In one embodiment of this aspect of the present invention, a course of treatment is assigned to the subject based on determining whether the tumor is a Hippo pathway mutant tumor susceptible to treatment with a tankyrase inhibitor. Determining whether the tumor is a Hippo pathway mutant tumor susceptible to treatment with a tankyrase inhibitor is described supra. Assigning a suitable treatment can involve assigning a treatment as described supra. For example, and according to one embodiment, the assigned course of treatment comprises administering a tankyrase inhibitor as described supra, for an extended period of time beyond that used to determine whether the Hippo pathway mutant tumor susceptible to treatment with a tankyrase inhibitor.

According to another embodiment, the method further comprises carrying out an assigned course of treatment, such as a administering a tankyrase inhibitor.

The details described supra regarding other aspects of the present invention also apply to carrying the method of this aspect of the present invention.

EXAMPLES

The following examples are provided to illustrate embodiments of the present invention but they are by no means intended to limit its scope.

Materials and Methods

Cell Culture and Treatments 293 (CRL-1573), 293T (CRL-3216), MCF10A (CRL-10317), H2052 (CRL-5915), 211H (CRL-2081), and H2373 (CRL-5943) were obtained from ATCC. MESO25 was a gift from J. Testa (Fox Chase Cancer Center, Philadelphia, Pa., USA). 293 and 293T cells were cultured in Dulbecco's Modified Eagle's Medium ("DMEM") (Invitrogen, Carlsbad, Calif.) supplemented with 10% Fetal Bovine Serum ("FBS") (Sigma-Aldrich, St. Louis, Mo.) and 50 units/ml of penicillin/streptomycin. H2373, MESO25, MSTO-211H (211H), and H2052 cells were cultured in RPMI-1640 medium supplemented with 10% FBS and 50 units/ml of penicillin/streptomycin. MCF10A cells were grown in DMEM/F12 medium supplemented with 5% horse serum, 10 μg/ml insulin, 100 ng/ml cholera toxin, 0.5 mg/ml hydrocortisone, 20 ng/ml EGF, and 50 units/ml of penicillin/streptomycin. Cells were cultured at 37° C. and 90% humidity in a 5% $CO_2$ incubator. Cycloheximide was purchased from Sigma (Saint Louis, Mo., USA). The following inhibitors were used: XAV939 (Maybridge, #03920SC), MN-64 (Sigma, #SML1012), IWR1 (Sigma, 40161), PARP1/2 inhibitor, ABT-888 (Veliparib, Selleck Chemicals, #S1004), and verteporfin (Sigma, # SML:0534-5MG). Each inhibitor was dissolved in DMSO and was used at the indicated concentration in medium including 0.1% DMSO. In all experiments, 0.1% DMSO in medium was used as control. Selectable markers to generate stably transduced cells were used as follows: 2 μg/ml puromycin (Calbiochem, San Diego, Calif., USA), 400 μg/ml hygromycin B (Invitrogen, Carlsbad, Calif., USA), and 1 μg/ml doxycycline (Sigma, Saint Louis, Mo., USA).

Plasmids and Viral Infections

A TEAD reporter was generated by cloning 10 copies of GT-IIC motif (GTGGAATGT) into a NV-Luciferase vector (Akiri et al., "Wnt Pathway Aberrations Including Autocrine Wnt Activation Occur At High Frequency in Human Non-Small-Cell Lung Carcinoma," *Oncogene* 28(21):2163-2172 (2009), which is hereby incorporated by reference in its entirety) using ClaI and NheI restriction sites. pQCXIH-Myc-YAP, pQCXIH-Flag-YAP-5127A and pQCXIH-Myc-594A were purchased from Addgene (Plasmid #33091, #33092, and #33094). The pQCXIH vector control was generated by removing YAP and religating the vector backbone. pBABE-puro and pBabe-puro-HRAS-V12 vectors were previously described (Mahale et al., "Clonal Selection in Malignant Transformation of Human Fibroblasts Transduced with Defined Cellular Oncogenes," *Cancer Research* 68(5):1417-1426 (2008), which is hereby incorporated by reference in its entirety). dnTEAD4 was cloned from the pSPORT6 Vector (Dharmacon, Lafayette, Colo., USA) into NSPI-CMV-MCS lentiviral vector (Benson et al., "p53-Dependent Gene Repression Through p21 is Mediated By Recruitment of E2F4 Repression Complexes," *Oncogene* 33(30):3959-3969 (2014), which is hereby incorporated by reference in its entirety) using the following primers containing Nhe1 and BamH1 restriction sites:

```
                                        (SEQ ID NO: 13)
FW-TAAGCAGCTAGCGCCACCTTGGAGGGCACGGCCGGCAC
and

                                        (SEQ ID NO: 14)
Rev-ACTATGGGATCCTCATTCTTTCACCAGCCTGTGGATGTGGTGCTG

AGC.
```

The dominant negative (dn) mutation, Y429H (TAC-->CAC) (Zhao et al., "TEAD Mediates YAP-Dependent Gene Induction and Growth Control," *Genes & Dev.* 22(14):1962-1971 (2008), which is hereby incorporated by reference in its entirety), was introduced into TEAD4 gene by site-directed mutagenesis. Stable shRNA and inducible shRNA vectors were generated by cloning the oligos into pLKO.1 or pLKO-Tet-Puro vectors, respectively. Retro and lentivirus production and infection were carried out as previously described (Benson et al., "p53-Dependent Gene Repression Through p21 is Mediated By Recruitment of E2F4 Repression Complexes," *Oncogene* 33(30):3959-3969 (2014), which is hereby incorporated by reference in its entirety).

Small-Molecule Inhibitor Screen and Reporter Luciferase Assay

A set of in-house kinase and commercially available inhibitors was used to screen for effects on the TEAD luciferase reporter. 293 cells expressing the TEAD reporter along with *renilla*-lucifease (20:1 ratio) were plated at low density ($2\times10^4$ cells) in 24 well plates in triplicate. 24 hours after plating, the cells were treated with 10 μM of each compound or DMSO as control. 24 hours later, dual-luciferase reporter assay was performed according to the manufacturer's protocol (Promega, Madison Wis., USA), using TD-20e Luminometer (Turner Biosystem, Promega, Madison Wis., USA). TEAD reporter activity was normalized to *renilla* luciferase. The Log 2 values were calculated for each compound using the DMSO sample as control. Potential hits were repeated in both 293 and 293T cells with similar results.

Cell Proliferation Assay

For clonogenic proliferation assay, cells were plated in triplicate at $1\times10^3$ cells in 6-well plates. For analysis of the effects of inhibitors on cell proliferation, fresh medium with inhibitor was replaced every 48 hours. After 10 to 14 days of treatment, cultures were fixed and stained with 1% crystal violet (in ethanol) and photographed.

Anchorage-Independent Growth Assay

For analysis of anchorage-independent growth, $2.5 \times 10^3$ MCF10A or MCF10A cells stably expressing lentiviral or retroviral transduced cDNAs as indicated were seeded in triplicate in 1 ml of growth media containing 0.3% agar (BD #214050) on top of 1 ml of 0.48% agar in 35 mm dishes. Cells were fed every 4 days for 3 weeks by adding 0.2 mL of growth medium containing either 0.1% DMSO as a control or compounds in 0.1% DMSO at the concentrations indicated. Colonies were then fixed and stained with 1% crystal violet (in ethanol) and photographed.

Extraction and cDNA Synthesis

Total RNA was extracted from cells using the RNeasy Mini kit (Qiagen, Hilden, Germany) following the manufacturer's instructions. 1 μg of total RNA was used for cDNA synthesis using Superscript II (Invitrogen, Carlsbad, Calif., USA) according to the manufacturer's instructions.

Quantitative Real-Time PCR Analysis

Quantitative RT-PCR was performed using the ViiA™ 7 Real-Time PCR System (Life Technologies, Carlsbad, Calif., USA) using the FastStart SYBR Green Master mix (Roche, Indianapolis, Ind., USA). Primers were as follows:

```
CTGF:
                                    (SEQ ID NO: 15)
FW-CCAATGACAACGCCTCCTG,
                                    (SEQ ID NO: 16)
Rev-TGGTGCAGCCAGAAAGCTC;

CYR61:
                                    (SEQ ID NO: 17)
FW-AGCCTCGCATCCTATACAACC,
                                    (SEQ ID NO: 18)
Rev-TTCTTTCACAAGGCGGCACTC;

ANKRD1:
                                    (SEQ ID NO: 19)
FW-CACTTCTAGCCCACCCTGTGA,
                                    (SEQ ID NO: 20)
Rev-CCACAGGTTCCGTAATGATTT;

YAP:
                                    (SEQ ID NO: 21)
FW-TAGCCCTGCGTAGCCAGTTA,
                                    (SEQ ID NO: 22)
Rev TCATGCTTAGTCCACTGTCTGT,

AMOT:
                                    (SEQ ID NO: 23)
FW-ACTACCACCACCTCCAGTCA,
                                    (SEQ ID NO: 24)
Rev-ACAAGGTGACGACTCTCTGC;

AMOTL1:
                                    (SEQ ID NO: 25)
FW-GCAGACAGGAAAACTGAGGA,
                                    (SEQ ID NO: 26)
REV-AAATGTGGTGGGAACAGAGA;

AMOTL2:
                                    (SEQ ID NO: 27)
FW-GCTACTGGGGTAGCAACTGA,
                                    (SEQ ID NO: 28)
Rev-GAAGGCAGTGAGGAACTGAA;

TNKS1:
                                    (SEQ ID NO: 29)
FW-GACCCAAACATTCGGAACAC,
                                    (SEQ ID NO: 30)
Rev-GCAGCTTCTAGGAGTTCGTCTT;

TNKS2:
                                    (SEQ ID NO: 31)
FW-AACGAGTCAAGAGGCTGGTG,
```

-continued

```
                                    (SEQ ID NO: 32)
REV-TTCAACTACGTCTTTCCGCC;

GAPDH:
                                    (SEQ ID NO: 33)
FW-CTCTGCTCCTCCTGTTCGAC
                                    (SEQ ID NO: 34)
Rev-TTAAAAGCAGCCCTGGTGAC.
```

PCR was performed in 384 well plates in 10 μl total volumes under the following conditions: 95° C. for 15 min, followed by 40 cycles of 94° C. for 15 sec, 61° C. for 30 sec, and 72° C. for 30 sec. Specificity was verified by a dissociation curve. Results were analyzed with ViiA7 RUO software (Life Technologies, Carlsbad, Calif., USA). Gene expression levels were normalized to GAPDH expression.

Western Blot Analysis

Cells were harvested in EBC lysis buffer (50 mM Tris-HCl at pH 7.5, 150 mM NaCl, 5 mM EDTA, 0.5% NP-40), supplemented with Complete Mini Protease and Phosphatase Inhibitor Cocktails (Roche, Indianapolis, Ind., USA). Cells were lysed and 30-80 μg protein subjected to SDS-PAGE followed by transfer onto an Immobilon-FL PVDF membrane (Millipore, Billerica, Mass., USA) and incubation with the indicated antibodies. Detection was carried out with an Odyssey Infrared Imaging System (LI-COR Biosciences, Lincoln, Nebr., USA) with IR dye-tagged secondary antibodies (LI-COR Biosciences). The following antibodies were utilized: mouse anti-YAP, goat anti-NF2, mouse anti-AMOT, goat anti-AMOTL1, goat anti-AMOTL2 (Santa Cruz, Dallas, Tex., USA), mouse anti-FlagM2 (Sigma, Saint Louis, Mo., USA), rabbit anti-LATS1, rabbit anti-LATS2, rabbit anti-p-YAP (Cell Signaling, Danvers, Mass., USA), TNKS1/2 (Santa Cruz, Dallas, Tex., USA), mouse anti-TEAD4, mouse anti-RAS (Thermo Scientific, Waltham, Mass., USA), mouse anti-α-Tubulin, mouse anti-β-actin (Sigma, Saint Louis, Mo., USA).

Immunoprecipitation Analysis

Cells were harvested in RIPA lysis buffer (50 mM Tris-Cl; pH 8.0, 5 mM EDTA, 1% Triton X-100, 0.1% sodium deoxycholate, 0.1% SDS, 150 mM NaCl) supplemented with Complete Mini Protease and Phosphatase Inhibitor Cocktails. 800 μg proteins were incubated with 10 μg of antibody overnight at 4° C. Anti-mouse or anti-rabbit IgG (Santa Cruz, Dallas, Tex., USA) was used as a negative control. Immunoprecipitated complexes were captured by 2 h incubation at 4° C. with Dynabeads Protein A/G B (Invitrogen, Carlsbad, Calif., USA), followed by three washes in lysis buffer. Immunoprecipitated complexes were eluted by boiling for 5 min with Laemmli buffer (150 mM Tris-Cl; pH 6.8, 20% glycerol, 4% SDS, 0.002% bromophenol blue, 2% 2-mercaptoethanol) with 10% of the total lysates run on the same gel for comparative immunoblot analysis.

Immunofluorescence Microscopy

Cells cultured on glass coverslips were fixed for 10 min with 4% paraformaldehyde in 1×PBS at 37° C. and permeabilized for 3 min with 0.02% Triton-X100, following exposure for 1 hour to a blocking solution (PBS containing 5% BSA). Coverslips were then incubated at room temperature with the following primary antibodies: anti-YAP (Santa Cruz, Dallas, Tex., USA) and anti-Flag M2 (Sigma, Saint Louis, Mo., USA). Corresponding secondary antibodies were Alexa fluor conjugated (Molecular Probes, Eugene, Oreg., USA). 2 μg/ml DAPI was used as a counter stain and was used to label nuclei. Imaging was performed using an Axioplan 2 Imaging System (Zeiss, Oberkochen, Germany).

Example 1—Hippo Pathway Mutant Tumor Cells are Reliant on High Constitutive TEAD Transcriptional Activity for Proliferation The Hippo pathway regulates cell proliferation in response to cell density and external stimuli such as serum deprivation (Yu et al., "Regulation of the Hippo-YAP Pathway by G-Protein-Coupled Receptor Signaling," *Cell* 150 (4):780-791 (2012); Zhao et al., "Inactivation of YAP Oncoprotein by the Hippo Pathway is Involved in *Cell* Contact Inhibition and Tissue Growth Control," *Genes & Dev.* 21(21):2747-2761 (2007); Aragona et al., "A Mechanical Checkpoint Controls Multicellular Growth Through YAP/TAZ Regulation by Actin-Processing Factors," *Cell* 154(5): 1047-1059 (2013), which are hereby incorporated by reference in their entirety). To characterize the effects of recurrent mutations in Hippo pathway core components on the proliferation of human tumor cells, TEAD transcriptional activity was measured in several tumor lines bearing loss of function mutations in NF2 (H2373, MESO25), LATS1 (MSTO-211H (211H)), and NF2/LATS2 (H2052) or in immortalized non-tumorigenic (293T, MCF10A) cell lines, which are wild-type for NF2, LATS1, and LATS2 genes (FIG. 2A). Using a TEAD luciferase reporter assay, it was observed that tumor lines harboring Hippo pathway mutations showed much higher reporter levels, which were insensitive to serum deprivation or high cell density as compared to Hippo pathway wild-type lines (FIG. 1A). An antibody that recognizes both YAP and TAZ proteins detected higher YAP levels in each line. Of note, YAP protein levels were markedly higher in Hippo mutant as compared to wild-type cells despite their similar mRNA levels (FIGS. 2A-B).

To determine how inhibition of TEAD-mediated transcription influenced cell proliferation, a dominant negative mutant form of TEAD4 (dnTEAD4) was stably expressed that is unable to interact with YAP to drive gene transcription (Zhao et al., "TEAD Mediates YAP-Dependent Gene Induction and Growth Control," *Genes & Dev.* 22(14):1962-1971 (2008), which is hereby incorporated by reference in its entirety) (FIG. 2C, FIG. 2E, and FIGS. 2G-J). Expression of dnTEAD4 effectively decreased TEAD reporter activity in both Hippo wild-type and mutant cells (FIG. 1B). Moreover, expression levels of well-recognized TEAD target genes (CYR61 and CTGF) (Yu et al., "Regulation of the Hippo-YAP Pathway by G-Protein-Coupled Receptor Signaling," *Cell* 150(4):780-791 (2012); Zhao et al., "TEAD Mediates YAP-Dependent Gene Induction and Growth Control," *Genes & Dev.* 22(14):1962-1971 (2008), which are hereby incorporated by reference in their entirety) were significantly decreased under these conditions (FIG. 1C and FIGS. 2D-F). Of note, dnTEAD4 expression markedly inhibited the proliferation of Hippo mutant cell lines but had no detectable effect on colony formation by Hippo pathway wild-type lines (FIG. 1D). These data demonstrate that tumor cells with loss of function mutations in the Hippo pathway core components were dependent on high TEAD transcriptional activity for their proliferation even in serum containing medium. In contrast, cells that lacked mutations in the pathway exhibited low, regulatable TEAD transcriptional activity, which was dispensable for their proliferation. Thus, it was hypothesized that pharmacological inhibitors of TEAD transcriptional activity might specifically antagonize the transformed phenotype of Hippo pathway deregulated tumor cells.

Example 2—A Small Molecule Screen Identifies XAV939 as a Novel Inhibitor of TEAD Transcriptional Activity To search for small molecule inhibitors of TEAD transcriptional activity, a library of in-house kinase and commercially available inhibitors were screened by measuring their effect on TEAD reporter activity in 293T cells (FIG. 3A). Whereas a few increased and 5 decreased the reporter activity by at least 50%, only one, XAV939, a tankyrase inhibitor initially identified as an inhibitor of Wnt signaling (Huang et al., "Tankyrase Inhibition Stabilizes Axin and Antagonizes Wnt Signalling," *Nature* 461(7264):614-620 (2009), which is hereby incorporated by reference in its entirety), decreased TEAD reporter activity by 75% (FIG. 3A). Thus, investigation was focused on the effects of XAV939 on Hippo pathway mutant and non-mutant cells.

Similar to results with dnTEAD4 overexpression, XAV939 treatment markedly decreased TEAD reporter activity and the expression of TEAD target genes in all cell lines tested with the exception of H2052 cells (FIG. 3B and FIGS. 4A-F), in which the reporter and TEAD target gene expression were only modestly affected (FIG. 3B and FIG. 4F). XAV939 treatment, as with dnTEAD4 overexpression (FIG. 1D), had no effect on the proliferation of 293T and MCF10A (FIG. 3C), nor was there any effect on the proliferation of 501T human diploid fibroblasts. Whereas XAV939 markedly inhibited the proliferation of Hippo pathway mutant H2373, MESO25, and 211H, it had no effect on H2052 cells (FIG. 3C), whose colony forming ability like that of the other Hippo mutant tumor lines was strongly inhibited by dnTEAD4 (FIG. 1D). Cell cycle analysis further revealed that those tumor lines whose proliferation was inhibited showed increased G1 and reduced S phase fractions without an obvious increase in apoptosis, while there was no detectable cell cycle alteration in those, which were not growth inhibited (FIG. 5). These results demonstrated that XAV939 phenocopied the G1 arrest induced by dnTEAD4 in Hippo mutant tumor lines that were sensitive to XAV939-mediated inhibition of TEAD transcriptional activity.

Example 3—XAV939 Regulates TEAD Transcriptional Activity Through Tankyrase Inhibition XAV939 was initially identified as an inhibitor of both tankyrase 1 and 2 (TNKS1/2), members of the Poly-ADP-ribosyltransferase (PARP) family of enzymes that regulate protein interactions and/or protein stability (Huang et al., "Tankyrase Inhibition Stabilizes Axin and Antagonizes Wnt Signalling," *Nature* 461(7264):614-620 (2009); Haikarainen et al., "Tankyrases: Structure, Function and Therapeutic Implications in Cancer," *Curr. Pharm. Design* 20(41):6472-6488 (2014), which are hereby incorporated by reference in their entirety). To determine whether XAV939's inhibition of TEAD-mediated transcription was indeed the result of TNKS inhibition, TEAD reporter activity as measured in 293T and H2373 cells treated with two other commercially available TNKS inhibitors, MN-64 and IWR-1, which each had a different chemical structure (Narwal et al., "Discovery of Tankyrase Inhibiting Flavones with Increased Potency and Isoenzyme Selectivity," *J. Med. Chem.* 56(20):7880-

7889 (2013); Chen et al., "Small Molecule-Mediated Disruption of Wnt-Dependent Signaling in Tissue Regeneration and Cancer," *Nat. Chem. Biol.* 5(2):100-107 (2009), which are hereby incorporated by reference in their entirety). Both compounds were able to inhibit TEAD reporter activity and target gene expression similarly to XAV939 (FIGS. 6A-B and FIGS. 7A-F). Furthermore, both MN-64 and IWR1 significantly decreased colony formation by H2373 but not by 293T cells (FIGS. 6C-D). In contrast, treatment with ABT-888, a PARP1/2 specific inhibitor (Donawho et al., "ABT-888, An Orally Active Poly(ADP-ribose) Polymerase Inhibitor that Potentiates DNA-Damaging Agents in Preclinical Tumor Models," *Clin. Cancer Res.* 13(9):2728-2737 (2007), which is hereby incorporated by reference in its entirety), did not affect TEAD reporter activity, target gene expression, or cell proliferation under the same conditions (FIGS. 6A-D and FIGS. 7A-F).

The expression of endogenous TNKS was also genetically abrogated by lentiviral-mediated transduction of an shRNA that targets TNKS1/2. TNKS1/2 knockdown markedly inhibited TEAD reporter activity, as well as target gene expression, in both 293T and H2373 cells (FIGS. 6E-F and FIGS. 7G-H). As with TNKS inhibitors, TNKS1/2 silencing inhibited the proliferation of H2373 but not 293T cells (FIGS. 6G-H). All of these results indicate that XAV939 functions through TNKS inhibition to specifically downregulate TEAD transcriptional activity and inhibit the proliferation of Hippo mutant tumor cells.

XAV939 was reported to inhibit Wnt signaling by stabilizing Axin and consequently leading to the degradation of ß-catenin (Huang et al., "Tankyrase Inhibition Stabilizes Axin and Antagonizes Wnt Signalling," *Nature* 461(7264): 614-620 (2009), which is hereby incorporated by reference in its entirety). Since the Wnt signaling pathway has recently been implicated in crosstalk with the Hippo pathway (Azzolin et al., "Role of TAZ as Mediator of Wnt Signaling," *Cell* 151(7):1443-1456 (2012); Konsavage et al., "Wnt/Beta-Catenin Signaling Regulates Yes-Associated Protein (YAP) Gene Expression in Colorectal Carcinoma Cells," *J. Biol. Chem.* 287(15):11730-11739 (2012); Azzolin et al., "YAP/TAZ Incorporation in the Beta-Catenin Destruction Complex Orchestrates the Wnt Response," *Cell* 158(1):157-170 (2014); Cai et al., "Beta-Catenin Destruction Complex-Independent Regulation of Hippo-YAP Signaling by APC in Intestinal Tumorigenesis," *Genes & Dev.* 29(14):1493-1506 (2015), which are hereby incorporated by reference in their entirety) the possibility that XAV939 suppressed TEAD transcriptional activity through inhibition of Wnt signaling was investigated. Thus, Hippo pathway mutant (H2373 and 211H) and non-mutant (293T and MCF10A) cell lines were analyzed for evidence of upregulated Wnt signaling by means of a TCF luciferase reporter for TCF-ß-catenin-dependent transcription. Whereas HCT116 colon carcinoma cells with Wnt pathway activation by mutant ß-catenin (Sekine et al., "Target Disruption of the Mutant Beta-Catenin Gene in Colon *Cancer Cell* Line HCT116: Preservation of Its Malignant Phenotype," *Oncogene* 21(38):5906-5911 (2002), which is hereby incorporated by reference in its entirety) exhibited high TCF reporter activity, the Hippo pathway mutant lines had very low or undetectable TCF reporter activity (FIG. 8A). These findings excluded the possibility that TEAD transcriptional activity in these lines was inhibited by XAV939 in a Wnt-dependent manner.

Example 4—TNKS Inhibition by XAV939 Blocks YAP-Dependent Transformation Through an S127 Phosphorylation-Independent Mechanism TEAD-mediated transcription is activated by its interaction with the co-transcription factor YAP, whose nuclear localization is highly regulated (Johnson and Halder, "The Two Faces of Hippo: Targeting the Hippo Pathway for Regenerative Medicine and Cancer Treatment," *Nat. Rev. Drug Disc.* 13(1):63-79 (2014), which is hereby incorporated by reference in its entirety). LATS1/2-mediated phosphorylation causes YAP to relocalize to the cytosol by a mechanism that involves 14-3-3 binding (Zhao et al., "Inactivation of YAP Oncoprotein by the Hippo Pathway is Involved in *Cell* Contact Inhibition and Tissue Growth Control," *Genes & Dev.* 21(21):2747-2761 (2007), which is hereby incorporated by reference in its entirety) and targets it for proteasomal degradation as well (Zhao et al., "A Coordinated Phosphorylation by Lats and CK1 Regulates YAP Stability Through SCF(Beta-TRCP)," *Genes & Dev.* 24(1):72-85 (2010), which is hereby incorporated by reference in its entirety). YAP activity is also regulated through phosphorylation-independent physical interaction with the angiomotins, a family of proteins that include AMOT, AMOTL1, and AMOTL2. Angiomotin proteins recruit YAP to tight junctions or to the actin cytoskeleton leading to YAP cytoplasmic retention (Zhao et al., "Angiomotin is a Novel Hippo Pathway Component That Inhibits YAP Oncoprotein," *Genes & Dev.* 25(1):51-63 (2011), which is hereby incorporated by reference in its entirety).

YAP overexpression in MCF10A cells promotes anchorage-independent colony formation in soft agar (Overholtzer et al., "Transforming Properties of YAP, a Candidate Oncogene on the Chromosome 11q22 Amplicon," *PNAS* 103(33): 12405-12410 (2006), which is hereby incorporated by reference in its entirety), a property that has been shown to correlate with in vivo tumorigenicity (Mori et al., "Anchorage-Independent *Cell* Growth Signature Identifies Tumors With Metastatic Potential," *Oncogene* 28(31):2796-2805 (2009), which is hereby incorporated by reference in its entirety). To test the ability of XAV939 to antagonize YAP overexpression by phosphorylation-dependent and independent mechanisms, YAP-WT or a YAP-S127A mutant, which has a point mutation in the LATS phosphorylation site required for YAP cytoplasmic retention by 14-3-3 (Zhao et al., "Inactivation of YAP Oncoprotein by the Hippo Pathway is Involved in *Cell* Contact Inhibition and Tissue Growth Control," *Genes & Dev.* 21(21):2747-2761 (2007), which is hereby incorporated by reference in its entirety) was stably overexpressed. Both significantly increased TEAD reporter activity and target gene expression, as well as colony formation in soft agar (FIGS. 9A-C and FIG. 8B). In contrast, overexpression of a YAP-S94A mutant, which is unable to bind TEAD (Zhao et al., "TEAD Mediates YAP-Dependent Gene Induction and Growth Control," *Genes & Dev.* 22(14):1962-1971 (2008), which is hereby incorporated by reference in its entirety), failed to induce TEAD transcriptional activity or anchorage-independent growth at similar levels of overexpression (FIGS. 9A-C and FIG. 8B). Of note, XAV939 completely abolished YAP-S127A as well as YAP-WT-induced anchorage-independent cell growth (FIG. 9D), consistent with a mechanism of XAV939 action independent of LATS1/2-mediated phosphorylation of YAP-S127.

A recent study indicated that HRAS-V12 overexpression stabilizes YAP protein levels and induces anchorage independent growth by a YAP-dependent mechanism in BJ cells (Hong et al., "Opposing Activities of the Ras and Hippo Pathways Converge on Regulation of YAP Protein Turnover," *EMBO J.* 33(21):2447-2457 (2014), which is hereby incorporated by reference in its entirety). When stably overexpressed HRAS-V12 in MCF10A cells, no changes were observed in either YAP protein levels or its phosphorylation at S127, whereas the RAS pathway was indeed activated as confirmed by increased levels of pERK (FIG. 8C). Moreover, TEAD reporter activity was not increased in HRAS-V12 overexpressing compared to vector control MCF10A cells (FIG. 8D), arguing that the RAS transformed phenotype, including acquisition of agar colony forming ability, was independent of deregulated Hippo transcription in these cells. XAV939 lacked any effect on HRAS-V12-induced colony formation (FIG. 9D), results consistent with the specificity of dnTEAD4, which blocked YAP but not RAS induced agar growth (FIG. 9E). In striking contrast, verteporfin, an inhibitor that has been reported to interfere with TEAD-YAP protein-protein interactions (Liu-Chittenden et al., "Genetic and Pharmacological Disruption of the TEAD-YAP Complex Suppresses the Oncogenic Activity of YAP," *Genes & Dev.* 26(12):1300-1305 (2012), which is hereby incorporated by reference in its entirety), completely blocked agar colony formation by both YAP and RAS transformed MCF10A cells (FIG. 9D). Together, these findings demonstrate that XAV939, but not verteporfin, specifically targets TEAD transcriptional activity and YAP-mediated transformation.

Example 5—XAV939 Increases YAP Cytoplasmic Localization Independent of S127 Phosphorylation To further investigate XAV939's mechanism of action, YAP sub-cellular localization was analyzed in the presence or absence of XAV939. Immunofluorescence staining demonstrated that YAP was mainly localized in the nucleus of untreated NF2 mutant H2373 cells, whereas XAV939 treatment induced YAP re-localization to the cytoplasm of these same cells (FIG. 10A). Moreover, H2373 cells treated with varying XAV939 concentrations did not show any significant differences in YAPS127 phosphorylation status as assessed by Western blot (FIG. 10B). The effects of XAV939 were next tested on TEAD transcriptional activity and subcellular localization of YAP-S127A in MCF10A cells. Both TEAD reporter activity and expression of target genes were inhibited by XAV939 treatment (FIGS. 10C-E). Furthermore, this decrease was associated with a significant shift of YAPS127A to the cytoplasm (FIG. 10F). All of these results indicated that XAV939 inhibited TEAD transcriptional activity by a mechanism involving YAP cytosolic re-localization independent of S127 phosphorylation, excluding a LATS-dependent mechanism of YAP sequestration by 14-3-3 and potentially implicating angiomotins.

Example 6—TNKS Inhibition Downregulates YAP Activity by Stabilizing Angiomotins TNKS catalyze the covalent linkage of ADP-ribose polymer chains to target proteins, regulating their ubiquitylation, stability, and function (Guettler et al., "Structural Basis and Sequence Rules for Substrate Recognition by Tankyrase Explain the Basis for Cherubism Disease," *Cell* 147(6): 1340-1354 (2011), which is hereby incorporated by reference in its entirety). It was previously reported that AMOT is degraded by the proteasome (Wang et al., "The Nedd4-Like Ubiquitin E3 Ligases Target Angiomotin/p130 to Ubiquitin-Dependent Degradation," *Biochem J.* 444(2):279-289 (2012), which is hereby incorporated by reference in its entirety). Moreover, in silico analysis revealed that all three angiomotin family members contain a recently identified consensus sequence for TNKS substrates (Guettler et al., "Structural Basis and Sequence Rules for Substrate Recognition by Tankyrase Explain the Basis for Cherubism Disease," *Cell* 147(6):1340-1354 (2011), which is hereby incorporated by reference in its entirety) and that this consensus sequence is evolutionary conserved (Table 1, with conserved portion depicted in bold and underlined text).

TABLE 1

| Tankyrase Binding Domain Motif |
|---|
| AMOT |
| H: Q D H H Q Q L V A H A A **R Q E P Q G Q E** I Q S E N L I M E K Q L |
| M: Q D H H Q Q L V A H - A **R Q E P Q G Q E** I Q S E N - - M E K Q L |
| D: Q D H H Q Q L V A H A A **R Q E P Q G Q E** I Q - E N - I M E K Q L |
| X: Q D - - - - L V - H A A **R Q E P Q G Q E** I Q - E N - - M E K Q - |
| Z: - D E H - - - V - H - A **R Q E P Q G Q E** L Q - - - - - - E K - - |
| H: human (SEQ ID NO: 35), M: mouse (SEQ ID NO: 36), D: dog (SEQ ID NO: 37), X: *xenopus* (SEQ ID NO: 38), Z: zebrafish (SEQ ID NO: 39) |
| AMOTL1 |
| H: T Q E D P Q M V Y Q S A **R Q E P Q G Q E** H Q V D N T V M E K Q V |
| M: T Q E D P Q M V Y Q S A **R Q E P Q G Q E** H Q G D N T V M E K Q V |
| D: A Q E D P P M V Y Q S A **R Q E P Q G Q E** H Q V D N T V M E K Q G |
| X: - Q E D P Q M V - Q S A **R Q E P Q G Q E** H - - D N T V M E K - - |
| Z: - - - - - - - - - - - - **R Q E P Q G Q E** H Q - D - - - M E K - - |
| H: human (SEQ ID NO: 40), M: mouse (SEQ ID NO: 41), D: dog (SEQ ID NO: 42), X: *xenopus* (SEQ ID NO: 43), Z: zebrafish (SEQ ID NO: 44) |
| AMOTL2 |
| H: A P E D S Q V L Q Q A T **R Q E P Q G Q E** H Q G G E N H L A E N T |
| M: A P E D S Q V L Q Q A T **R Q E P Q G Q E** H Q G G E T H L A E N - |
| D: A P E D T Q V L Q Q A T **R Q E P Q G Q E** H Q G G E S H L A E N T |
| Z: - - E - S - - - Q - - - **R Q E P Q G Q E** H Q G - - - H - - - - - |
| X: - - - - - - - - - - - - **R Q E P Q G Q E** - - - - - - - L - - - - |
| H: human (SEQ ID NO: 45), M: mouse (SEQ ID NO: 46), D: dog (SEQ ID NO: 47), X: *xenopus* (SEQ ID NO: 48), Z: zebrafish (SEQ ID NO: 49) |

Thus, it was hypothesized that XAV939 might act to stabilize angiomotins by inhibiting their tankyrase-mediated degradation.

By qRT-PCR and Western blot analyses, it was found that expression levels of the three-angiomotin genes varied in Hippo pathway mutant and wild-type cell lines (FIGS. 11A-B). In both 293T and H2373 cells, XAV939, MN-64, or IWR1 treatment did not markedly affect AMOT, AMOTL1, or AMOTL2 mRNA levels (FIGS. 11C-D), but strikingly increased angiomotin protein levels, as shown for AMOT and AMOTL2, respectively (FIG. 11E). In contrast, the PARP inhibitor, ABT-888, lacked any effect on either mRNA or protein expression of these same genes (FIGS. 11C-E). Increased AMOTL2 levels were also observed in Hippo mutant MESO25 and 211H cells upon XAV939 treatment (FIGS. 8E-F). These results indicated that TNKS inhibition either increased AMOT protein translation or stabilization. Cycloheximide chase experiments demonstrated increased half-life of endogenous AMOT in the presence of XAV939 (FIG. 11F), indicating a mechanism involving AMOT protein stabilization.

The ability of AMOT and TNKS to form an endogenous complex was next investigated, and it was observed that anti-AMOT co-immunoprecipitated TNKS (FIG. 11G). Increased TNKS protein levels were also detected in cell lysates in response to XAV939 treatment, consistent with stabilization of TNKS due to XAV939 inhibiting its autoparsylation and proteosome degradation (Smith et al., "Tankyrase, a Poly(ADP-Ribose) Polymerase at Human Telomeres," *Science* 282(5393):1484-1487 (1998); Callow et al., "Ubiquitin Ligase RNF146 Regulates Tankyrase and Axin to Promote Wnt Signaling," *PloS One* 6(7):e22595 (2011), which is hereby incorporated by reference in its entirety). Despite higher TNKS protein levels, reduced AMOT-TNKS complex formation was detected in the presence of XAV939 (FIG. 11G). Finally, co-immunoprecipitation of endogenous AMOT or YAP in the presence or absence of XAV939 treatment revealed an enrichment of the AMOT-YAP protein complex in treated cells (FIGS. 11H-I). The findings that XAV939 treatment results in increased YAP sequestration by AMOT as well as YAP cytoplasmic re-localization establish that TNKS inhibitors antagonize YAP-dependent TEAD transcriptional activity.

Example 7—Angiomotin Stabilization by XAV939 Determines its Ability to Inhibit Hippo Mutant Tumor Proliferation H2052 cells were exquisitely sensitive to dnTEAD4 inhibition of TEAD transcriptional activity and proliferation (FIGS. 1A-D) but resistant to XAV939 (FIGS. 2A-J). While XAV939 treatment resulted in increased AMOTL2 protein levels in H2052 cells at 24 hrs (FIG. 12A and FIG. 14A), time course experiments revealed that TEAD transcriptional activity was inhibited more strongly and durably in XAV939 sensitive H2373 cells compared to resistant H2052 cells over the 12 days of treatment (FIGS. 12B-C). Similarly, XAV939 treatment stabilized higher, durable levels of AMOTL2 protein in H2373 as compared to resistant H2052 cells (FIG. 12D). These differences were not accounted for by differences in AMOTL2 mRNA levels, which were similar in the two lines (FIG. 14B). TNKS have been reported to parsylate itself as well as several other substrates leading to their ubiquitin-mediated proteasome degradation (Riffell et al., "Tankyrase-Targeted Therapeutics: Expanding Opportunities in the PARP Family," *Nat. Rev. Drug Disc.* 11(12):923-936 (2012), which is hereby incorporated by reference in its entirety). To compare the effectiveness of XAV939 in both resistant and sensitive cell lines, TNKS protein levels were measured, which increased upon XAV939 treatment even more in the resistant line (FIG. 12D and FIG. 14C). Levels of PTEN, another reported TNKS substrate, increased modestly in both cell lines under the same conditions (FIG. 12D).

It was next sought to genetically establish that the mechanism by which XAV939 inhibited TEAD transcriptional activity was specifically mediated by inhibition of angiomotin degradation. Silencing of AMOTL2 expression in H2373 cells by lentiviral transduction of AMOTL2 shRNA (FIGS. 12E-F) almost completely rescued the inhibitory effects of XAV939 on TEAD transcriptional activity (FIGS. 12G-I and FIG. 14D) as well as on TEAD-mediated cell proliferation, as assayed by colony formation (FIG. 12J). All of these results indicate that the growth inhibitory effects of XAV939 in Hippo pathway mutant tumor cells were primarily due to its inhibition of TNKS-mediated angiomotin degradation.

To further establish that the durability and level of Angiomotin stabilization is crucial for XAV939 effectiveness in inhibiting TEAD dependent transcription and growth of Hippo deregulated tumor cells, AMOTL2 was overexpressed in Hippo regulated MCF10A and in Hippo deregulated 211H and H2052 cells, which were sensitive and resistant to XAV939 treatment, respectively (see FIG. 3C). AMOTL2 overexpression phenocopied XAV939 in its effects on TEAD reporter activity and growth in MCF10A and 211H cells (FIG. 13A-D). In contrast, AMOTL2 overexpression in resistant H2052 cells inhibited TEAD reporter activity to an extent sufficient to inhibit colony formation, which was not observed in response to XAV939, which failed to durably stabilize AMOTL2 in these cells (FIG. 13B-D). These findings strengthen the conclusions that tankyrase inhibitors act through stabilization of Angiomotin and that intrinsic resistance to these inhibitors can be due to lack of durable stabilization of this family of proteins.

Discussion of Examples 1-7

The present studies establish that human tumor lines harboring mutations in Hippo pathway core components, LATS or NF2, exhibited constitutively up-regulated TEAD transcriptional activity compared to Hippo wild-type cells, whose low levels of transcription were regulated by both serum and cell density. Much higher YAP protein levels were also observed in Hippo pathway mutant compared to wild-type cells, consistent with evidence that NF2 and LATS regulate YAP activity and protein stability (Zhao et al., "Inactivation of YAP Oncoprotein by the Hippo Pathway is Involved in *Cell* Contact Inhibition and Tissue Growth Control," *Genes & Dev.* 21(21):2747-2761 (2007); Zhao et al., "A Coordinated Phosphorylation by Lats and CK1 Regulates YAP Stability Through SCF(Beta-TRCP)," *Genes & Dev.* 24(1):72-85 (2010); Yin et al., "Spatial Organization of Hippo Signaling At the Plasma Membrane Mediated By the Tumor Suppressor Merlin/NF2," *Cell* 154(6):1342-1355 (2013), which are hereby incorporated by reference in their entirety). In contrast to Hippo wild-type cells whose TEAD-mediated transcription appeared to be dispensable for proliferation, Hippo pathway mutant tumor cells exhibited striking inhibition of proliferation in response to down regulation of TEAD transcriptional activity. These findings provide strong evidence for the importance of constitutively up regulated TEAD-mediated transcription for Hippo pathway mutant tumor cells. While the mechanisms involved in this dependency remain to be elucidated, the results indicate that agents that specifically target the constitutively high TEAD transcriptional activity in Hippo pathway deregulated tumors should exhibit a high therapeutic index in targeting such tumors.

The TNKS inhibitor, XAV939, was included in a screen for small molecule inhibitors of TEAD transcriptional activity based on reports of Wnt/Hippo pathway crosstalk (Azzolin et al., "Role of TAZ as Mediator of Wnt Signaling," *Cell* 151(7):1443-1456 (2012); Konsavage et al., "Wnt/Beta-Catenin Signaling Regulates Yes-Associated Protein (YAP) Gene Expression in Colorectal Carcinoma Cells," *J. Biol. Chem.* 287(15):11730-11739 (2012); Azzolin et al., "YAP/TAZ Incorporation in the Beta-Catenin Destruction Complex Orchestrates the Wnt Response," *Cell* 158(1):157-170 (2014), which are hereby incorporated by reference in their entirety) and evidence that XAV939 antagonizes TNKS parsylation-mediated degradation of Axin to inhibit canonical Wnt signaling (Huang et al., "Tankyrase Inhibition Stabilizes Axin and Antagonizes Wnt Signalling," *Nature* 461(7264):614-620 (2009), which is hereby incorporated by reference in its entirety). Having identified XAV939 in this screen, it was shown that it as well as other TNKS inhibitors and TNKS1/2 knockdown inhibited TEAD-mediated transcription, whereas an inhibitor of related members of the PARP superfamily lacked this activity. XAV939 phenocopied the effects of dnTEAD4 in inhibiting TEAD transcriptional activity and inducing a G1 growth arrest in most of the LATS or NF2 mutant tumor lines analyzed without detectable growth inhibitory effects on other cells tested. It was possible to exclude involvement of the canonical Wnt pathway, since none of the Hippo pathway mutant lines analyzed exhibited increased TCF reporter activity, a sensitive marker of Wnt pathway activation (Veeman et al., "Zebrafish Prickle, A Modulator of Noncanonical Wnt/Fz Signaling, Regulates Gastrulation Movements," *Curr. Biol.* 13(8):680-685 (2003), which is hereby incorporated by reference in its entirety).

Mechanistic studies revealed that XAV939 treatment did not affect YAP phosphorylation and resulted in cytoplasmic retention of YAP independent of YAP phosphorylation on S127, required for YAP cytoplasmic sequestration by 14-3-3 (Zhao et al., "Inactivation of YAP Oncoprotein by the Hippo Pathway is Involved in *Cell* Contact Inhibition and Tissue Growth Control," *Genes & Dev.* 21(21):2747-2761 (2007), which is hereby incorporated by reference in its entirety). Angiomotins, which sequester YAP independent of phosphorylation (Zhao et al., "Angiomotin is a Novel Hippo Pathway Component That Inhibits YAP Oncoprotein," *Genes & Dev.* 25(1):51-63 (2011), which is hereby incorporated by reference in its entirety), possess a recently identified highly conserved consensus sequence for TNKS substrates (Guettler et al., "Structural Basis and Sequence Rules for Substrate Recognition by Tankyrase Explain the Basis for Cherubism Disease," *Cell* 147(6):1340-1354 (2011), which is hereby incorporated by reference in its entirety), and TNKS inhibition increased angiomotin family protein expression by a mechanism involving protein stabilization. Moreover, increased angiomotin levels in response to XAV939 resulted in increased YAP complex formation with angiomotin, known to sequester YAP in the cytosol (Zhao et al., "Angiomotin is a Novel Hippo Pathway Component That Inhibits YAP Oncoprotein," *Genes & Dev.* 25(1):51-63 (2011), which is hereby incorporated by reference in its entirety). TNKS have been reported to influence other processes involved in growth control in addition to Wnt signaling including regulation of telomere length (TRF1), spindle polarity (NUMA), DNA repair (DNAPK), metabolism (GLUT4) and tumor suppression (PTEN) through paryslation-mediated degradation or stabilization (Riffell et al., "Tankyrase-Targeted Therapeutics: Expanding Opportunities in the PARP Family," *Nat. Rev. Drug Disc.* 11(12):923-936 (2012); Li et al., "Poly-ADP Ribosylation of PTEN By Tankyrases Promotes PTEN Degradation and Tumor Growth," *Genes & Dev.* 29(2):157-170 (2015), which are hereby incorporated by reference in their entirety). It was shown that knockdown of AMOTL2, the predominant angiomotin family member expressed in Hippo pathway mutant H2373 cells, almost completely rescued these cells from XAV939 inhibition of TEAD-mediated transcription and proliferation. All of these findings establish that TNKS inhibitors antagonize Hippo pathway mutant tumor cells primarily through angiomotin stabilization independent of other TNKS functions.

A small molecule inhibitor, verteporfin, and a polypeptide termed super-TDU, comprising the TEAD binding domain of VGLL4, a TEAD transcriptional repressor (Zhang et al., "VGLL4 Functions As A New Tumor Suppressor in Lung Cancer By Negatively Regulating the YAP-TEAD Transcriptional Complex," *Cell Res.* 24(3):331-343 (2014), which is hereby incorporated by reference in its entirety), have been reported to physically interfere with TEAD-YAP interactions and to antagonize TEAD transcriptional activity (Liu-Chittenden et al., "Genetic and Pharmacological Disruption of the TEAD-YAP Complex Suppresses the Oncogenic Activity of YAP," *Genes & Dev.* 26(12):1300-1305 (2012); Jiao et al., "A Peptide Mimicking VGLL4 Function Acts As A YAP Antagonist Therapy Against Gastric Cancer," *Cancer Cell* 25(2):166-180 (2014), which are hereby incorporated by reference in their entirety). Verteporfin suppressed liver tumor growth induced by YAP overexpression or NF2 inactivation in mice (Liu-Chittenden et al., "Genetic and Pharmacological Disruption of the TEAD-YAP Complex Suppresses the Oncogenic Activity of YAP," *Genes & Dev.* 26(12):1300-1305 (2012), which is hereby incorporated by reference in its entirety), and super-TDU suppressed growth of gastric tumor xenografts with Hippo pathway deregulation (Jiao et al., "A Peptide Mimicking VGLL4 Function Acts As A YAP Antagonist Therapy Against Gastric Cancer," *Cancer Cell* 25(2):166-180 (2014), which is hereby incorporated by reference in its entirety). While it is not yet known the degree to which super-TDU may be specific for Hippo pathway deregulated tumor cells, it was found that verteporfin blocked anchorage-independent growth of RAS transformed cells, which was not inhibited by either dnTEAD4 or XAV939. These results argue against verteporfin's Hippo pathway specific actions. In line with these findings, a recent publication showed a YAP-independent tumor suppressive function of verteporfin in colorectal cancer (Zhang et al., "Tumor-Selective Proteotoxicity of Verteporfin Inhibits Colon Cancer Progression Independently of YAP1," *Sci. Signal* 8(397):ra98 (2015), which is hereby incorporated by reference in its entirety).

This paper reported identification of XAV939 in a screen for small molecule inhibitors of TEAD transcriptional activity (Wang et al., "Tankyrase Inhibitors Target YAP by Stabilizing Angiomotin Family Proteins," *Cell Reports* 13(3):524-532 (2015), which is hereby incorporated by reference in its entirety). They showed that XAV939 stabilized angiomotin and inhibited acini formation in matrigel by YAP overexpressing MCF10A cells (Wang et al., "Tankyrase Inhibitors Target YAP by Stabilizing Angiomotin Family Proteins," *Cell Reports* 13(3):524-532 (2015), which is hereby incorporated by reference in its entirety). They also reported that the E3 ligase, RNF146, previously identified to work in concert with TNKS to target parslyated proteins such as Axin and PTEN for proteosome-mediated degradation (Callow et al., "Ubiquitin Ligase RNF146 Regulates Tankyrase and Axin to Promote Wnt Signaling," *PloS One* 6(7):e22595 (2011); Li et al., "Poly-ADP Ribosylation of PTEN By Tankyrases Promotes PTEN Degradation and Tumor Growth," *Genes & Dev.* 29(2):157-170 (2015), which are hereby incorporated by reference in their entirety), was the E3 ligase responsible for TNKS-mediated angiomotin degradation (Wang et al., "Tankyrase Inhibitors Target YAP by Stabilizing Angiomotin Family Proteins," *Cell Reports* 13(3):524-532 (2015), which is hereby incorporated by reference in its entirety). There is previous evidence that angiomotins have tumor suppressive functions by sequestering YAP in the cytosol and by causing cellular transformation when depleted in immortalized MDCK and MCF10A cells (Zhao et al., "Angiomotin is a Novel Hippo Pathway Component That Inhibits YAP Oncoprotein," *Genes & Development* 25(1):51-63 (2011); Wang et al., "Angiomotin-Like Proteins Associate With and Negatively Regulate YAP1," *J. Biol. Chem.* 286(6):4364-4370 (2011), which are hereby incorporated by reference in their entirety). However, there is also a report showing that angiomotins can play a positive role in YAP-mediated cell proliferation in the liver (Yi et al., "The p130 Isoform of Angiomotin is Required for Yap-Mediated Hepatic Epithelial Cell Proliferation and Tumorigenesis," *Sci. Signal* 6(291):ra77 (2013), which is hereby incorporated by reference in its entirety). The present studies directly establish the biological importance of this mechanism in specifically targeting the proliferation of human tumor cells with mutations in Hippo pathway core components.

Among tumor lines with Hippo pathway mutations analyzed in the present studies, one mesothelioma, H2052, with both LATS2 and NF2 mutations, was found to be resistant to XAV939 despite its striking sensitivity to dnTEAD4 inhibition of TEAD-mediated transcription and proliferation. AMOTL2, the most abundant angiomotin in both resistant H2052 and sensitive H2373 tumor cells, showed lower and less durable stabilization in H2052 cells in response to XAV939. One possible explanation could be that another ubiquitin ligase(s) acts independently of TNKS, to preferentially inhibit angiomotin accumulation in the resistant tumor cells. However, mechanistic understanding, as well as how frequent is the recurrence such resistance and the effectiveness of TNKS inhibitors in tumors with other Hippo pathway lesions, awaits further studies. Nonetheless, these findings indicate that the level of angiomotin protein stabilization could potentially provide a useful biomarker with which to assess the sensitivity of Hippo pathway mutant tumors to TNKS inhibitors.

The findings here that TNKS inhibitors predominantly induced G1 arrest rather than cell death in Hippo pathway mutant tumor cells have potential parallels with the G1 arrest induced by tyrosine kinase pathway inhibitors in solid tumor cells (Shawver et al., "Smart Drugs: Tyrosine Kinase Inhibitors in Cancer Therapy," *Cancer Cell* 1(2):117-123 (2002); Zhang et al., "Targeting Cancer with Small Molecule Kinase Inhibitors," *Nature Reviews Cancer* 9:28-39 (2009), which are hereby incorporated by reference in their entirety). Several studies revealed that growth factor signaling pathways also activate pro-survival signaling and can be used in cooperation with standard chemo/irradiation therapies (Wu et al., "Intercalated Combination of Chemotherapy and Erlotinib for Patients with Advanced Stage Non-Small-*Cell* Lung Cancer (FASTACT-2): A Randomised, Double-Blind Trial," *Lancet Oncol.* 14:777-786 (2013); OuYang et al., "Combination of EGFR-TKIs and Chemotherapy as First-Line Therapy for Advanced NSCLC: A Meta-Analysis," *PLoS One* 8:e79000 (2013), which are hereby incorporated by reference in their entirety).

Under physiological conditions, growth factor signaling pathways are subject to stringent regulation through negative feedback mechanisms, which limit the strength and duration of such signaling. The development of biologically targeted therapies for oncogene activated signaling has revealed that pathway inhibition can relieve negative feedback, which can then promote oncogenic signals and contribute to therapy resistance. For example, a recent screen for genes increasing the efficacy of RAF inhibitors in cancer cells harboring BRAF-V600E mutations identified YAP as a key to drug resistance, and combined YAP and RAF or MEK inhibition was found to be synthetically lethal for BRAF and RAS mutant tumors (Lin et al., "The Hippo Effector YAP Promotes Resistance to RAF- and MEK-Targeted Cancer Therapies," *Nat. Genet.* 47(3):250-256 (2015), which is hereby incorporated by reference in its entirety). Thus, it will be of interest to determine the extent to which TNKS inhibitors cooperate with RAF or MEK inhibitors in targeting such tumors as well as how BRAF or MEK inhibition may cooperate with down regulation of YAP-dependent TEAD transcriptional activity by TNKS inhibitors in Hippo pathway mutant tumors.

Within the PARP superfamily, specific inhibitors of PARP1/2 are now in the clinic (Riffell et al., "Tankyrase-Targeted Therapeutics: Expanding Opportunities In the PARP Family," *Nat. Rev. Drug Discov.* 11(12):923-936 (2012), which is hereby incorporated by reference in its entirety). Efforts aimed at developing TNKS inhibitors to target Wnt activated tumors have recently led to new compounds with better drug-like properties compared to XAV939 with evidence of some efficacy in Wnt tumor models (Waaler et al., "A Novel Tankyrase Inhibitor Decreases Canonical Wnt Signaling in Colon Carcinoma Cells and Reduces Tumor Growth in Conditional APC Mutant Mice," *Cancer Res.* 72(11):2822-2832 (2012); Lau et al., "A Novel Tankyrase Small-Molecule Inhibitor Suppresses APC Mutation-Driven Colorectal Tumor Growth," *Cancer Res.* 73(10):3132-3144 (2013), which are hereby incorporated by reference in their entirety). Nonetheless, stability issues, dose-limiting toxicity, and weight loss attributed to Wnt inhibitory effects in the gastrointestinal tract (Waaler et al., "A Novel Tankyrase Inhibitor Decreases Canonical Wnt Signaling in Colon Carcinoma Cells and Reduces Tumor Growth in Conditional APC Mutant Mice," *Cancer Res.* 72(11):2822-2832 (2012); Lau et al., "A Novel Tankyrase Small-Molecule Inhibitor Suppresses APC Mutation-Driven Colorectal Tumor Growth," *Cancer Res.* 73(10):3132-3144 (2013), which are hereby incorporated by reference in their entirety) pose challenges to their application as therapeutic agents. Thus, TNKS inhibitors with improved drug-like properties and/or less toxicity will likely be needed. However, the refractory nature of tumors such as mesothelioma to current treatments and the identification of angiomotin, whose stabilization by TNKS inhibitors specifically antagonizes the proliferation of such tumor cells, argues that approaches aimed at angiomotin stabilization could eventually lead to new targeted therapies for the increasing array of Hippo pathway deregulated tumors for which there are as yet no effective therapies.

Although some embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating a tumor comprising a Hippo pathway mutant in a subject, said method comprising:

administering to a subject identified as having a Hippo pathway mutant tumor a tankyrase inhibitor, wherein the tumor is susceptible to treatment with the tankyrase inhibitor; wherein the tankyrase inhibitor increases the level of an angiomotin protein family member present in cells of the tumor by at least 4-fold, as compared to when the tankyrase inhibitor is not administered; wherein the increased level of the angiomotin protein family member is sustained for at least 6 days after said administering; and wherein said administering is carried out to treat the tumor in the subject.

2. The method according to claim 1, wherein the tumor comprises mutations in one or more Hippo pathway genes selected from the group consisting of LATS1, LATS2, NF2, and YAP.

3. The method according to claim 1, wherein the tankyrase inhibitor is a small molecule.

4. The method according to claim 3, wherein the tankyrase inhibitor is selected from XAV939, MN-64, IWRI, a pyrimidinone nicotinamide mimetic, and combinations thereof.

5. The method according to claim 1 wherein the angiomotin protein family member is selected from the group consisting of AMOT, AMOTL1, and AMOTL2.

6. The method according to claim 1, wherein the subject is a human.

7. The method according to claim 1 further comprising:

identifying a subject with a tumor susceptible to treatment with the tankyrase inhibitor prior to said administering.

8. The method according to claim 7, wherein said identifying comprises:

obtaining a tissue sample from a tumor in the subject and determining whether the tissue sample from the tumor exhibits a Hippo pathway mutation and if so, the level and durability of angiomotin stabilization in the tissue sample from the tumor following treatment with the tankyrase inhibitor.

9. A method of treating cancer associated with a tumor comprising a Hippo pathway mutant in a subject, said method comprising:

administering a tankyrase inhibitor to a subject identified as having a cancer comprising a Hippo pathway mutant tumor susceptible to treatment with a tankyrase inhibitor, wherein the tankyrase inhibitor increases the level of an angiomotin protein family member present in cells of the tumor by at least 4-fold, as compared to when the tankyrase inhibitor is not administered; wherein the increased level of the angiomotin protein family member is sustained for at least 6 days after said administering; and wherein the tankyrase inhibitor treats the subject for cancer.

10. The method according to claim 9, wherein the tumor comprises a mutation in one or more Hippo pathway genes selected from the group consisting of LATS1, LATS2, NF2, and YAP.

11. The method according to claim 9, wherein the tankyrase inhibitor is a small molecule.

12. The method according to claim 9, wherein the tankyrase inhibitor is selected from XAV939, MN-64, IWRI, a pyrimidinone nicotinamide mimetic, and combinations thereof.

13. The method according to claim 9, wherein the angiomotin protein family member is selected from the group consisting of AMOT, AMOTL1, and AMOTL2.

14. The method according to claim 9, wherein the subject is a human.

* * * * *